(12) United States Patent
Kazantsev et al.

(10) Patent No.: US 9,737,525 B2
(45) Date of Patent: Aug. 22, 2017

(54) SMALL MOLECULE ACTIVATORS OF NRF2 PATHWAY

(71) Applicants: The General Hospital Corporation, Boston, MA (US); The Regents of the University of California, Oakland, CA (US)

(72) Inventors: Aleksey G. Kazantsev, Brighton, MA (US); Leslie M. Thompson, Irvine, CA (US); Ruben Abagyan, La Jolla, CA (US); Malcolm Casale, Mission Viejo, CA (US)

(73) Assignees: The General Hospital Corporation, Boston, MA (US); The Regents of the University of California, Oakland, CA (US)

(*) Notice: Subject to any disclaimer, the term of this patent is extended or adjusted under 35 U.S.C. 154(b) by 0 days.

(21) Appl. No.: 14/892,353

(22) PCT Filed: Jun. 6, 2014

(86) PCT No.: PCT/US2014/041335
§ 371 (c)(1),
(2) Date: Nov. 19, 2015

(87) PCT Pub. No.: WO2014/197818
PCT Pub. Date: Dec. 11, 2014

(65) Prior Publication Data
US 2016/0101098 A1 Apr. 14, 2016

Related U.S. Application Data

(60) Provisional application No. 61/886,970, filed on Oct. 4, 2013, provisional application No. 61/832,319, filed on Jun. 7, 2013.

(51) Int. Cl.
*A61K 31/47* (2006.01)
*A61K 31/4709* (2006.01)
*A61K 31/4196* (2006.01)
*A61K 31/4439* (2006.01)

(52) U.S. Cl.
CPC ...... *A61K 31/4709* (2013.01); *A61K 31/4196* (2013.01); *A61K 31/4439* (2013.01)

(58) Field of Classification Search
USPC .................................................. 514/314, 311
See application file for complete search history.

(56) References Cited

U.S. PATENT DOCUMENTS

| | | | |
|---|---|---|---|
| 4,522,811 A | 6/1985 | Eppstein et al. | |
| 6,468,798 B1 | 10/2002 | Debs et al. | |
| 6,471,996 B1 | 10/2002 | Sokoll et al. | |
| 6,472,375 B1 | 10/2002 | Hoon et al. | |
| 8,153,803 B2 * | 4/2012 | Kazantsev | C07D 401/12 |
| | | | 546/171 |
| 2005/0209287 A1 | 9/2005 | Olson et al. | |
| 2006/0025337 A1 | 2/2006 | Sinclair et al. | |
| 2008/0021063 A1 * | 1/2008 | Kazantsev | C07D 295/26 |
| | | | 514/314 |
| 2009/0069301 A1 | 3/2009 | Milburn et al. | |

OTHER PUBLICATIONS

International Search Report and Written Opinion mailed Dec. 16, 2014 in international application No. PCT/US14/41335, 15 pgs.
Abagyan and Totrov, "Biased probability Monte Carlo conformational searches and electrostatic calculations for peptides and proteins," Journal of molecular biology, 1994, 235:983-1002.
Abagyan et al., "ICM—a new method for protein modelling and design. Applications to docking and structure prediction from the distolied native conformation," J. Comp. Chem., 1994, 15:488-506.
Apostol et al., "Mutant huntingtin alters MAPK signaling pathways in PC12 and striatal cells: ERK1/2 protects against mutant huntingtin-associated toxicity," Human Molecular Genetics, 2006, 15:273-285.
Auf dem Keller et al., "Nrf Transcription Factors in Keratinocytes Are Essential for Skin Tumor Prevention but Not for Wound Healing," Mol. Cell. Biol., May 2006, 26(10):3773-84.
Auluck et al., "α-Synuclein: Membrane Interactions and Toxicity in Parkinson's Disease," Annual Rev. Cell Dev. Biol., 2010, 26: 211-233.
Bai et al., "Prevention by sulforaphane of diabetic cardiomyopathy is associated with up-regulation of Nrf2 expression and transcription activation," J. Mol. Cell Cardiol., Apr. 2013, 57:82-95.
Barone et al., Genetic activation of Nrf2 signaling is sufficient to ameliorate neurodegenerative phenotypes in a *Drosophila* model of Parkinson's disease, Dis Model Mech , 2011, 4 (5): 701-077.
Beamer et al., "Conserved solvent and side-chain interactions in the 1.35 Angstrom structure of the Kelch domain of Keap1," Acta. clystallographica., 2005, 61:1335-1342.
Bjorkqvist et al., "A novel pathogenic pathway of immune activation detectable before clinical onset in Huntington's disease," The Journal of experimental medicine, 2008, 205:1869-1877.
Bonifati and Kishore, "Role of complement in neurodegeneration and Neuroinflammation," Molecular immunology, 2007, 44:999-1010.
Browne and Beal, "Oxidative damage in Huntington's disease pathogenesis," Antioxid Redox Signal, 2006, 8:2061-2073.
Burton et al., "In vivo modulation of the Parkinsonian phenotype by Nrf2," Neurotoxicology, 2006, 27(6): 1094-1100.

(Continued)

*Primary Examiner* — Rei-Tsang Shiao
(74) *Attorney, Agent, or Firm* — Fish & Richardson P.C.

(57) ABSTRACT

This disclosure relates to compounds that act as activators of the NRF2/KEAP1/ARE pathway. Specifically, the compounds provided herein can act as high affinity reversible bindings for the NRF2 inhibitor, KEAP1. In some cases, NRF2/KEAP1/ARE pathway activation compounds are capable of repressing expression of inflammatory markers and/or reducing levels of TNFa to provide neuroprotective anti-inflammatory effects in the CNS. Such compounds are useful in the treatment of a variety of diseases including Huntington's disease, Parkinson's disease, Alzheimer's disease, inflammation, and cancer.

11 Claims, 35 Drawing Sheets

(56) References Cited

OTHER PUBLICATIONS

Calkins et al., "Astrocyte-specific overexpression of Nrf2 protects striatal neurons from mitochondiral complex II inhibition," Toxicol. Sci., 2010, 115:557-568.

Castellano et al., "Biochemical Basis of the Antidiabetic Activity of Oleanolic Acid and Related Pentacyclic Triterpenes," Diabetes., Jun. 2013, 62(6):1791-9.

Chaturvedi et al., "Impairment of PGC-1alpha expression, neuropathology and hepatic steatosis in a transgenic mouse model of Huntington's disease following chronic energy deprivation," Hum. Mol. Genet., Aug. 2010, 19(16):3190-205.

Chen et al., "The protection by Octreotide against experimental ischemic stroke: Up-regulated transcription factor Nrf2, HO-1 and down-regulated NF-κB expression," Brain Res., Sep. 2012, 1475:80-7.

Chen et al.,"Nrf2-mediated neuroprotection in the MPTP mouse model of Parkinson's disease: Critical role for the astrocyte," PNAS, 2009, 106(8): 2933-8.

Cheung et al., "Ras GTPase-activating-like protein (IQGAP1) mediates Nrf2 activation via MEK-ERK pathway," The Journal of biological Chemistry, Aug. 2013, 288(31): 22378-86.

Chopra et al., The Sirtuin 2 Inhibitor AK-7 Is Neuroprotective in Huntington's Disease Mouse Models, Cell Reports, Dec. 2012, 2:1492-1497.

Chun et al., Dopaminergic cell death induced by MPP, oxidant and specific neurotoxicants shares the common molecular mechanism, J Neurochem, 2001, 76: 1010-21.

Cordova et al., "The NRF2 gene variant, -653G/A, is associated with nephritis in childhood-onset systemic lupus erythematosus," Lupus, Sep. 2010, 19(10):1237-42.

Crittenden et al., "CalDAG-GEFI downregulation in the striatum as a neuroprotective change in Huntington's disease," Human Molecular Genetics, 2010, 19(9):1756-1765.

Cullinan et al., "The Keap1-BTB protein is an adaptor that bridges Nrf2 to a Cul3-based E3 ligase: oxidative stress sensing by a Cul3-Keap1 ligase," Molecular and Cellular Biology, Oct. 2004, 24:8477-8486.

Dalrymple et al., "Proteomic profiling of plasma in Huntington's disease reveals neuroinflammatory activation and biomarker candidates," Journal of Proteome Research, 2007, 6:2833-2840.

Das et al., "CBP/p300-mediated acetylation of histone H3 on lysine 56," Nature, 2009, 459:113-117.

D'Oria et al., "Frataxin Deficiency Leads to Reduced Expression and Impaired Translocation of NF-E2-Related Factor (Nrf2) in Cultured Motor Neurons," Int. J. Mol. Sci., Apr. 2013, 14(4):7853-65.

Du et al., "Akt/Nrf2 Activated Upregulation of Heme Oxygenase-1 Involves in the Role of Rg1 Against Ferrous Iron-Induced Neurotoxicity in SK-N-SH Cells," Neurotox Res., Jul. 2013, 24(1):71-9.

Ehrlich et al., "ST14A cells have propeliies of a medium-size spiny neuron," Exp. Neurol., 2001, 167:215-226.

Ellrichmann et al., "Efficacy of fumaric acid esters in the R6/2 and YAC128 models of Huntington's disease," PloS One, 2011, 6:e16172.

Fox et al., "BG-12 (dimethyl fumarate): a review of mechanism of action, efficacy, and safety," Curr Med Res Opin, 2014, 30(2):251-62.

Frank-Cannon et al., "Does neuroinflammation fan the flame in neurodegenerative diseases?," Molecular Neurodegeneration, 2009, 4:47.

Gan et al., "Astrocyte-Specific Overexpression of Nrf2 Delays Motor Pathology and Synuclein Aggregation throughout the CNS in the Alpha-Synuclein Mutant (A53T) Mouse Model," J. Neurosci., Dec. 2012, 32(49):17775-17787.

Goode et al., "ALS-FTLD associated mutations of SQSTM1 impact on Keap1-Nrf2 signalling," Molecular and Cellular Neuroscience, 2016, 76: 52-58.

Gu et al., "Mitochondrial function, GSH and iron in neurodegeneration and Lewy body diseases," J Neurol Sci ,1998, 158(1): 24-9.

Gunjima et al., "3,4-Dihydroxybenzalacetone Protects Against Parkinson's Disease-Related Neurotoxin 6-OHDA Through Akt/Nrf2/Glutathione Pathway," Cell Biochem., Jan. 2014, 115:151-160.

Gurney et al., "Motor Neuron Degeneration in Mice That Express a Human Cu,Zn Superoxide Dismutase Mutation," Science, Jun. 1994, 264:1772-1775.

Hamajima et al., "Intranasal Administration of HIV-DNA Vaccine Formulated with a Polymer, Carboxymethylcellulose, Augments Mucosal Antibody Prodcution and Cell-Mediated Immune Response," Clin. Immunol. Immunopathol., Aug. 1998, 88(2):205-10.

Hersch and Rosas, "Neuroprotection for Huntington's disease: ready, set, slow," Neurotherapeutics, 2008, 5:226-236.

Hirota et al., "Acceleration of UVB-induced photoageing in nrf2 gene-deficient mice," Exp. Dermatol., Aug. 2011, 20(8):664-8.

Hoozemans and Scheper, "Endoplasmic reticulum: The unfolded protein response is tangled in neurodegeneration," The International Journal of Biochemistry & Cell Biology, 2012, 44: 1295-1298.

Howland et al., "Focal loss of the glutamate transporter EAAT2 in a transgenic rat model of SOD1 mutant-mediated amyotrophic lateral sclerosis (ALS)," PNAS, Feb. 2002, 99:1604-1609.

Hseu et al., "Ellagic acid protects human keratinocyte (HaCaT) cells against UVA-induced oxidative stress and apoptosis through the upregulation of the HO-1 and Nrf-2 antioxidant genes," Food Chem. Toxicol., May 2012, 50(5):1245-55.

Hu et al., "Discovery of a small-molecule inhibitor and cellular probe of Keap1-Nrf2 protein-protein interaction," Bioorganic & Medicinal Chemistry Letters, May 2013, 23:3039-3043.

Innamorato et al., "Role of microglial redox balance in modulation of neuroinflammation," Current opinion in neurology, 2009, 22:308-314.

International Preliminary Report on Patentability in International Application No. PCT/US2014/041335, mailed Dec. 8, 2015, 7 pages.

Itoh et al., "An Nrf2/small Mafheterodimer mediates the induction of phase II detoxifying enzyme genes through antioxidant response elements," Biochemical and biophysical research communications, 1997, 236:313-322.

Jazwa et al., "Pharmacological targeting of the transcription factor Nrf2 at the basal ganglia provides disease modifying therapy for experimental parkinsonism," Antioxid Redox Signal, 2011, 14(12):2347-60.

Jin et al., "Impaired mitochondrial dynamics and Nrf2 signaling contribute to compromised responses to oxidative stree in striatal cells expressing full-length mutant huntingtin," PloS one, 2013, 8:e57932.

Johnson et al., The Nrf2-ARE pathway: an indicator and modulator of oxidative stress in neurodegeneration. Annals of the New York Academy of Sciences, 2008, 1147:61-69.

Johri and Beal, "Antioxidants in Huntington's disease," Biochim Biophys Acta., May 2012, 1822(5):664-674.

Joshi and Johnson, "The Nrf2-Are Pathway: A Valuable Therapeutic Target for the Treatment of Neurodegenerative Diseases," Recent Pat CNS Drug Discov., Dec. 2012, 7(3): 218-229.

Jung and Kwak, "The Nrf2 system as a potential target for the development of indirect antioxidants," Molecules, 2010, 15; 7266-7291.

Kaidery et al., "Targeting Nrf2-mediated gene transcription by extremely potent synthetic triterpenoids attenuate dopaminergic neurotoxicity in the MPTP mouse model of Parkinson's disease," Antioxid Redox Signal, 2013, 18 (2) 139-57.

Kanninen et al., "Intrahippocampal injection of a lentiviral vector expressing Nrf2 improves spatial learning in a mouse model of Alzheimer's disease," PNAS, Sep. 2009, 106(38):16505-10.

Kanninen et al., "Nuclear factor erythroid 2-related factor 2 protects against beta amyloid," J. Mol. Cell Neurosci., Nov. 2008, 39(3):302-13.

Kanno et al., "A novel small molecule, N-(4-(2-pyridyl)(1,3-thiazol-2-yl))-2-(2,4,6-trimethylphenoxy) acetamide, selectively protects against oxidative stress-induced cell death by activating the Nrf2-ARE pathway: Therapeutic implications for ALS," Free Radic Biol Med, 2012, 53 (11): 2028-42.

(56) References Cited

OTHER PUBLICATIONS

Kensler et al., "Cell survival responses to environmental stresses via the Keap1-Nrf2-ARE pathway," Annual Review of Pharmacology and Toxicology, 2007, 47:89-116.
Killoran and Biglan, "Therapeutics in Huntington's Disease," Current Treatment Options in Neurology, Apr. 2012, 14(2): 137-149.
Kim and Vaziri, "Contribution of impaired Nrf2-Keap1 pathway to oxidative stress and inflammation in chronic renal failure," Am. J. Physiol. Renal Physiol., Mar. 2010, 298(3):F662-F671.
Koh et al., "Transcription factor Nrf2 suppresses LPS-induced hyperactivation of BV-2 microglial Cells," Journal of Neuroimmunology, Apr. 2011, 233:160-167.
Kraft et al., "Activated microglia proliferate at neurites of mutant huntingtin-expressing neurons," Neurobiology of Aging, Mar. 2012, 33(621):e617-633.
Kumar et al., "Lucidone protects human skin keratinocytes against free radical-induced oxidative damage and inflammation through the up-regulation of HO-1/Nrf2 antioxidant genes and down-regulation of NF-κB signaling pathway," Food Chem. Toxicol., Sep. 2013, 59:55-66.
Kwon et al., "Assurance of mitochondrial integrity and mammalian longevity by the p62-Keap1-Nrf2-Nqo1 cascade," EMBO Rep., Feb. 2012, 13(2):150-6.
LaPash Daniels et al., "Beneficial effects of Nrf2 overexpression in a mouse model of Alexander disease," J. Neurosci., Aug. 2012, 32:10507-10515.
Lastres-Becker et al., "Fractalkine activates NRF2/NFE2L2 and heme oxygenase 1 to restrain tauopathy-induced microgliosis," Brain, 2014, 137: 78-91.
Lastres-Becker et al., "α-Synuclein expression and Nrf2 deficiency cooperate to aggravate protein aggregation, neuronal death and inflammation in early-stage Parkinson's disease," Human Mol Genetics, 2012, 21(14): 3173-92.
Le Ber et al., "SQSTM1 Mutations in French Patients With Frontotemporal Dementia or Frontotemporal Dementia With Amyotrophic Lateral Sclerosis," JAMA Neurol., Nov. 2013, 70: 1403-1410.
Lee et al., "An auto-regulatory loop between stress sensors INrf2 and Nrf2 controls their cellular abundance," The Journal of Biological Chemistry, 2007, 282:36412-36420.
Lee et al., "Dimerumic acid attenuates receptor for advanced glycation endproducts signal to inhibit inflammation and diabetes mediated by Nrf2 activation and promotes methylglyoxal metabolism into d-lactic acid," Free Radic. Biol. Med., Jul. 2013, 60:7-16.
Lee et al., "Identification of the NF-E2-related factor-2-dependent genes conferring protection against oxidative stress in primary cortical astrocytes using oligonucleotide microarray analysis," The Journal of Biological Chemistry, 2003, 278:12029-12038.
Lee et al., "Mechanisms of Oxidative Damage in Multiple Sclerosis and Neurodegenerative Diseases: Therapeutic Modulation via Fumaric Acid Esters," Int. J. Mol. Sci., 2012, 13(9):11783-803.
Leiser and Miller, "Nrf2 Signaling, a Mechanism for Cellular Stress Resistance in Long-Lived Mice," Mol. Cell Biol., Feb. 2010, 30(3):871-84.
Lewis et al., "Nrf2, a Guardian of Healthspan and Gatekeeper of Species Longevity," Integr. Comp. Biol., Nov. 2010, 50(5):829-43.
Li et al., "Allicin ameliorates cognitive deficits ageing-induced learning and memory deficits through enhancing of Nrf2 antioxidant signaling pathways," Neurosci. Lett., Apr. 2012, 514(1):46-50.
Li et al., "Crystal structure of the Kelch domain of human Keap 1," The Journal of Biological Chemistry, 2004, 279:54750-54758.
Li et al., "Deficient Rab 11 activity underlies glucose hypometabolism in primary neurons of Huntington's disease mice," Biochemical and Biophysical Research Communications, May 2012, 451:727-730.
Li et al., "Prevention of Diabetic Complications by Activation of Nrf2: Diabetic Cardiomyopathy and Nephropathy," Exp Diabetes Res., 2012, 2012:216512.

Li et al., "Puerarin attenuates neuronal degeneration in the substantia nigra of 6-OHDA-lesioned rats through regulating BDNF expression and activating the Nrf2/ARE signaling pathway," Brain Res., Jul. 2013, 1523:1-9.
Li et al., "The Neuroprotection of Oxymatrine in Cerebral Ischemia/Reperfusion Is Related to Nuclear Factor Erythroid 2-Related Factor 2 (Nrf2)-Mediated Antioxidant Response: Role of Nrf2 and Hemeoxygenase-1 Expression," Biol. Pharm. Bull., 2011, 34(5):595-601.
Linker et al., Fumaric acid esters exert neuroprotective effects in neuroinflammation via activation of the Nrf2 antioxidant pathway, Brain, 2011, 134: 678-92.
Lo et al., "Structure of the Keap1:Nrf2 interface provides mechanistic insight into Nrf2 signaling," The EMBO Journal, 2006, 25:3605-3617.
Luthi-Carter et al., "SIRT2 inhibition achieves neuroprotection by decreasing sterol biosynthesis," PNAS, Apr. 2010, 107:7927-7932.
Mangiarini et al., "Exon 1 of the HD gene with an expanded CAG repeat is sufficient to cause a progressive neurological phenotype in transgenic mice," Cell, Nov. 1996, 87:493-506.
Marcotte et al., "Small molecules inhibit the interaction of Nrf2 and the Keap1 Kelch domain through a non-covalent mechanism," Biorganic & Medicinal Chemistry, Jul. 2013, 21(14): 4011-9.
Marsh et al., "Fly models of Huntington's disease," Human Molecular Genetics, 2003, 12: R187-R193.
Maxwell et al., "The Sirtuin 2 microtubule deacetylase is an abundant neuronal protein that accumulates in the aging CNS," Human Molecular Genetics, 2011, 20:3986-3996.
Mazzuferi et al., "Nrf2 defense pathway: Experimental evidence for its protective role in epilepsy," Ann Neural., May 2013, 74:560-568.
McDonald et al., "A novel gene containing a trinucleotide repeat that is expanded and unstable on Huntington's disease chromosomes," Mar. 1993, Cell, 1993, 72:971-983.
Miao et al., "Sulforaphane prevention of diabetes-induced aortic damage was associated with the up-regulation of Nrf2 and its down-stream antioxidants," Nutr. Metab., Sep. 2012, 9(1):84.
Moller, "Neuroinflammation in Huntington's disease," J. Neural. Transm, 2010, 117:1001-1008.
Neves et al., "Docking and scoring with ICM: the benchmarking results and strategies for improvement," Journal of Computer-Aided Molecular Design, Jun. 2012, 26(6):675-686.
Neymotin et al., "Neuroprotective effect of Nrf2/ARE activators, CDDO ethylamide and CDDO trifluoroethylamide, in a mouse model of amyotrophic lateral sclerosis," Free Radic. Biol. Med., Jul. 2011, 51(1):88-96.
Outeiro et al., "Sirtuin2 inhibitors rescue alpha-synuclein-mediated toxicity in models of Parkinson's disease," Science, Jul. 2007, 317:516-519.
Pallos et al "Inhibition of specific HD A Cs and sirtuins suppresses pathogenesis in a *Drosophila* model of Hungtington's disease," Human Molecular Genetics, 2008, 17(23):3767-3775.
Paupe et al., "Impaired Nuclear Nrf2 Translocation Undermines the Oxidative Stress Response in Friedreich Ataxia," PLoS One, Jan. 2009, 4(1):e4253.
Pavese et al., "Microglial activation correlates with severity in Huntington disease: a clinical and PET study," Neurology, 2006, 66:1638-1643.
Petri et al., "Nrf2/ARE Signaling Pathway: Key Mediator in Oxidative Stress and Potential Therapeutic Target in ALS," Neurology Research International, 2012, 2012: 878030.
Phillips and Fox, "BG-12 in multiple sclerosis," Semin. Neurol., Feb. 2013, 33(1):56-65.
Pizza et al., "Neuroinflamm-aging and neurodegenerative diseases: an overview," CNS & Neurological Disorders Drug Targets, Aug. 2011, 10:621-634.
Politis et al., "Microglial activation in regions related to cognitive function predicts disease onset in Huntington's disease: a multimodal imaging study," Human Brain Mapping, 2011, 32:258-270.
Poon et al., "Role of tetrabenazine for Huntington's disease-associated chorea," The Annals of Pharmacotherapy, Jun. 2010, 44:1080-1089.

(56) References Cited

OTHER PUBLICATIONS

Quintanilla and Johnson, "Role of mitochondrial dysfunction in the pathogenesis of Huntington's disease," Brain Research Bulletin, 2009, 80:242-247.
Quinti et al., "Evaluation of histone deacetylases as drug targets in Huntington's disease models. Study of HDACs in brain tissues from R6/2 and CAG 140 knock-in HD mouse models and human patients and in a neuronal HD cell model," PLoS Currents, Sep. 2010, 2: RRN1172.
Reinhart et al., "Identification of anti-inflammatory targets for Huntington's disease using a brain slice-based screening assay," Neurobiology of Disease, Jul. 2011, 43:248-256.
Ribeiro et al., "Glutathione redox cycle dysregulation in Huntington's disease knockin striatal cells," Free Radical Biology & Medicine, 2012, 53:1857-1867.
Rojo et al., "Nrf2 regulates microglial dynamics and neuroinflammation in experimental Parkinson's disease," Glia, 2010, 58(5): 588-98.
Rosen et al., "Mutations in Cu/Zn superoxide dismutase gene are associated with familial amyotrophic lateral sclerosis," Nature 362:59-62.
Ruiz et al., "Targeting the transcription factor Nrf2 to ameliorate oxidative stress and inflammation in chronic kidney disease," Kidney Int., Jun. 2013, 83(6):1029-41.
Ryu et al., "Phloroglucinol attenuates motor functional deficits in an animal model of Parkinson's disease by enhancing Nrf2 activity," PLoS One., Aug. 2013, 8(8):e71178.
Saw et al, "Impact of Nrf2 on UVB-induced skin inflammation/photoprotection and photoprotective effect of sulforaphane," Mol. Carcinog., Jun. 2011, 50(6):479-86.
Schafer et al., "Nrf2 establishes a glutathione-mediated gradient of UVB cytoprotection in the epidermis," Genes Dev., May 2010, 24(10):1045-58.
Schafer et al., "Nrf2: a central regulator of UV protection in the epidermis," Cell Cycle, Aug. 2010, 9(15):2917-8.
Schober et al., "Classic toxin-induced animal models of Parkinson's disease: 6-OHDA and MPTP," Cell Tissue Res, Oct. 2004, 318: 215-24.
Schreibelt et al., "Therapeutic potential and biological role of endogenous antioxidant enzymes in multiple sclerosis pathology," Brain Research Reviews, 2007, 56: 322-330.
Schwab et al "Inflammation in transgenic mouse models of neurodegenerative disorders," Biochimica et Biophysica Acta., Oct. 2010, 1802:889-902.
Shan et al., "Frataxin deficiency leads to defects in expression of antioxidants and Nrf2 expression in dorsal root ganglia of the Friedreich's ataxia YG8R mouse model," Antioxid Redox Signal, Nov. 2013, 19:1481-93.
Shih et al., "A small-molecule-inducible Nrf2-mediated antioxidant response provides effective prophylaxis against cerebral ischemia in vivo," J. Neurosci., Nov. 2005, 25(44):10321-35.
Shih et al., "Induction of the Nrf2-driven antioxidant response confers neuroprotection during mitochondrial stress in vivo," The Journal of biological chemistry, 2005, 280:22925-22936.
Silvestroni et al., "Distinct neuroinflammatory profile in post-mortem human Huntington's disease," Neuroreport, 2009, 20:1098-1103.
Soetikno et al., "Curcumin alleviates oxidative stress, inflammation, and renal fibrosis in remnant kidney through the Nrf2—keap1 pathway," Mol. Nutr. Food Res., Sep. 2013, 57(9):1649-59.
Son et al., "Plumbagin, a novel Nrf2/ARE activator, protects against cerebral ischemia," J. Neurochem., Mar. 2010, 112(5):1316-26.
Sorolla et al., "Protein oxidation in Huntington disease," BioFactors, 2012, 38:173-185.
Sorolla et al., "Proteomic and oxidative stress analysis in human brain samples of Huntington disease," Free Radical Biology & Medicine, 2008, 45:667-678.
Spillantini et al., "Alpha-synuclein in Lewy bodies," Nature, Aug. 1997, 388: 839-840.

Stack et al., "Triterpenoids CDDO-ethyl amide and CDDO-trifluoroethyl amide improve the behavioral phenotype and brain pathology in a transgenic mouse model of Huntington's disease," Free radical biology & medicine, Jul. 2010, 49:147-158.
Stangel and Linker, "Dimethyl fumarate (BG-12) for the treatment of multiple sclerosis," Expert Rev Clin Pharmacol, 2013, 6(4): 355-62.
Steffan et al., "Histone deacetylase inhibitors arrest polyglutamine-dependent neurodegeneration in Drosophila," Nature, Oct. 2001, 413:739-743.
Stepkowski and Kruszewski, "Molecular cross-talk between the NRF2/KEAP1 signaling pathway, autophagy, and apoptosis," Free radical biology & Medicine, 2011, 50:1186-1195.
Sykiotis and Bohmann, "Keap1/Nrf2 signaling regulates oxidative stress tolerance and lifespan in Drosophila," Dev Cell., Jan. 2008, 14(1):76-85.
Sykiotis et al., "The role of the antioxidant and longevity-promoting Nrf2 pathway in metabolic regulation," Curr. Opin. Clin. Nutr. Metab. Care, Jan. 2011, 14(1):41-8.
Tai et al., "Imaging microglial activation in Huntington's disease. Brain research bulletin," 2007, 72:148-151.
TECFIDERA® (dimethyl fumarate) delayed-release capsules, for oral use, Biogen Inc., Prescribing Information; revised Feb. 2016, 17 pages.
Thornalley and Rabbani, "Dietary and synthetic activators of the antistress gene response in treatment of renal disease," J. Ren. Nutr., Jan. 2012, 22(1):195-202.
Tong et al., "Different electrostatic potentials define ETGE and DLG motifs as hinge and latch in oxidative stress response," Molecular and Cellular Biology, 2007, 27:7511-7521.
Tong et al., "Two-site substrate recognition model for the Keap 1-Nrf2 system: a hinge and latch mechanism," Biological Chemistry, 2006, 387:1311-1320.
Totrov and Abagyan, "Flexible protein-ligand docking by global energy optimization in internal coordinates," Proteins Suppl, 1997, 1:215-220.
Totrov and Abagyan, "Rapid boundary element solvation electrostatics calculations in folding simulations: successful folding of a 23-residue peptide," Biopolymers, 2001, 60:124-133.
Trinh et al., "Induction of the Phase II Detoxification Pathway Suppresses Neuron Loss in Drosophila Models of Parkinson's Disease," J. Neurosci., Jan. 2008, 28: 465-472.
Tsunemi et al., "PGC-1alpha rescues Huntington's disease proteotoxicity by preventing oxidative stress and promoting TFEB function," Science Translational Medicine, Jul. 2012, 4:142ra197.
Tsvetkov et al, "Proteostasis of polyglutamine varies among neurons and predicts neurodegeneration," Nat. Chem. Biol., Jul. 2013, 9:586-592.
Tufekci et al., "The Nrf2/ARE Pathway: A Promising Target to Counteract Mitochondrial Dysfunction in Parkinson's Disease," Parkinson's Disease, 2011, 2011: 314082.
Uruno et al., "The Keap1-Nrf2 System Prevents Onset of Diabetes Mellitus," Mol. Cell Biol., Aug. 2013, 33(15):2996-3010.
Valencia et al., "Elevated NADPH oxidase activity contributes to oxidative stress and cell death in Huntington's disease," Human Molecular Genetics, 2013, 22:1112-1131.
Van der Zee et al., "Rare mutations in SQSTM1 modify susceptibility to frontotemporal lobar degeneration," Acta Nueropathol., 2014, 128: 397-410.
Van Muiswinkel and Kuiperij, "The Nrf2-ARE Signalling Pathway: Promising Drug Target to Combat Oxidative Stress in Neurodegenerative Disorders," Current Drug Targets, Jun. 2005, 4: 267-281.
Vargas et al., "Absence of Nrf2 or its selective overexpression in neurons and muscle does not affect survival in ALS-linked mutant hSOD1 mouse models," PLoS One, 2013, 8(2): e56625.
Vargas et al., "Nrf2 Activation in Astrocytes Protects against Neurodegeneration in Mouse Models of Familial Amyotrophic Lateral Sclerosis," J. Neurosci., Dec. 2008, 28(50):13574-81.
Varma et al., "Inhibitors of metabolism rescue cell death in Huntington's disease models," PNAS, Sep. 2007, 104:14525-14530.

(56) References Cited

OTHER PUBLICATIONS

Williamson et al., "Activation of the Nrf2-ARE pathway by siRNA knockdown of Keap1 reduces oxidative stress and provides partial protection from MPTP-mediated neurotoxicity," Neurotoxicology, 2012, 33(30): 272-9.

Yang et al., "Curcumin upregulates transcription factor Nrf2, HO-1 expression and protects rat brains against focal ischemia," Brain Res., Jul. 2009, 1282:133-41.

Yoshida, "Amyotrophic lateral sclerosis with dementia: The clinicopathological spectrum," Neuropathy, 2004, 24: 87-102.

Yu et al., "Role of nuclear factor (erythroid-derived 2)-like 2 in metabolic homeostasis and insulin action: A novel opportunity for diabetes treatment?," World J. Diabetes., Jan. 2012, 3(1):19-28.

Zadori et al., "Mitochondrial disturbances, excitotoxicity, neuroinflammation and kynurenines: novel therapeutic strategies for neurodegenerative disorders," J Neural Sci., 2012, 322:187-191.

Zhong et al., "Transcription Factor Nrf2-Mediated Antioxidant Defense System in the Development of Diabetic Retinopathy," Invest Ophthalmol Vis. Sci., Jun. 2013, 54(6):3941-8.

\* cited by examiner

| | | Case III | Case II | Case I |
|---|---|---|---|---|
| Top Canonical Pathways | NRF2-meditated Oxidative Stress Response Pathway | ABCC4 GSTP1 AOX1 GSTT2/GSTT2B CAT HERPUD1 DNAJA4 HMOX1 DNAJB9 KEAP1 FOSL1 MAFF GCLC MGST1 GCLM MGST2 GSR NQO1 GSTA3 SQSTM1 GSTM5 TXNRD1 | ABCC4 HMOX1 ACTA2 JUNB AOX1 KEAP1 CAT KRAS DNAJA1 MAFF DNAJA4 MGST1 DNAJC15 MGST2 FOSL1 MGST3 GCLC NQO1 GCLM PIK3CD GSR PRKCD GSTA2 PRKCH GSTA3 PRKCZ GSTA4 SOD2 GSTM1 SQSTM1 GSTP1 TXNRD1 | ACTA2 FOSL1 ACTC1 GSTA3 CAT GSTA4 DNAJA1 GSTT2/GSTT2B DNAJB12 JUNB DNAJC15 KRAS DNAJC21 MAF DNAJC14 PRKCH ENC1 PRKCZ SOD2 |
| | Glutathione-mediated Detoxification | GGH GSTA3 GSTA4 GSTM5 GSTP1 GSTT2/GSTT2B MGST1 MGST2 | GSTA2 GSTA3 GSTA4 GSTM1 GSTP1 MGST1 MGST2 MGST3 | GGH GSTA3 GSTA4 GSTT2/GSTT2B |
| | LPS/IL-1 Mediated inhibition of RXR Function | ABCB1 GSTM5 ABCC4 GSTP1 ABCG1 GSTT2/GSTT2B ALAS1 HMGCS1 CAT IL1RL1 CHST2 MAOA CPT1A MGST1 GSTA3 MGST2 SULT1A3/SULT1A4 | ABCA1 GSTA2 ABCC3 GSTA3 ABCC4 GSTA4 ABCG1 GSTM1 ACOX1 GSTP1 ALAS1 HMGCS1 ALDH1A2 MAOA ALDH1A3 HS3ST6 ALDH1L1 IL1R2 ALDH1L2 MAOA ALDH3A1 MGST1 ALDH9A1 MGST2 CAT MGST3 NGFR CHST2 NR1H3 CPT1B PAPSS2 CPT1C SLC27A3 FABP5 | ACOX1 GSTA4 ALDH1A2 GSTT2/GSTT2B ALDH1A3 HMGCS1 ALDH1L1 HS3ST1 ALDH1L2 HS3ST6 ALDH1L3 IL33 ALDH6A1 IL1RL1 ALDH9A1 MAOA CAT NGFR CD14 NR1H3 CPT1C PAPSS2 FABP5 RXRA GSTA3 SLC27A3 |
| | Aryl Hydrocarbon Receptor Signaling | CYP1A1 GSTT2/GSTT2B CYP1B1 IL6 FAS MGST5 GSTA3 MGST2 GSTM5 MYC GSTP1 NFIB NQO1 | ALDH1A2 GSTM1 ALDH1A3 GSTP1 ALDH1L1 HSPB1 ALDH1L2 IL6 ALDH3A1 MGST1 ALDH9A1 MGST2 APAF1 MGST3 CCND1 NFIA CCND3 NQO1 CYP1A1 NR2F1 CYP1B1 RARB GSTA2 RARG GSTA3 RXRB GSTA4 TGFB3 | ALDH1A2 HSPB1 ALDH1A3 IL6 ALDH1L1 MYC ALDH1L2 NFIA ALDH3A1 NFIC ALDH6A1 NR2F1 ALDH9A1 RARB CCND1 RARG CYP1A1 RXRA FAS RXRB GSTA3 SRC GSTA4 TGFB2 GSTT2/GSTT2B TGFB3 |
| | Xenobiotic Metabolism Signaling | ABCB1 GSTT2/GSTT2B CAT HMOX1 CHST2 IL6 CYP1A1 KEAP1 CYP1B1 MAOA GCLC MGST1 GSTA3 MGST2 GSTM5 NQO1 GSTP1 SULT1A3/SULT1A4 | ABCC3 HMOX1 ALDH1A2 HS3ST1 ALDH1A3 HS3ST6 ALDH1L1 IL6 ALDH1L2 KEAP1 ALDH3A1 KRAS ALDH9A1 MAOA CAMK2B MGST1 CAT MGST2 CHST2 MGST3 CYP1A1 NQO1 CYP1B1 PIK3CD GCLC PPM1L GRIP1 PPP2CB GSTA2 PPP2R2B GSTA3 PRKCD GSTA4 PRKCH GSTM1 PRKCZ GSTP1 UGT1A1 | ALDH1A2 GSTA4 ALDH1A3 GSTT2/GSTT2B ALDH1L1 HS3ST1 ALDH1L2 HS3ST6 ALDH9A1 IL6 ALDH6A1 KRAS ALDH9A1 MAF CAMK2B MAOA CAT MAP3K3 CITED2 PPP2CB CYP1A1 PPP2R2B GRIP1 PRKCH GSTA3 PRKCZ RXRA |
| | Glutathione Redox Reactions I | GPX1 GSR MGST1 MGST2 | GPX7 GPX8 GPX1 GSR MGST1 MGST2 MGST3 | |
| | Glutathione Biosynthesis | GCLC GCLM | GCLC GCLM | |

FIG. 5B

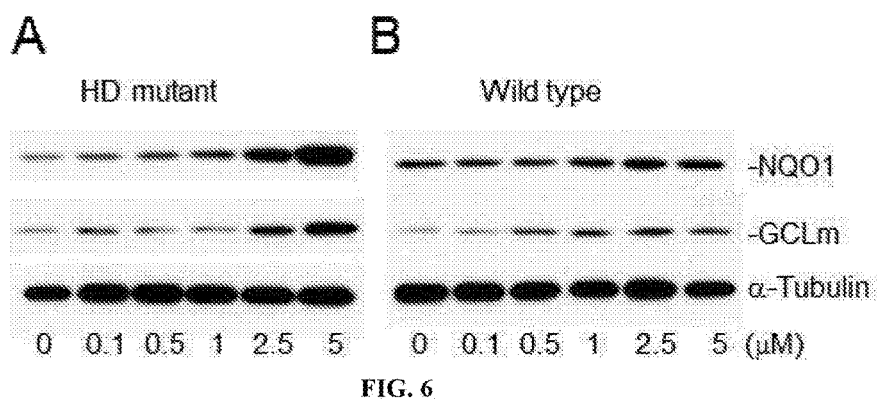

FIG. 6

A
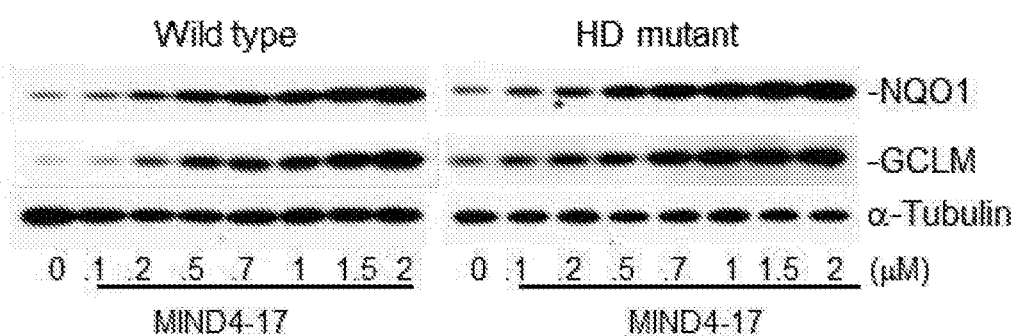
B
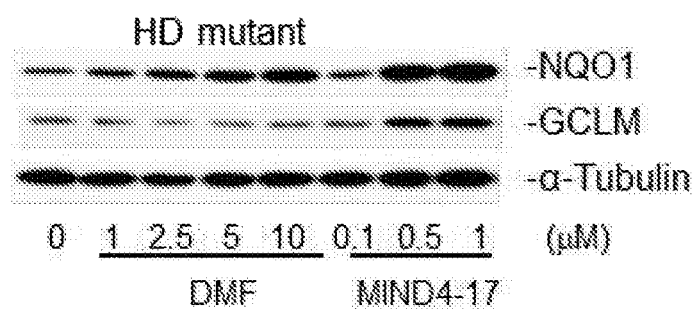
FIG. 10

FIG. 11B
FIG. 11C
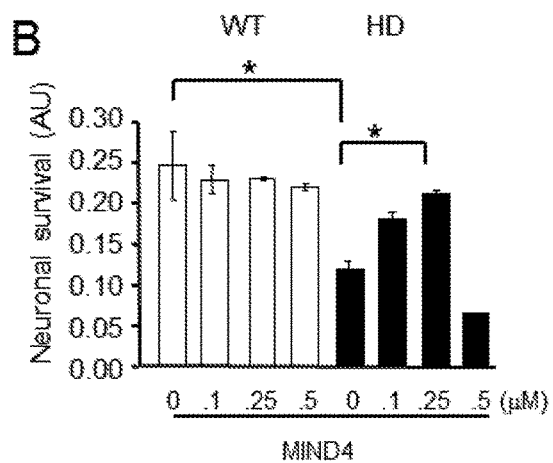
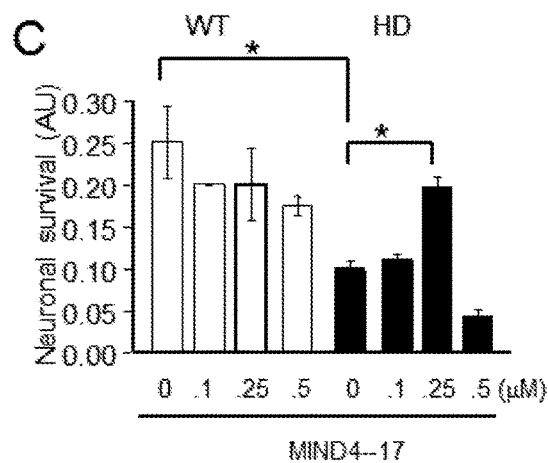

Effects of MIND4 and MIND4A on enhancing degradation (clearance) of misfolded huntingtin (HTT) fragments A    Effects of MIND4 on HTT clearance in HD mutant and wild type ST14A after 6hr

B    Effects of MIND4 on HTT clearance in HD mutant and wild type ST14A after 6hr

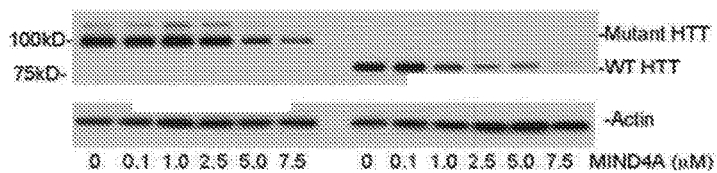

C    Effects of MIND4 on clearance of mutant exon 1 HTT fragment in cortex of symptomatic 10-week old HD mice R6/2 ( description of the drug trial is disclosed in submitted manuscript)

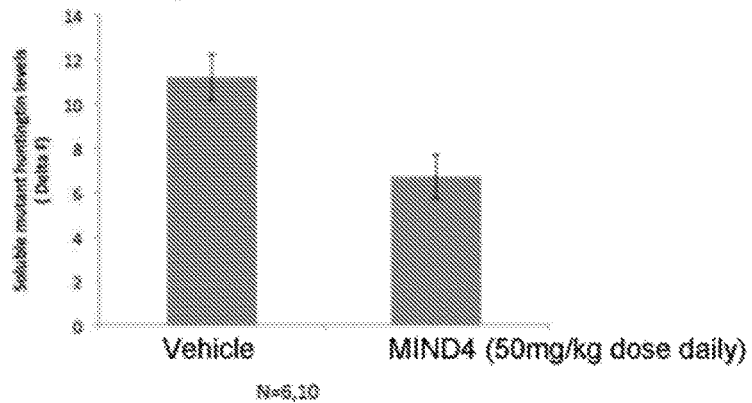

FIG. 17

SMALL MOLECULE ACTIVATORS OF NRF2 PATHWAY

CROSS-REFERENCE TO RELATED APPLICATIONS

This application is a U.S. National Phase Application under 35 U.S.C. §371 of International Patent Application No. PCT/US2014/041335, filed on Jun. 6, 2014, which claims priority to U.S. Provisional Application Ser. No. 61/832,319, filed Jun. 7, 2013, and 61/886,970, filed Oct. 4, 2013, all of which are incorporated by reference in their entireties.

FEDERALLY SPONSORED RESEARCH OR DEVELOPMENT

This invention was made with Government support under Grant No. U01NS069912 awarded by the National Institutes of Health. The Government has certain rights in the invention.

TECHNICAL FIELD

This disclosure relates to compounds that act as activators of the NRF2/KEAP1/ARE pathway. Such compounds are useful in the treatment of a variety of diseases including Huntington's disease, Parkinson's disease, Alzheimer's disease, inflammation, and cancer.

BACKGROUND

The activity of transcriptional factor NRF2 (nuclear factor (erythroid-derived 2)-like 2) is tightly regulated by the cytoplasmic inhibitor KEAP1 (Kelch-like ECH associated protein 1), which acts as an adaptor protein for Cul3-based ubiquitin E3 ligase complex (Joshi and Johnson, 2012; Jung and Kwak, 2010; Tong et al., 2006). KEAP1 (iNRF2) is a cysteine-rich protein that serves as a redox sensor in cells. Under stress conditions, such as an increase of reactive oxygen species (ROS), a group of KEAP1 cysteines are oxidatively modified and the resulting conformational change protects NRF2 from KEAP1-directed degradation (Tong et al., 2007). When NRF2 accumulates in the cytosol to levels that surpass the endogenous sequestration capacity of KEAP1, the excess NRF2 translocates to the nucleus, binds to antioxidant response elements (AREs) in the promoter of target genes, and activates broadly protective responses (Kensler et al., 2007; Lee et al., 2003).

Activation of the NRF2 pathway appears to be impacted in Huntington Disease (HD) systems, based on the findings of altered levels of downstream targets of NRF2 in HD brain (Sorolla et al., 2008), reduced NRF2 activity in HD cell lines (Jin et al., 2013) and neuroprotective effects following NRF2 overexpression (Tsevtkov et al, Nat. Chem. Biol. Jul. 21, 2013 in press). Several upstream signal transduction pathways, including MAPK/ERK/JNK and PI3K regulate NRF2 activation (Cheung et al., 2013) and have been implicated in HD (Apostol et al., 2006). These upstream pathways, stimulated by oxidative stress, phosphorylate NRF2, preventing KEAP1/CUL3 complex from mediating Ub-proteosome degradation (Cullinan et al., 2004).

SUMMARY

Activation of cellular responses through the NRF2/KEAP1/ARE pathway is a promising therapeutic strategy to counter neurodegeneration. Provided herein are compounds which induce canonical NRF2-dependent responses and have neuroprotective properties. In accord with the known anti-inflammatory effects of NRF2 activation, the compounds provided herein, repress expression of inflammatory markers and reduce levels of TNFα demonstrating the neuroprotective anti-inflammatory potential of NRF2 activator in the CNS. In addition, the compounds provided herein are high affinity reversible binders of the NRF2 inhibitor, KEAP1. These compounds can therefore be used in the treatment of a number of diseases, including Huntington's disease, Parkinson's disease, Alzheimer's disease, inflammation, and cancer.

The compounds provided herein include:

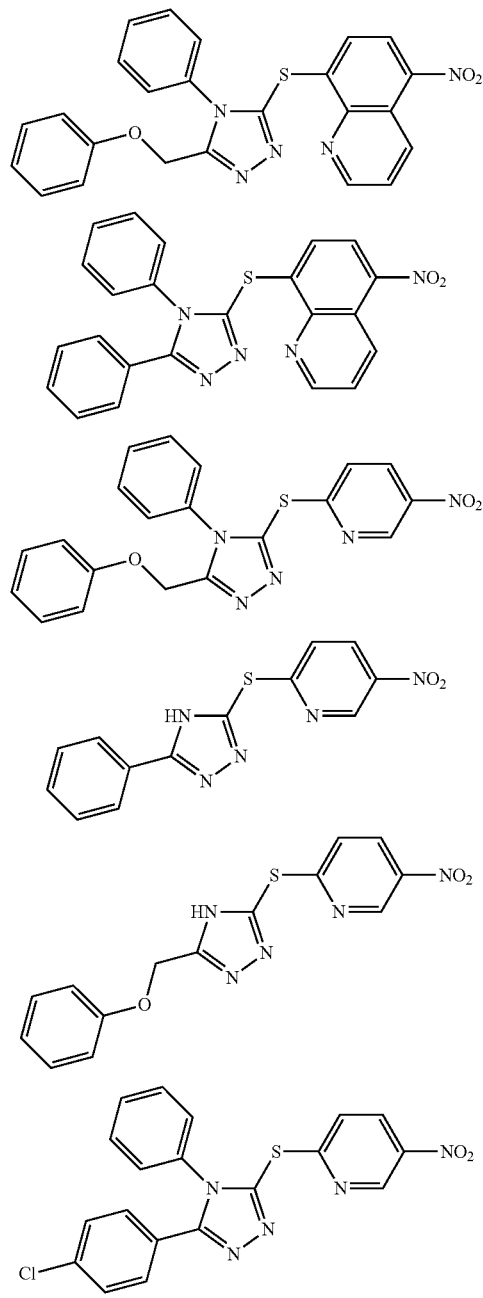

-continued
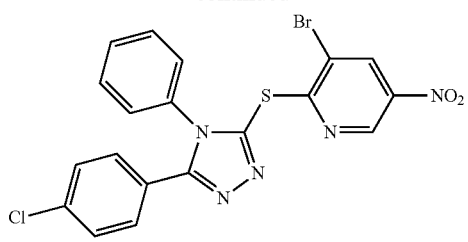
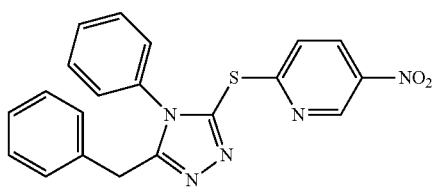
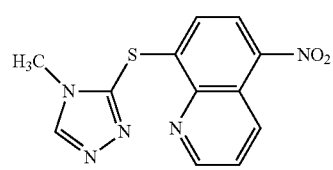
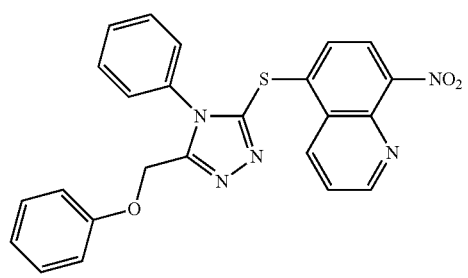
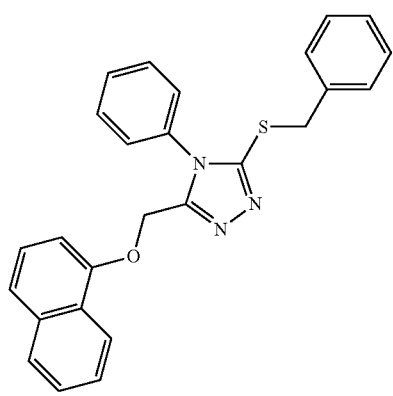
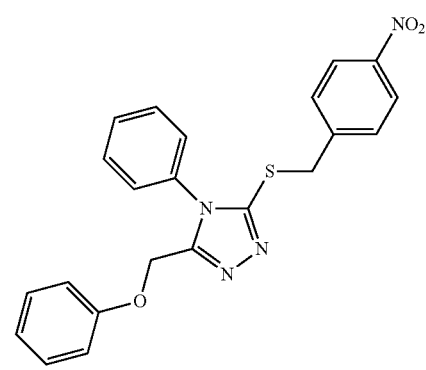
-continued
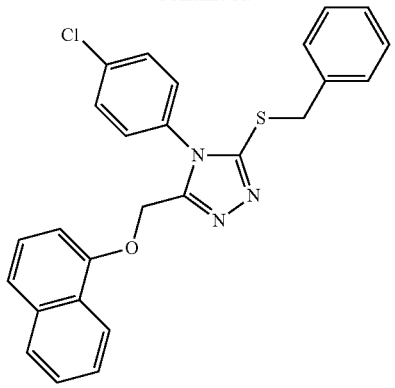
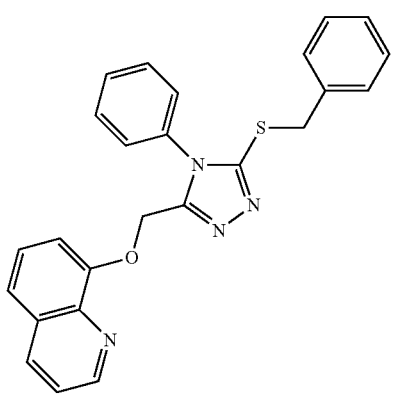
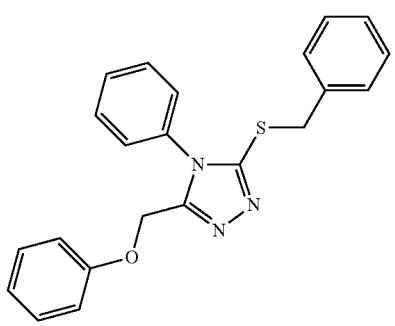
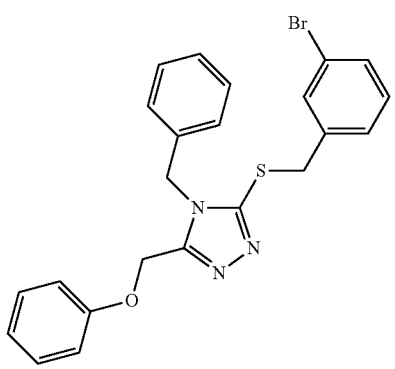

-continued

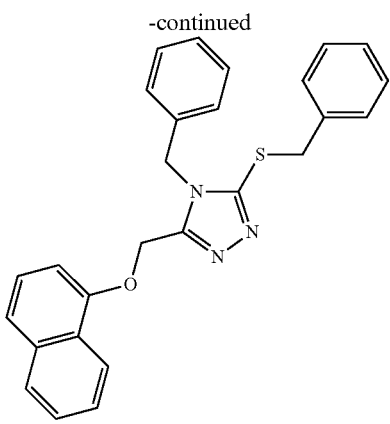

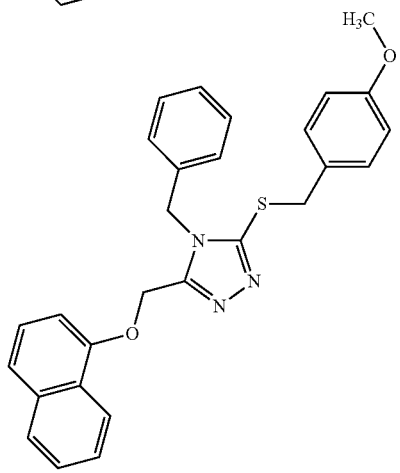

or a pharmaceutically acceptable salt thereof. In some embodiments, a compound provided herein is

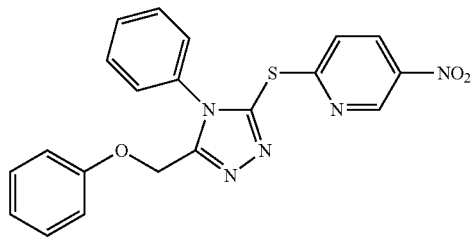 [SMILES: O=[N+]([O-])c1ccc(Sc2nnc(COc3ccccc3)n2-c2ccccc2)nc1]

or a pharmaceutically acceptable salt thereof.

Provided herein is a method for treating a neurodegenerative disorder in a subject, the method comprising administering to the subject a therapeutically effective amount of a compound provided herein, or a pharmaceutically acceptable salt thereof. For example, a neurodegenerative disorder can be selected from Alzheimer's disease (AD), Parkinson's disease (PD), Huntington disease (HD) and other CAG-triplet repeat (or polyglutamine) diseases, amyotrophic lateral sclerosis (ALS; Lou Gehrig's disease), diffuse Lewy body disease, chorea-acanthocytosis, primary lateral sclerosis, multiple sclerosis (MS), frontotemporal dementia, Friedreich's ataxia, and epilepsy (repression of microglia activation). In some embodiments, the neurodegenerative disorder is selected from the group consisting of: Alzheimer's disease (AD), Parkinson's disease (PD), Huntington disease (HD), amyotrophic lateral sclerosis (ALS; Lou Gehrig's disease); and multiple sclerosis (MS).

Also provided herein is a method for treating an inflammatory disease in a subject, the method comprising administering to the subject a therapeutically effective amount of a compound provided herein, or a pharmaceutically acceptable salt thereof. In some embodiments, the inflammatory disease is a chronic condition. For example, the inflammatory disease can include chronic cholecystitis, bronchiectasis, aortic valve stenosis, restenosis, psoriasis, chronic obstructive pulmonary disorder (COPD), inflammatory uveitis, atherosclerosis, and arthritis. In some embodiments, the inflammatory disease is psoriasis. In some embodiments, the inflammatory disease is an acute condition. For example, the inflammatory disease can include bronchitis, conjunctivitis, pancreatitis, chronic kidney diseases (CDKs), diabetes (induced inflammation), ischemia, and stroke.

Further provided herein is a method for treating inflammation in a subject, the method comprising administering to the subject a therapeutically effective amount of a compound provided herein, or a pharmaceutically acceptable salt thereof.

The compounds provided herein can also be used to promote survival of a eukaryotic cell (e.g., a mammalian cell). The method can include administering to the subject a therapeutically effective amount of a compound provided herein, or a pharmaceutically acceptable salt thereof. The method can be useful to increase the lifespan of the cell or increase the cell's ability to resist stress such as heat shock, oxidative stress, osmotic stress, DNA damage, inadequate salt level, inadequate nitrogen level, or inadequate nutrient level. In some embodiments, a compound provided herein can mimic the effect of nutrient restriction on the cell.

This disclosure also provides a method for treating or preventing a disease or disorder associated with cell death or aging in a subject, the method comprising administering to the subject a therapeutically effective amount of a compound provided herein, or a pharmaceutically acceptable salt thereof. For example, the aging-related disease can include stroke, a cardiovascular disease, arthritis, high blood pressure, diabetes, or age-dependent Alzheimer's, Parkinson's, or Huntington's diseases Also provided herein is a method for treating cancer in a subject, the method comprising administering to the subject a therapeutically effective amount of a compound provided herein, or a pharmaceutically acceptable salt thereof. For example, the cancer can include prostate cancer, bladder cancer, ovarian cancer, breast cancer (e.g., breast cancer with mutated BRCA1), head and neck cancer, chronic lymphocytic leukemia, thymus cancer, hepatocellular carcinoma, colorectal cancer, colon cancer, skin cancer, pancreatic cancer, leukemia, lung cancer, glioblastoma, cervical cancer, lymphoma, and multiple myeloma. In some embodiments, the cancer is skin cancer.

The compounds provided herein can also be useful to activate a NRF2 pathway in a cell. In some embodiments, the method comprises contacting a cell with an effective amount of a compound provided herein, or a pharmaceutically acceptable salt thereof. In some embodiments, the cell is contacted in vitro or in vivo. In some embodiments, contacting the cell includes administering the compound to a subject. The subject can be a mammal (e.g., a human).

In some embodiments, the compounds provided herein can inhibit one or more sirtuins in the cell. For example, the compounds can inhibit one or more sirtuins selected from the group consisting of: SIRT1, SIRT2, SIRT3, SIRT4, SIRT5, SIRT6, and SIRT7. In some embodiments, the sirtuin is SIRT2.

Further provided herein is a method inhibiting a KEAP1 protein in a cell, the method comprising contacting a cell with an effective amount of a compound provided herein, or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A shows the dose-response inhibition of recombinant SIRT2 deacetylase activity by MIND4 as described (Outeiro et al., 2007). FIGS. 1B and 1C show dose-response tests of MIND4 activity in SIRT1 (1B) and SIRT3 (1C) biochemical deacetylation.

FIG. 2A shows the dose-dependent increase of α-tubulin acetylation at lysine K40 in mutant HD (left panel) and wild type (right panel) post-mitotic ST14a cells. Protein levels were detected by immunoblotting in extracts from cells treated for 6 hours with antibodies specific to acetylated α-tubulin and total (acetylated and non-acetylated) α-tubulin. FIG. 2B shows the quantification of α-tubulin acetylation shown in (2A). Relative increase is shown as ratio of acetylated/total levels of α-tubulin.

FIG. 3A illustrates MIND4 enhanced survival of primary cortical neurons expressing 140Q full-length mutant huntingtin from HD homozygous knock-in mice (140Q/140Q). MIND4 rescued neuronal death in HD cultures in a dose response manner over the 7 days of treatment (filled bars). No effects on control cortical neurons from wild type mice were observed (empty bars). Student's t-test *p<4.3×10$^{-14}$, **p<2.5×10$^{-8}$; N=6 wells per dose. FIG. 3B shows that MIND4 treatment protected against neurodegeneration of medium spiny neurons (MSNs) expressing mutant (73Q) N-terminus Htt fragments (mHTTex1) in rat ex vivo brain slices. Yellow fluorescent protein (YFP) was used as a neuronal viability marker and co-transfected with mHTTex1 constructs (black bars). Effects are compared with survival of neurons expressing YFP plasmid alone (open bar) and expressed as the numbers of healthy YFP-positive MSNs per brain slice. MIND4 at the indicated concentrations and the positive control pan-caspase inhibitor Boc-D-FMK at 100 µM (C$^+$, grey bar) were added directly to the tissue culture media. Statistically significant effect of MIND4 treatment was observed at 10 µM by ANOVA followed by Dunnett's post hoc comparison test at the p=0.05 confidence level. FIG. 3C illustrates the MIND4 enhanced survival of photoreceptor neurons expressing a mutant Htt exon I fragment model of HD in *Drosophila*. Relative rescue of photoreceptor neurons in flies treated vs. untreated with MIND4 at 10 µM dose was estimated as 22.6%.*=p<0.001. FIG. 3D shows MIND4 effects on known SIRT2 substrates α-tubulin K40 and histone H3 K56 in wild type primary cortical neurons (DIV11). Neurons were treated with MIND4 for 6 hours and proteins levels analyzed by immunoblotting. Total α-tubulin and histone H3 levels were used as control. Expression of full-length SIRT2 protein (SIRT2.1 isoform) was predominant.

FIG. 4 provides gene expression profiling and IPA analysis that reveal NRF2 as the major pathway impacted by MIND4 in mutant HTT-expressing cells (Case III).

FIG. 5 provides the canonical Pathways and differential gene expression analysis of all three Cases I-III. FIG. 5B provides the statistically significant genes in each Case for the Top Canonical Pathways found in Case III. Genes highlighted in Red are upregulated; genes highlighted in Green are downregulated.

FIGS. 6A-B shows MIND4 induces expression of major NRF2-responsive proteins NQO1 and GCLM in differentiated HD mutant (6A) and wild type (6B) ST14A cells. Cells were treated with MIND4 for 24 hours at the indicated doses. MIND4 increased levels of NRF2-reponsive proteins in a dose-dependent manner as detected by immunoblotting with NQO1 and GCLM antibodies. Levels of α-tubulin were used as control. FIGS. 6C-F illustrates that MIND4 represses microglia activation in vitro. BV2 microglia cells were pre-incubated for 24 hr with MIND4 at 3 µM dose, followed by activation with 10 ng/ml of LPS for 2 hr. Treatment with MIND4 resulted in down-regulation of inflammatory biomarkers TNFα (6C), IL-6 (6D), IL-1β (6E), and MCP-1 (6F), measured using qRT-PCR with gene-specific primers; the effects on gene expression were assessed in duplicates.

FIG. 7A is a chromatogram of MIND4 standard (1 µg/ml); FIG. 7B is a chromatogram of MIND4-treated brain extracts. The peaks were detected in channel 3 at ~8-min retention time. HPLC analysis detected MIND4 presence in wild type mouse cortices at estimated ~0.5 µM concentration, providing preliminary evidence for compound brain permeability.

FIGS. 8A-D show that MIND4 treatment represses expression of inflammatory TNFα protein in brain of HD mouse model R6/2. FIG. 8A shows TNFα protein levels detected by immunoblotting in cortical extracts from 10-week old wild type and R6/2 mice. FIG. 8B shows TNFα protein levels detected by immunoblotting in cortical extracts from 10-week old R6/2 mice that were vehicle (mock)-treated and MIND4-treated at a daily dose of 50 mg/kg. α-Tubulin and GADPH proteins (8A-B) were used as loading control. FIG. 8C shows quantification analysis of TNFα levels (8C) in wild type (open bars) and in R6/2 (black bars) brain samples. FIG. 8D shows quantification analysis of TNFα levels (8B) in vehicle-treated (black bars) and in MIND4-treated (grey bars) R6/2 brain samples. Student's t-test, *** P<0.001 Levels of α-Tubulin and GADPH proteins were used to normalize TNFα levels.

FIGS. 9A-B shows the results of tests of NRF2 activation properties of MIND4 analogs. FIG. 9A illustrates the dose-response induction of NQO1 protein in differentiated ST14A cells treated with MIND4 and MIND4A compounds at indicated concentrations. FIG. 9B illustrates the dose-response induction of NQO1 and GCLM proteins in differentiated ST14A cells treated with MIND4-17, MIND4-17C, and MIND4C. Levels of α-tubulin (9A-B) were used as loading control. FIGS. 9C-D show the results of dose-response tests on MIND4A (9C) and MIND4-17 (9D) analogs in biochemical SIRT2 deacetylation assay. Each dose was tested in triplicates.

FIG. 10 shows the evaluation of NRF2-activating properties of MIND4-17 structural analog. FIG. 10A illustrates the MIND4-17 dose-dependent induction of NRF2-responsive proteins NQO1 and GCLM in differentiated HD and wild type ST14A cells. FIG. 10B illustrates the dose-dependent induction of NQO1 protein in HD mutant cells treated with dimethyl fumarate (DMF) and MIND4-17.

FIGS. 11B-C show the effects of MIND4 (11B) and MIND4-17 (11C) treatments on wild type (white bars) and 140CAG full-length HTT mutant (black bars) primary neurons. Cell survival was measured as MTT transformation at 10 days in vitro (DIV). Neurons were treated three times with the compounds at 4, 6 and 8 DIV with the indicated concentrations. *=p<0.001.

FIG. 14A shows the structure of KEAP1 protein interaction with NRF2 loop. The representation of the KEAP1 pocket is based on a complex structure PDB code 2flu (Experimental Procedures). The NRF2 loop is shown in magenta. The upper cup-shaped cavity of the KEAP1 pocket is separated from the lower cylindrical cavity by a bottleneck in closed conformation; Arg415 is shown by arrow. FIG. 14B shows that Arg415 (R415) is a "flexible" gatekeeper within the bottleneck, separating upper and lower cavities of KEAP1. FIG. 14C illustrates the docked position of MIND4 in the KEAP1 pocket. Ligand adapts a low energy stable conformation, which is consistent with a high affinity binding to the upper cavity of the KEAP1 pocket (ligand nitrogen and oxygen groups are shown in red and blue respectively; hydrogen bonds are shown as dotted lines). The ligand nitrogen group forms hydrogen bonds with Arg 483 (R483) of KEAP1. The re-arranged position of Arg 415 (R415) is shown. FIGS. 14D-E show the docked position of MIND4-17 in a relaxed conformation of the KEAP1 pocket. MIND4-17 in relaxed extended conformation is nearly perfectly complementary to ligand-induced new cavity within the KEAP1 bottleneck, induced by ligand re-arrangement of flexible Arg 415 side chain.

FIGS. 17A-C illustrate the effects of MIND4 and MIND4A on enhancing degradation (clearance) of misfolded huntingtin (HTT) fragments.

FIG. 19A) MIND4 dose-dependent induction of Nrf2-responsive proteins NQO1 and GCLM in wild type and mutant SOD1 (G93A) mutant mouse primary astroglia. FIG. 19B) MIND4-17 dose-dependent induction of Nrf2-responsive proteins NQO1 and GCLM in wild type and mutant SOD1 (G93A) mutant mouse primary astroglia cells. Levels of the astrocyte marker GFAP are shown as control.

DETAILED DESCRIPTION

Figure 1:
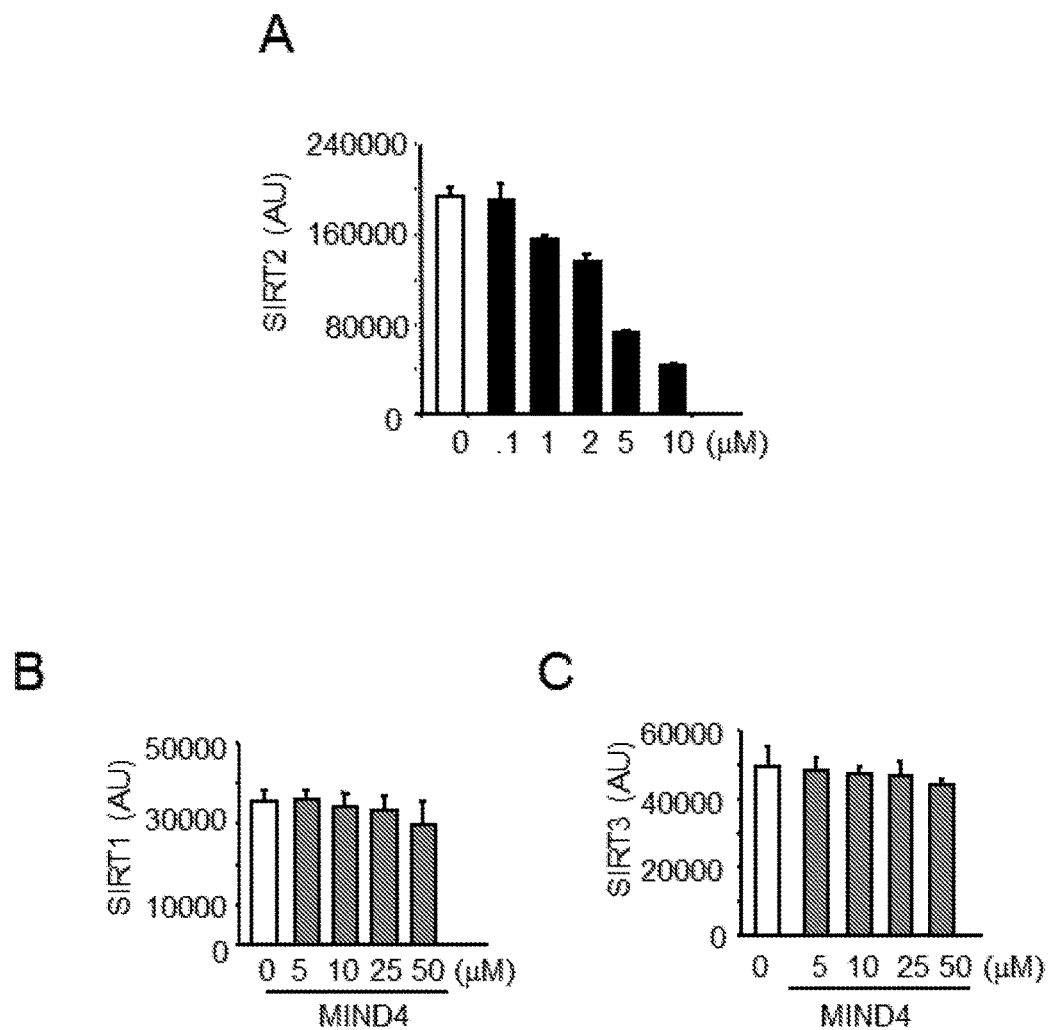
FIG. 1 illustrates the properties of MIND4 as inhibitor of SIRT2 deacetylase.

Activation of cellular responses through the NRF2/KEAP1/ARE pathway is a promising therapeutic strategy to counter neurodegeneration. Provided herein are compounds which induce canonical NRF2-dependent responses and have neuroprotective properties. In accord with the known anti-inflammatory effects of NRF2 activation, the compounds provided herein, repress expression of inflammatory markers and reduce levels of TNFα demonstrating the neuroprotective anti-inflammatory potential of NRF2 activator in the CNS. In addition, the compounds provided herein are high affinity reversible binders of the NRF2 inhibitor, KEAP1. These compounds can therefore be used in the treatment of a number of diseases, including Huntington's disease, Parkinson's disease, Alzheimer's disease, inflammation, and cancer.

The compounds provided herein include:

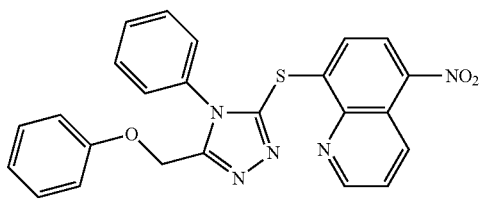

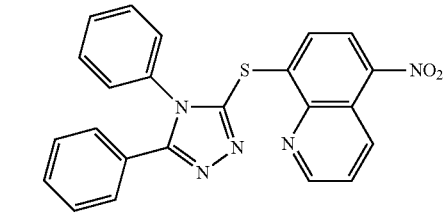

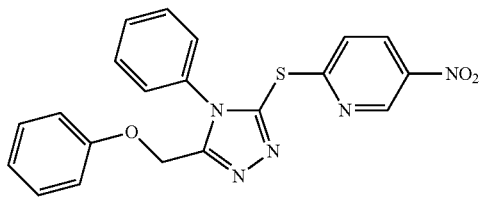

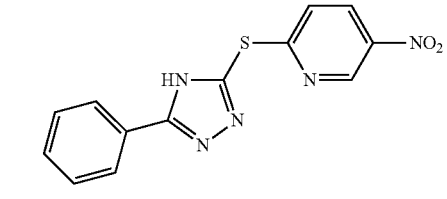

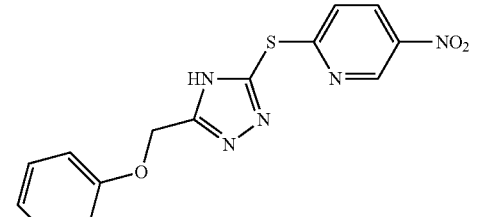

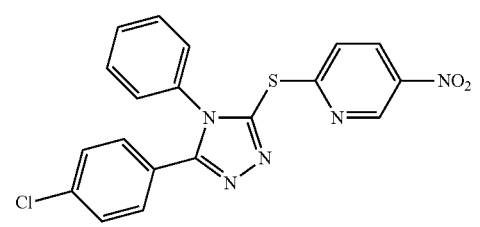

-continued

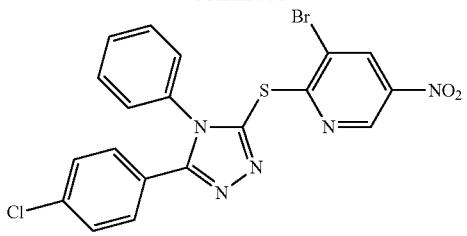

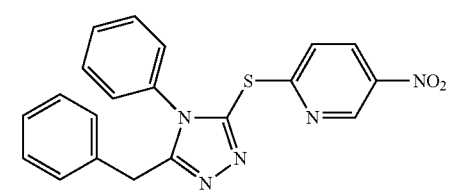

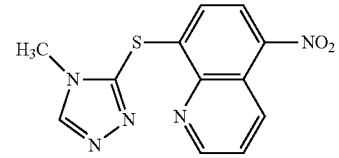

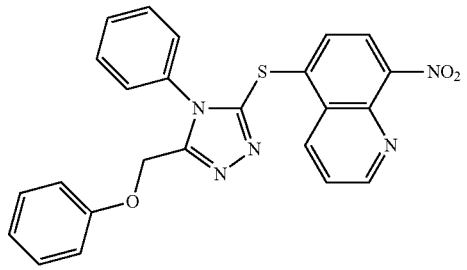

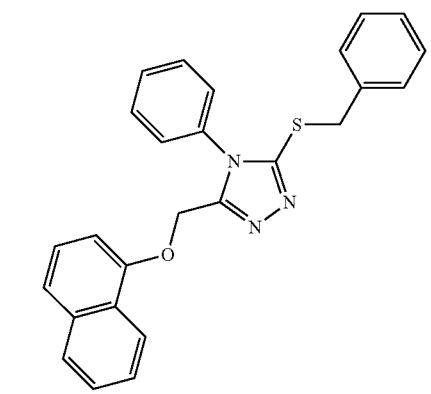

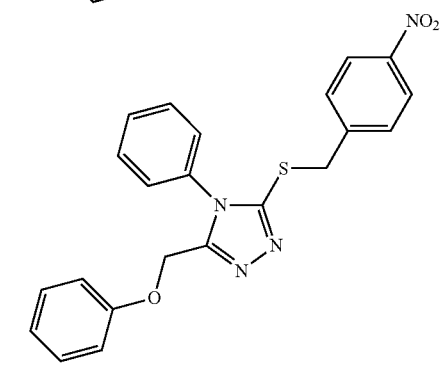

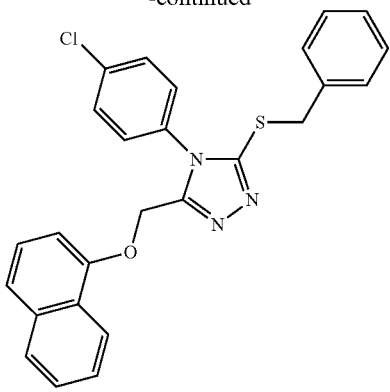
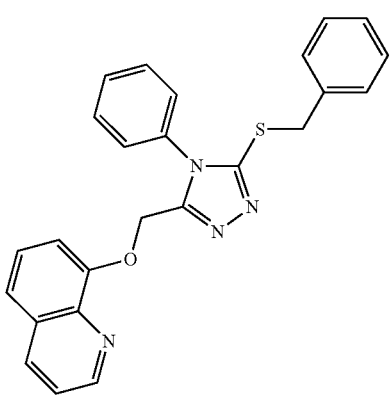
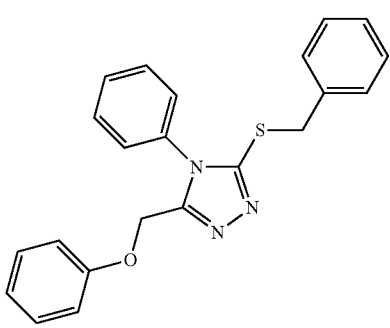
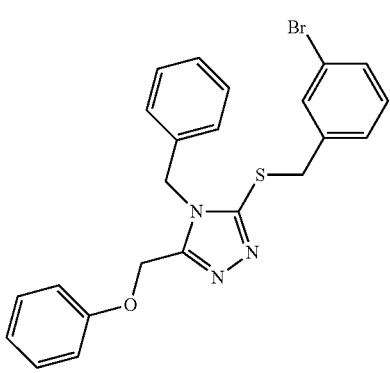
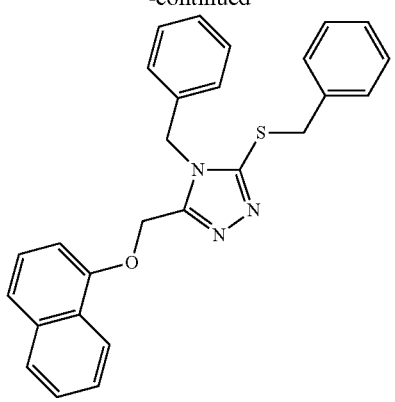
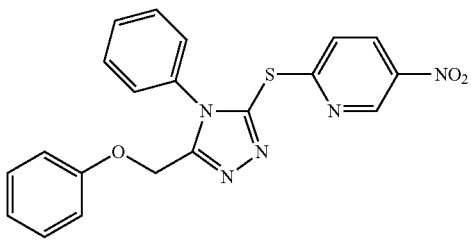
or a pharmaceutically acceptable salt thereof. In some embodiments, the compounds can include:
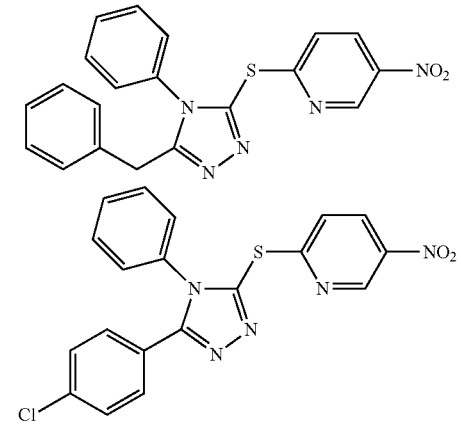
or a pharmaceutically acceptable salt thereof.

The compounds provided herein can be synthesized using conventional techniques using readily available starting materials or the compounds may be purchased from commercial providers.

The methods described herein include methods for the treatment of disorders associated with the NRF2/KEAP1/ARE pathway. In some embodiments, the disorder is a neurodegenerative disorder, an inflammatory disease, inflammation, cancer, or a disorder associated with cell-death and/or ageing. Generally, the methods include administering a therapeutically effective amount of a compound as described herein, to a subject who is in need of, or who has been determined to be in need of, such treatment.

As used in this context, to "treat" means to ameliorate at least one symptom of the disorder associated with the NRF2/KEAP1/ARE pathway.

In some embodiments, the compounds provided herein can be used to treat a neurodegenerative disorder in a subject. For example, the neurodegenerative disorder can be include Alzheimer's disease (AD), Parkinson's disease (PD), Huntington disease (HD) and other CAG-triplet repeat (or polyglutamine) diseases, amyotrophic lateral sclerosis (ALS; Lou Gehrig's disease), diffuse Lewy body disease, chorea-acanthocytosis, primary lateral sclerosis, multiple sclerosis (MS), frontotemporal dementia, Friedreich's ataxia, and epilepsy (repression of microglia activation). In some embodiments, the neurodegenerative disorder includes PD, AD, HD, ALS, and MS.

Huntington's disease (HD), for example, is an autosomal dominant and highly penetrant neurodegenerative disorder, resulting from the pathological expansion of a polymorphic trinucleotide repeat sequence $(CAG)_n$ within a gene encoding the large, highly conserved protein, Huntingtin (HTT). Brains from HD patients typically display marked striatal and cortical atrophy at the time of diagnosis (Hersch and Rosas, 2008; Killoran and Biglan, 2012). Once motor or other symptoms become apparent, typically during mid-life, affected individuals become increasingly disabled over the course of 15-25 years before succumbing to the effects of severe physical and mental deterioration. The only FDA approved therapeutic for HD, tetrabenazine, is solely palliative and counters HD-associated involuntary movements (chorea) (Poon et al., 2010).

Activation of the NRF2 pathway appears to be impacted in HD systems (and other CAG-triplet repeat (or polyglutamine) diseases), based on the findings of altered levels of downstream targets of NRF2 in HD brain (Sorolla et al., 2008), reduced NRF2 activity in HD cell lines (Jin et al., 2013) and neuroprotective effects following NRF2 overexpression (Tsevtkov et al, Nat. Chem. Biol. Jul. 21, 2013 in press). Several upstream signal transduction pathways, including MAPK/ERK/JNK and PI3K regulate NRF2 activation (Cheung et al., 2013) and are implicated in HD (Apostol et al., 2006), providing further support for modulation of NRF2 activity as a promising therapeutic target. These upstream pathways, stimulated by oxidative stress, phosphorylate NRF2, preventing KEAP1/CUL3 complex from mediating Ub-proteosome degradation (Cullinan et al., 2004). Finally, the protective benefit of pharmacological stimulation of NRF2 signaling in HD mice with fumaric acid esters and triterpenoids, which mimic the effects of oxidative stress and modify the cysteine residues in KEAP1, also support the relevance of this therapeutic target (Ellrichmann et al., 2011; Stack et al., 2010).

Complex pathogenic mechanisms have been implicated in Huntington's disease, including excess oxidative stress and neuroinflammation, which are also implicated in other age-dependent neurodegenerative disorders such as the highly prevalent Alzheimer's and Parkinson's diseases (Moller, 2010; Quintanilla and Johnson, 2009; Zadori et al., 2012). For instance, oxidative stress has been described in both HD patients and in experimental models (Browne and Beal, 2006; Sorolla et al.), potentially due to inherent properties of neurons that may make them highly susceptible to the consequences of this type of stress (Johri and Beal, 2012). The mechanisms underlying increased oxidative stress in HD are not yet clear, but may include increased NADPH activity (Valencia et al., 2013), dysregulated glutathione homeostasis (Li et al., 2012; Ribeiro et al., 2012) and impaired PGC1α-mediated transcription (Tsunemi et al., 2012). See also, for example, Ellrichmann G et al., *PLoS One.* 2011 Jan. 31; 6(1):e16172; Chaturvedi R K et al., *Hum Mol Genet.* 2010 Aug. 15; 19(16):3190-205; Stack C et al., *Free Radic Biol Med.* 2010 Jul. 15; 49(2):147-58;

In some embodiments, the neurodegenerative disorder is Alzheimer's disease. The link between the NRF2 signaling pathway and the treatment of Alzheimer's disease has been exemplified in a number of publications, including, for example, Li X H et al., *Neurosci Lett.* 2012 Apr. 11; 514(1):46-50; Kanninen K et al., *J Proc Natl Acad Sci USA.* 2009 Sep. 22; 106(38):16505-10; and Kanninen K et al., *J. Mol Cell Neurosci.* 2008 November; 39(3):302-13.

In the case of Parkinson's disease (PD), overexpression of NRF2 has been correlated with a delay in motor pathology and synuclein aggregation throughout the CNS in a number of models. See, for example, Du X et al., *Neurotox Res.* 2013 July; 24(1):71-9; Gan L et al., *J Neurosci.* 2012 Dec. 5; 32(49):17775-871 Li R et al., *Brain Res.* 2013 Jul. 26; 1523:1-9; Gunjima K et al., *Cell Biochem.* 2013 Aug. 19. doi: 10.1002/jcb.24643; Ryu J et al., *PLoS One.* 2013 Aug. 20; 8(8):e71178. doi: 10.1371/journal.pone.0071178.

Neuroprotective effects of NRF2 activators have been identified in models of amyotrophic lateral sclerosis (ALS; Lou Gehrig's disease). See, for example, Vargas M R et al., *J Neurosci.* 2008 Dec. 10; 28(50):13574-81; and Neymotin A et al., *Free Radic Biol Med.* 2011 Jul. 1; 51(1):88-96. Such effects have also been identified in epileptic models. See, for example, Mazzuferi M et al., *Ann Neurol.* 2013 May 20. doi: 10.1002/ana.23940.

In some embodiments, the neurodegenerative disorder is multiple sclerosis (MS). The therapeutic potential and role of endogenous antioxidant enzymes in the treatment of MS has been shown in numerous studies. See, for example, Schreibelt G et al., *Brain Res Rev.* 2007 December; 56(2): 322-30; Phillips J T and Fox R J. *Semin Neurol.* 2013 February; 33(1):56-65; and Lee D H et al., *Int J Mol Sci.* 2012; 13(9):11783-803.

In the case of Friedreich's ataxia, this particular disorder has been found to lead to reduced expression and impaired translocation of NRF2. See, for example, D'Oria V et al., *Int J Mol Sci.* 2013 Apr. 10; 14(4):7853-65; Shan Y et al., *Antioxid Redox Signal.* 2013 Mar. 28. [Epub ahead of print]; and Paupe V et al., *PLoS One.* 2009; 4(1):e4253.

The compounds provided herein are also useful in the treatment of inflammatory diseases in a subject. For example, both chronic and acute inflammatory conditions can be ameliorated with administration of a therapeutically effective amount of one or more compounds as provided herein. In some embodiments, the inflammatory disease is a chronic condition such as, for example, chronic cholecystitis, bronchiectasis, aortic valve stenosis, restenosis, psoriasis, chronic obstructive pulmonary disorder (COPD), inflammatory uveitis, atherosclerosis, and arthritis. In some embodiments, the inflammatory disease is psoriasis. In some embodiments, the inflammatory disease is an acute condition such as, for example, bronchitis, conjunctivitis, pancreatitis, chronic kidney diseases (CDKs), diabetes (induced inflammation), ischemia, and stroke.

In the case of chronic kidney diseases, for example, the NRF2 pathway has been linked with amelioration of oxidative stress and inflammation. See, for example, Kim H J and Vaziri N D, *Am J Physiol Renal Physiol.* 2010 March; 298(3):F662-71; Córdova E J et al., *Lupus.* 2010 September; 19(10):1237-42; Thornalley P J and Rabbani N., *J Ren March* 2012 January; 22(1):195-202; Soetikno V et al., *Mol Nutr Food Res.* 2013 September; 57(9):1649-59; Ruiz S et al., *Kidney Int* 2013 June; 83(6):1029-41; and Lee B H et al., *Free Radic Biol Med.* 2013 July; 60:7-16.

Up-regulation of NRF2 has been associated with preventing or delaying the onset of numerous inflammatory conditions associated with diabetes, such as diabetes mellitus, diabetic retinopathy, diabetic cardiomyopathy, and diabetes-induced aortic damage. See, for example, Uruno A et al., *Mol Cell Biol.* 2013 August; 33(15):2996-3010; Castellano J M et al., *Diabetes.* 2013 June; 62(6):1791-9; Zhong Q et al., *Invest Ophthalmol Vis Sci.* 2013 Jun. 6; 54(6):3941-8; Bai Y et al., *J Mol Cell Cardiol.* 2013 April; 57:82-95; Miao X et al., *Nutr Metab (Lond).* 2012 Sep. 15; 9(1):84; Li B et al., *Exp Diabetes Res.* 2012; 2012:216512; and Yu Z W et al., *World J Diabetes.* 2012 Jan. 15; 3(1):19-28.

Similarly, in the case of cardiac-related inflammation such as ischemia and stroke, the antioxidant response mediated by the NRF2 pathway has been shown to protect against the effects of such inflammatory responses. See, for example, Shih A Y et al., *J Neurosci.* 2005 Nov. 2; 25(44):10321-35; Yang C et al., *Brain Res.* 2009 Jul. 28; 1282:133-41; Son T G et al., *J Neurochem.* 2010 March; 112(5): 1316-26; Li M et al., *Biol Pharm Bull.* 2011; 34(5):595-601; and Chen L et al., *Brain Res.* 2012 Sep. 26; 1475:80-7. In addition to inflammatory diseases, such as those described above, the NRF2 pathway has broader implication in the treatment of general inflammation as this pathway is ultimately involved with the regulation of NF-κB dependent pathways.

The NRF2 pathway has also been linked with ageing and age-induced disorders such as oxidative stress brain ageing. See, for example, Li X H et al., *J. Neurosci Lett.* 2012 Apr. 11; 514(1):46-50; Kwon J et al., *EMBO Rep.* 2012 Feb. 1; 13(2):150-6; Sykiotis G P et al., *Curr Opin Clin Nutr Metab Care.* 2011 January; 14(1):41-8; Lewis K N et al., *Integr Comp Biol.* 2010 November; 50(5):829-43; and Sykiotis G P and Bohmann D., *Dev Cell.* 2008 January; 14(1):76-85.

Accordingly, the compounds provided herein are useful for promoting survival of a eukaryotic cell (e.g., a mammalian cell). For example, administration of a therapeutically effective amount of a compound provided herein can increase the lifespan of the cell and increase the cell's ability to resist stress. In some embodiments, the stress includes heat shock, oxidative stress, osmotic stress, DNA damage, inadequate salt level, inadequate nitrogen level, or inadequate nutrient level. The compounds provided herein can also mimic the effect of nutrient restriction on the cell.

In some embodiments, the compounds provided herein can be used to treat or prevent a disease or disorder associated with cell death or aging in a subject. For example, an ageing-related disease can include stroke, a cardiovascular disease, skin cancer, arthritis, high blood pressure, diabetes, or age-dependent Alzheimer's, Parkinson's, or Huntington's diseases. In addition to the references cited above, see for example, Hirota A et al., *Exp Dermatol.* 2011 August; 20(8):664-8; Senthil Kumar K J et al., *Food Chem Toxicol.* 2013 September; 59:55-66; Hseu Y C et al., *Food Chem Toxicol.* 2012 May; 50(5):1245-55; Saw C L et al, *Mol Carcinog.* 2011 June; 50(6):479-86; Schäfer M et al., *Cell Cycle.* 2010 Aug. 1; 9(15):2917-8; Schäfer M et al., *Genes Dev.* 2010 May 15; 24(10):1045-58; Leiser S F and Miller R A. *Mol Cell Biol.* 2010 February; 30(3):871-84; auf dem Keller U et al., *Mol Cell Biol.* 2006 May; 26(10):3773-84. In addition, these mechanisms have been linked with increasing the longevity of a species. For example, see, Li X H et al., *Neurosci Lett.* 2012 Apr. 11; 514(1):46-50; Kwon J et al., *EMBO Rep.* 2012 Feb. 1; 13(2):150-6; Sykiotis G P et al., *Curr Opin Clin Nutr Metab Care.* 2011 January; 14(1):41-8; Lewis K N et al., *Integr Comp Biol.* 2010 November; 50(5):829-43; and Sykiotis G P and Bohmann D. *Dev Cell.* 2008 January; 14(1):76-85.

Further provided herein is a method for treating cancer in a subject, the method comprising administering to the subject a therapeutically effective amount of a compound provided herein. In some cases, the cancer can include prostate cancer, bladder cancer, ovarian cancer, breast cancer (e.g., breast cancer with mutated BRCA1), head and neck cancer, chronic lymphocytic leukemia, thymus cancer, hepatocellular carcinoma, colorectal cancer, colon cancer, skin cancer, pancreatic cancer, leukemia, lung cancer, glioblastoma, cervical cancer, lymphoma, and multiple myeloma. For example, the cancer can be skin cancer.

A method of activating a NRF2 pathway in a cell is also provided herein, the method comprising contacting the cell with an effective amount of a compound provided herein. The method of activating a NRF2 pathway in a cell may be performed by contacting the cell with a compound provided herein, or a pharmaceutically acceptable salt thereof, in vitro, thereby inducing activation of a NRF2 pathway in a cell in vitro. Uses of such an in vitro method of activating a NRF2 pathway include, but are not limited to use in a screening assay (for example, wherein a compound provided herein is used as a positive control or standard compared to compounds of unknown activity or potency in activating a NRF2 pathway). In some embodiments thereof, the NRF2 pathway is activated in a eukaryotic cell (e.g., a mammalian cell).

Activation of a NRF2 pathway can be determined by, for example, the methods described in the Examples provided herein.

The method of activating a NRF2 pathway in a cell may be performed, for example, by contacting a cell with a compound provided herein, in vivo, thereby activating a NRF2 pathway in a subject in vivo. The contacting is achieved by causing a compound provided herein, or a pharmaceutically acceptable salt thereof, to be present in the subject in an amount effective to achieve activation of the NRF2 pathway. This may be achieved, for example, by administering a therapeutically effective amount of a compound provided herein, or a pharmaceutically acceptable salt thereof, to a subject. Uses of such an in vivo method of activating a NRF2 pathway include, but are not limited to use in methods of treating a disease or condition, wherein activating a NRF2 pathway is beneficial. In some embodiments thereof, the NRF2 pathway is activated in a mammal (e.g., a human).

In some embodiments, the compounds provided herein also inhibit one or more sirtuins in the cell. For example, the compound can inhibit one or more sirtuins selected from the group consisting of: SIRT1, SIRT2, SIRT3, SIRT4, SIRT5, SIRT6, and SIRT7. In some embodiments, the compound inhibits SIRT2.

A method of inhibiting a KEAP1 protein in a cell is also provided herein, the method comprising contacting the cell with an effective amount of a compound provided herein. The method of inhibiting a KEAP1 protein in a cell may be performed by contacting the cell with a compound provided herein, or a pharmaceutically acceptable salt thereof, in vitro, thereby inducing inhibition of a KEAP1 protein in a cell in vitro. Uses of such an in vitro method of inhibiting a KEAP1 protein include, but are not limited to use in a screening assay (for example, wherein a compound provided herein is used as a positive control or standard compared to compounds of unknown activity or potency in inhibiting a KEAP1 protein). In some embodiments thereof, the KEAP1 protein is inhibited in a eukaryotic cell (e.g., a mammalian cell).

Inhibition of a KEAP1 protein can be determined by, for example, the methods described in the Examples provided herein.

The method of inhibiting a KEAP1 protein in a cell may be performed, for example, by contacting a cell with a compound provided herein, in vivo, thereby inhibiting a KEAP1 protein in a subject in vivo. The contacting is achieved by causing a compound provided herein, or a pharmaceutically acceptable salt thereof, to be present in the subject in an amount effective to achieve inhibition of a KEAP1 protein. This may be achieved, for example, by administering a therapeutically effective amount of a compound provided herein, or a pharmaceutically acceptable salt thereof, to a subject. Uses of such an in vivo method of inhibiting a KEAP1 protein include, but are not limited to use in methods of treating a disease or condition, wherein inhibiting a KEAP1 protein is beneficial. In some embodiments thereof, the KEAP1 protein is inhibited in a mammal (e.g., a human).

Pharmaceutical Compositions

The methods provided herein include the manufacture and use of pharmaceutical compositions, which include compounds identified by a method provided herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

The term "pharmaceutically acceptable salt" refers to salts which possess toxicity profiles within a range that affords utility in pharmaceutical applications. Pharmaceutically unacceptable salts may nonetheless possess properties such as high crystallinity, which may render them useful, for example in processes of synthesis, purification or formulation of compounds provided herein. In general the useful properties of the compounds provided herein do not depend critically on whether the compound is or is not in a salt form, so unless clearly indicated otherwise (such as specifying that the compound should be in "free base" or "free acid" form), reference in the specification to a compound provided herein should be understood as encompassing salt forms of the compound, whether or not this is explicitly stated.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts.

All of these salts may be prepared by conventional means from the corresponding compound by reacting, for example, the appropriate acid or base with a compound provided herein. Preferably the salts are in crystalline form, and preferably prepared by crystallization of the salt from a suitable solvent. A person skilled in the art will understand how to prepare and select suitable salt forms for example, as described in *Handbook of Pharmaceutical Salts: Properties, Selection, and Use* By P. H. Stahl and C. G. Wermuth (Wiley-VCH 2002).

A pharmaceutical composition is typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injection can include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. The composition should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Additionally, intranasal delivery is possible, as described in, inter alia, Hamajima et al., *Clin. Immunol. Immunopathol.*, 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

The pharmaceutical compositions can be included in a container, pack, or dispenser together with instructions for administration.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Definitions

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "subject," as used herein, includes both humans and other animals, particularly mammals. Thus, the methods are applicable to both human therapy and veterinary applications. In some embodiments, the subject is a mammal, for example, a primate. In some embodiments, the subject is a human.

A "therapeutically effective" amount of a compound provided herein is typically one which is sufficient to achieve the desired effect and may vary according to the nature and severity of the disease condition, and the potency of the compound. It will be appreciated that different concentrations may be employed for prophylaxis than for treatment of an active disease.

The term, "compound," as used herein is meant to include all stereoisomers, geometric isomers, and tautomers of the structures depicted. Compounds herein identified by name or structure as one particular tautomeric form are intended to include other tautomeric forms unless otherwise specified.

In some embodiments, a compound provided herein, or salt thereof, is substantially isolated. By "substantially isolated" is meant that the compound is at least partially or substantially separated from the environment in which it was formed or detected. Partial separation can include, for example, a composition enriched in the compound provided herein. Substantial separation can include compositions containing at least about 50%, at least about 60%, at least about 70%, at least about 80%, at least about 90%, at least about 95%, at least about 97%, or at least about 99% by weight of the compound provided herein, or salt thereof. Methods for isolating compounds and their salts are routine in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "contacting" means bringing at least two moieties together, whether in an in vitro system or an in vivo system.

The terms "treating" and "treatment" mean causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

EXAMPLES

The invention is further described in the following examples, which do not limit the scope of the invention described in the claims.

General Methods

Compounds were purchased, dissolved in molecular biology grade dimethyl sulfoxide (DMSO) to 10 mM stock concentration, aliquoted, and stored at −80° C. Dimethyl fumarate was purchased, dissolved in DMSO to a 10 mM concentrated solution, aliquoted, and stored at −80° C.

Protein Extraction and Western Analysis

To assess protein levels, cell extracts were prepared from cells washed with PBS and lysed with buffer containing 2% SDS, Complete EDTA-free Protease Inhibitor Cocktail (Roche) and 1 mM phenylmethylsulfonyl fluoride. To prepare brain extracts for analysis, frozen mouse cortical tissues were homogenized in PBS containing protease inhibitors with an Kontes Pellet Pestle (Kimble/Kontes). They were later sonicated and lysed overnight at 4° C. in 2× volume of lysis buffer containing 2% SDS and protease inhibitors. Protein concentrations in ST14A cell extracts and homogenized cortical tissues were evaluated using a BCA analysis kit and normalized. Samples were prepared in a SDS buffer containing DTT and separated on bis-acrylamide protein gels via electrophoresis and transferred onto a 0.2 µm PVDF membrane). Membranes were probed for NQO1 (Sigma N5288, 1:1,000), GCLM, (Abcam ab126704, 1:800), SIRT2 (Sigma S8447, 1:2,500), histone H3 (Cell Signaling 4499, 1:2,000), acetylated H3 (K56) (Millipore 04-1135, 1:500), TNFα (Abcam ab1793, 1:1,500), GADPH (Millipore MAB374, 1:10,000), actin (Sigma A2066, 1:1250), α-tubulin (Sigma T6074, 1:20,000), and acetylated α-tubulin (Sigma T6793, 1:2,500) overnight in 5% milk in PBST at 4° C. on a rocker. Membranes were thrice washed in PBST for 15 min on a shaker and incubated in either an anti-rabbit-HRP (Bio-Rad 170-5046, 1:10,000) or anti-mouse-HRP (Sigma A3682, 1:4,000) secondary solution as appropriate in 3% milk in PBST for 1 hr at room temperature on a rocker.

After four washes of 15 min in PBST on a shaker, blots were visualized using SuperSignal West Pico Chemiluminescent Substrate (Pierce 34080) or SuperSignal West Dura Extended Duration Substrate (Thermo 34075) and exposed on Scientific Imaging Film (Kodak 864 6770).

A densiometric analysis of the western blots was conducted using ImageJ software available from the National Institutes of Health, USA. Blot intensities were normalized to α-tubulin or GADPH levels. Statistical analyses were performed using the Student's t-Test and statistical significance was reported as follows: * P<0.05;  P<0.01; *P<001.

Microarray Data Analysis

RNA was extracted from HD mutant and wild type ST14A cells, differentiated for 24 hours and treated with vehicle (DMSO) or with 5 µM MIND4, using the RNeasy kit (Qiagen). Labeled cRNAs were prepared and hybridized to Affymetrix GeneChip Rat Genome 230 2.0 microarrays according to the manufacturer's instructions. Affymetrix CEL (intensity) files from hybridized arrays were imported into the Partek Genome Suite, Partek Incorporated, for biostatistical analysis. 2 CEL files were used for each experimental condition: wild type (WT) untreated, MIND4 treated (WT/MIND4), mutant (MTT) untreated, and mutant (MTT) MIND4-terated (MTT/MIND4). Two-way ANOVA was performed with interaction term included and three of the evaluated contrasts were of interest (Case I, II, and III). Gene lists were created for each of the three contrasts using the thresholds of absolute value of fold-change>1.5 and p-value with False Discovery Rate (FDR)<0.05. The lengths of the gene lists are for Case I (DP)-1765 genes, for Case II (TP)-1797 genes, and for Case III (MDDP)-268 genes. These three gene lists were imported into Ingenuity IPA for pathway and network analyses. These analyses provided Networks (graph structures of molecules connected by relationships in the IPA knowledgebase), Functions (lists of molecules grouped together due to their contribution to a biological function) and Canonical Pathways (molecules and relationships that participate in a biological pathway). Scores are assigned according to the probability that the genes from the user's list might appear in the function or pathway by chance (right-tailed Fisher's Exact Test).

Primary Striatal Neuron Cultures

Primary neuruonal cultures were prepared from mechanically dissociated ganglionic eminence tissues of wild type rat embryos embryonic day 16 (E16). This procedure results in a predominant population of Neuronal nuclear antigen (NeuN)-positive and DARPP-32-positive neurons with some astroglia. Treatments of cultures with MIND4 were at 5 µM (whereas control cultures treated with vehicle (DMSO) only). RNA was extracted by using the RNeasy system (Qiagen), following the manufacturer's protocol. Gene expression changes were assessed by microarray analysis as described previously [Luthi-Carter, 2010].

Example 1—Sirtuin Biochemical Deacetylation Assays

Modulation of sirtuin activity by compounds was assessed using the Flour de Lys fluorescent biochemical assay in a 96-well format as described (Outeiro et al., 2007). The deacetylation reaction was performed at 37° C. for an hour in the presence of human recombinant enzymes: SIRT1 (BioMol-SE-239) 1 unit/per reaction, SIRT2 (BioMol-SE-251) 5 units/per reaction, or SIRT3 (BioMol-SE-270) 5 units/per reaction, compound of interest, standard buffer, 50 µM substrate, and 500 µM NAD$^+$ according to the manufacturer's protocol.

The neuroprotective properties of several selective sirtuin-2 (SIRT2) deacetylase inhibitors in Parkinson's and Huntington's disease models were previously characterized (Chopra et al., 2012; Luthi-Carter et al., 2010; Outeiro et al., 2007). For analyzing the SIRT2 inhibition mechanism of MIND4 in a continuous coupled enzymatic assay with an α-tubulin peptide substrate, the recombinant enzyme was prepared and its activity analyzed as described previously [Moniot, 2013]. The IC50 for MIND4 was determined using α-tubulin and NAD$^+$ at 150 µM and 500 µM, respectively. The titration with NAD$^+$ was performed at 150 µM α-tubulin peptide, and the peptide titration at 1 mM NAD$^+$. Data analysis and fitting was done in Grafit 7 (Erithacus Software, Horley, UK).

Additional screening was performed to identify additional highly selective and potent SIRT2 inhibitors to be used as chemical probes to investigate underlying mechanisms involved in the observed neuroprotection. This screening yielded the candidate compound (5-nitro-8-{[5-(phenoxymethyl)-4-phenyl-4H-1,2,4-triazol-3-yl]thio}quinoline), henceforth MIND4.

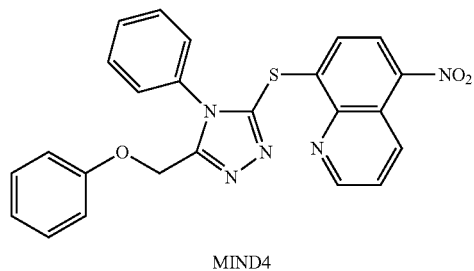 [SMILES: O=[N+]([O-])c1ccc(Sc2nnc(COc3ccccc3)n2-c2ccccc2)c2ncccc12]

MIND4

MIND4 shows dose-dependent and selective inhibition of human recombinant SIRT2 deacetylase, but not of SIRT1 and SIRT3 activities in vitro, in biochemical assays (FIG. 1A-C).

Structure-activity relationship (SAR) studies identified additional analogs with selective SIRT2 inhibition activities. Results are shown in Table 1.

TABLE 1

| Compound ID | Structure | SIRT2 IC50 |
|---|---|---|
| MIND4 | 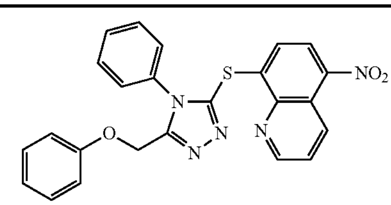 | 1.7 µM |

TABLE 1-continued
| Compound ID | Structure | SIRT2 IC50 |
|---|---|---|
| MIND4-2 | 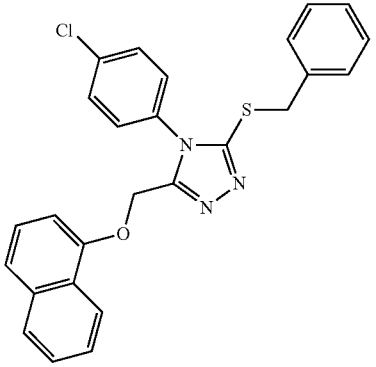 [SMILES: Clc1ccc(-n2c(COc3cccc4ccccc34)nnc2SCc2ccccc2)cc1] | 12 µM |
| MIND4-11 | 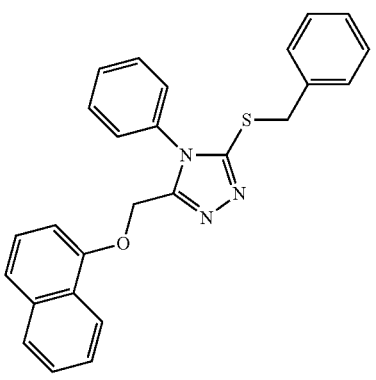 [SMILES: c1ccc(CSc2nnc(COc3cccc4ccccc34)n2-c2ccccc2)cc1] | 4.5 µM |
| MIND4-12 | 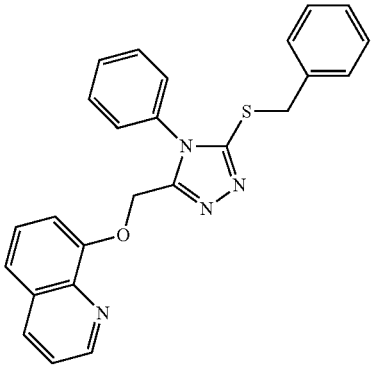 | 9 µM |
| MIND4-19 | 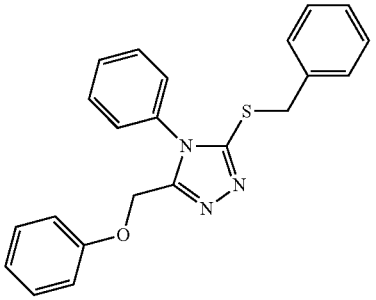 [SMILES: c1ccc(CSc2nnc(COc3ccccc3)n2-c2ccccc2)cc1] | 7 µM |
| MIND4-20 | 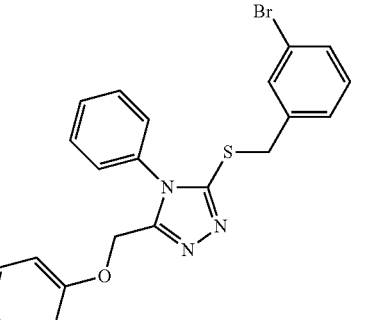 | 5 µM |
| MIND4-21 | 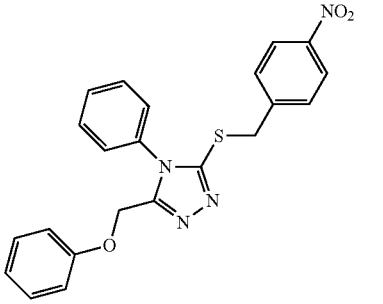 [SMILES: O=[N+]([O-])c1ccc(CSc2nnc(COc3ccccc3)n2-c2ccccc2)cc1] | 10 µM |
| MIND4-22 | 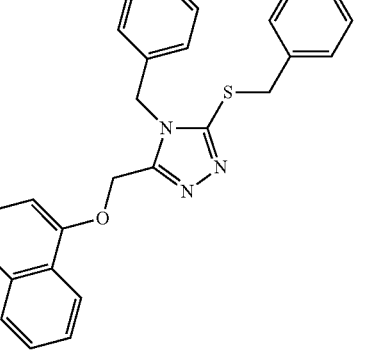 | 6 µM |
| MIND4-23 | 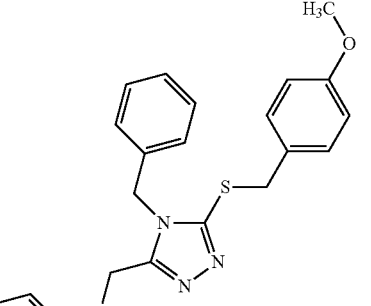 | 9 µM |

Example 2—Rat Embryonic Striatal ST14A Cells

Compound bioactivity was tested in the rat embryonic striatal cell lines ST14A, which stably express either a mutant expanded repeat (128Q) or wild type (26Q) 546 amino acid huntingtin (HTT) fragment (a generous gift of E. Cattaneo) (Ehrlich et al., 2001) ST14A cells were propagated at 33° C. in the presence of serum. To induce neuronal differentiation, cells were serum deprived and cultured at 37° C. in the presence of N2 supplement. Cells were treated with compounds concurrently with induction of neuronal differentiation for 24 hours, as described (Quinti et al., 2010).

Figure 2:
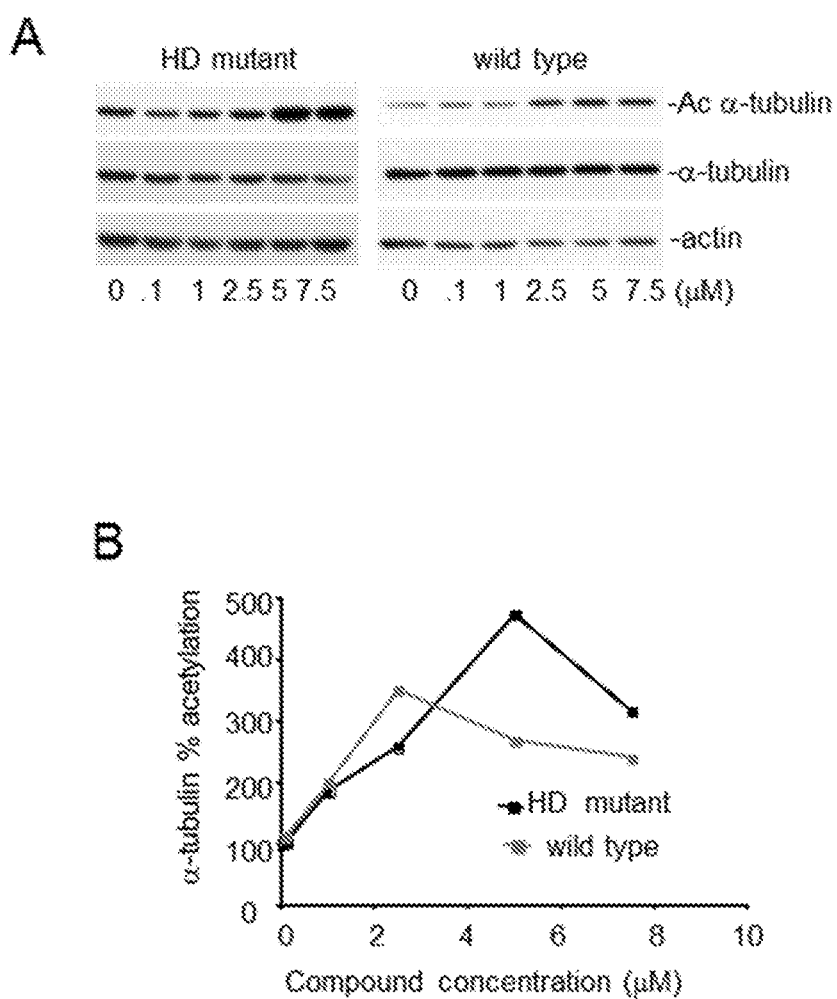
FIG. 2 illustrates the properties of MIND4 as inhibitor of SIRT2 deacetylase.

Cells were switched to differentiation media and simultaneously treated with MIND4 for 6 hours, resulting in a dose dependent increase in acetylation of α-tubulin (lysine K40), a known substrate of SIRT2 deacetylase activity (FIG. 2A-B). This increased α-tubulin acetylation in compound-treated cells was consistent with the activity of MIND4 as a SIRT2 inhibitor.

Example 3—Drug-Treatment Effects on Survival of Wild Type and HD Mouse Primary Cortical Neurons Embryonic tissue from wild type and 140Q mouse brains (E15-E17 days into pregnancy) was used to isolate and plate cortical neurons as described (Valencia et al., 2013). Neurons were plated at $8\times10^5$ cell/ml in a 24-well plate supplemented with 25 μM of L-glutamate and 10 μM of 2-β-mercapto-ethanol (Gibco). Plates were previously coated with poly-L-lysine (30-70 kDa, SIGMA) in borate buffer at pH 8.0 and coated again using DMEM/F12+FBS 10% for 2 hours prior to plating. After 3 days in culture, neurons were treated with 10 μM of β-D-cytosine arabinofurinoside for 24 hours to prevent the proliferation of non-neuronal cells.

Figure 3:
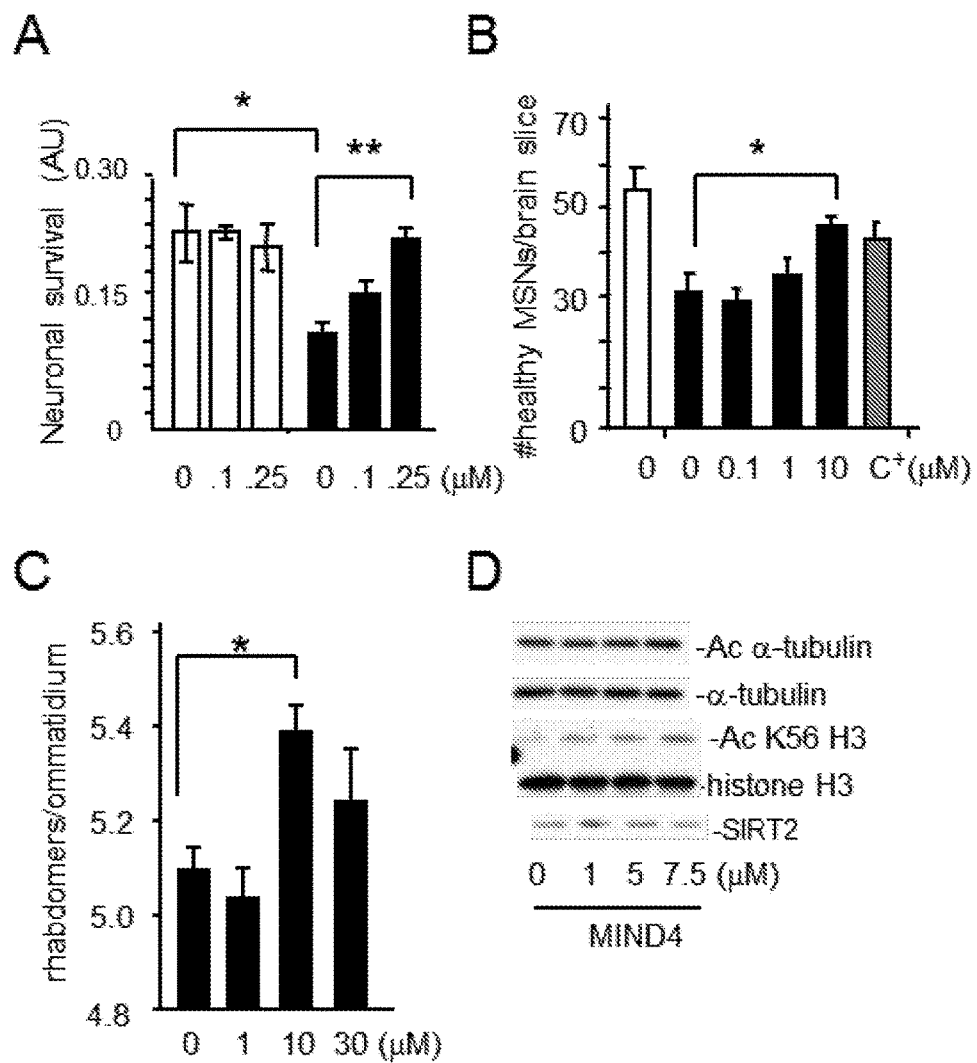
FIG. 3 shows how MIND4 mediates neuroprotection in HD models.

Neuronal Viability Assay:

Neurons were supplemented with MIND4 at different concentrations 0, 0.1, 0.25 and 0.5 μM at days in vitro 4, 6 and 8 (FIG. 3A). Doses of 0.1 μM and 0.25 μM MIND4 were selected for this treatment regimen, since as previously shown the SIRT2 inhibitors achieved significant protective effects on primary neuronal cultures (Outeiro et al., 2007). To maintain drug concentrations, half of the culture media was replenished with fresh media at each time point and MIND4 treatment doses were adjusted accordingly. Cell viability was measured at DIV 10 as previously described based on the ability of viable neurons to transformed MTT (3-(4,5-Dimethylthiazol-2-yl)-2,5-diphenyltetrazolium bromide) into formazan blue crystals (Valencia et al., 2013). Neurons were incubated with 0.5 mg/ml of MTT for 15 minutes, media was then discarded and formazan blue crystals were dissolved in DMSO 100% and read at 540 nm in a Vector plate reader. Results are expressed as Mean±Standard deviation absorbance units at 540 nm (AU). P values were obtained using a Student's t-test from an N=6 wells per condition for treated wild type and HD neurons.

MIND4 treatment improved survival of HD neurons at both doses and notably 0.25 μM improved viability of HD neurons compared to wild type levels (FIG. 3A).

Example 4—Compound Test in Acutely Transfected Rat Brain Slice Culture Assay Coronal brain slices (250 μm thick) containing both cortex and striatum were prepared from CD Sprague-Dawley rat pups at postnatal day 10 and placed into interface culture as previously described (Reinhart et al., 2011). A biolistic device (Helios Gene Gun; Bio-Rad) was then used to co-transfect the brain slices with YFP visual reporter and a 90 amino acid mutant huntingtin plasmid containing human htt exon-1 harboring a 73 CAG repeat to induce neurodegeneration of medium spiny neurons (MSNs). mHTTex1 expression induced progressive neurodegeneration of medium spiny neurons (MSNs) compared to controls over a period of 4 days.

MIND4 was added to the culture wells at the time of slice preparation and transfection to a final DMSO concentration of 0.1%; this concentration of DMSO was also added to all control wells. The positive control used for these experiments was the pan-caspase inhibitor Boc-D-FMK at 100 μM (Varma et al., 2007). YFP co-transfected MSNs were identified 4 days after incubation by their location within the striatum and by their characteristic dendritic arborization as previously described (Crittenden et al., 2010; Reinhart et al., 2011). Briefly, MSNs exhibiting normal-sized cell bodies, even and continuous expression of YFP within all cell compartments, and >2 discernible primary dendrites >2 cell bodies long were scored as healthy. Ordinate axis expresses the mean numbers of healthy YFP-positive MSNs per striatal region in each brain slice. Statistical significance was tested using ANOVA followed by Dunnett's post hoc comparison test at the 0.05 confidence level.

Treatment with MIND4 significantly protected against mHTTex1-induced neurodegeneration in a concentration-dependent manner (FIG. 3B). Neuroprotection with MIND4 at the highest 10 μM concentration was comparable to the efficacy of a reference compound, the pan-caspase inhibitor Boc-D-FMK ($C^+$) at 100 μM (Varma et al., 2007) (FIG. 3B). Note that somewhat higher concentrations of compounds were used for these experiments compared to cell culture because of limited diffusion into intact brain tissues.

Example 5—Drug Test in *Drosophila* Model of HD

Compound treatment of *Drosophila* HD model and efficacy analysis of MIND4 effects on photoreceptor neurons was performed as described (Steffan et al., 2001; Pallos et al., 2008). *Drosophila* models have been important in the genetic identification of pathological and neuroprotective mechanisms as well as for testing therapeutic candidates in HD (Marsh et al., 2003). In wild type flies, seven rhabdomeres (photoreceptor neurons) are visible in the adult eye, whereas chronic expression of mHTTex1 causes progressive degeneration of these neurons, detected as a reduction of rhabdomere number. Rhabdomeres were counted on day 7 after eclosion in animals treated with varying doses of MIND4. The indicated numbers of flies were scored for each condition (n) with the number of ommatidia scored indicated in parentheses. Trial 1: DMSO=11(449); MIND4 1 μM=3 (112); MIND4 10 μM=9(337); MIND4 10 μM=9(364). Trial 2: DMSO=8(361); MIND4 10 μM=8(292). Relative rescue of photoreceptor neurons in flies treated vs. untreated with MIND4 at 10 μM dose was estimated for Trial 1 and Trial 2 as 22.6% and 20.7%; t-test significance for Trial1 $p<0.001$ and for Trial 2 $p<0.02$.

MIND4 was tested for its potential efficacy by monitoring the degeneration of photoreceptor neurons in the eyes of *Drosophila* expressing expanded repeat HTT exon 1 protein in all neurons beginning during embryogenesis (Steffan et al., 2001). In wild type flies, seven rhabdomeres (photoreceptor neurons) are visible in the adult eye. Chronic expression of mutant HTT causes progressive degeneration of these neurons, detected as a reduction of rhabdomeres number. Rhabdomeres were counted on day 7 after eclosion in animals treated with varying doses of MIND4. Animals treated with 10 µM MIND4 have significantly more surviving rhabdomeres than untreated controls (FIG. 3C). The neuroprotective effects of MIND4 were confirmed in an independent second trial conducted at the 10 µM dose. Relative rescue was estimated as 22.6% and 20.7% for the first and second trials respectively.

Example 6—Bioactivity of MIND4 in Primary Neurons

Based upon the robust neuroprotection observed in HD model systems expressing both mutant HTT fragments and full-length mutant HTT, verification of the bioactivity of MIND4 as SIRT2 inhibitor in primary neurons was sought. Full length SIRT2 protein (isoform SIRT2.1) was preferentially expressed in primary cortical neurons (DIV11) derived from wild type mice (FIG. 3D), supporting the presence of the putative MIND4 target (Maxwell et al., 2011). In MIND4-treated neurons, only subtle increases of acetylation of α-tubulin and Histone 3 K56, another known SIRT2 substrate, were observed (Das et al., 2009).

In primary neurons, which preferentially express a full-length SIRT2 (SIRT2.1 isoform), a transient 6 hr MIND4 treatment increased acetylation of histone 3 K56 and K27, and to a significantly lesser extent of α-tubulin K40, which is an established target of SIRT2 and HDAC6. When supplemented at 5 mM, the HDAC6 inhibitor tubacin significantly increased α-tubulin acetylation, providing reference activity and further suggesting that MIND4 exerts only subtle SIRT2 inhibition in neurons.

Based on the MIND4-dependent modulation of histone acetylation, it was concluded that MIND4 is bioactive, however the evidence that this compound primarily targets cytoplasmic SIRT2 was not conclusive. The lack of convincing target engagement of MIND4 therefore raised the possibility that an activity distinct from SIRT2 inhibition is primarily responsible for the observed neuroprotection in HD neuronal models.

Example 7—Transcriptional Array Analysis Reveals Nrf2/KEAP1/ARE Pathway Activation by MIND4

To determine whether MIND4 might engage targets other than SIRT2, the gene expression changes in treated versus untreated mutant HTT and wild type ST14A cells were evaluated using an approach described previously (Luthi-Carter et al., 2010). RNA from rat embryonic striatal (ST14A) cells stably expressing a 546 amino acid HTT fragment containing either an expanded (128Q) or wild type (26Q) repeat was extracted following treatment with 5 µM MIND4 for 24 hours was extracted and run on Affymetrix rat microarrays (Affy GeneChip Rat Genome 230 2.0 array) as described above in General Methods. Two replicates for each of the experimental conditions were imported into Partek Genome Suite for biostatistical analysis. Genes showing significant differential expression were identified by ANOVA, for three contrasts, resulting in three gene-lists: mutant HD (MT) vs. wild type (WT)=Case I (Disease Phenotype); MT/MIND4 treated vs. WT=Case II (Treatment Phenotype), and MT/MIND4 treated vs. MT=Case III (Mutant Drug-Dependent Phenotype). These represented transcriptional alterations in MT compared to WT cells (Case I), in MT treated compared to WT cells (Case II), and in MT treated cells compared to untreated MT cells (Case III). The lists, Cases I-III, were then imported into Ingenuity Pathway Analysis (IPA—Ingenuity® Systems, www.ingenuity.com) for pathway and network analyses.

IPA maintains a set of p interactive graphs that visually represent biological signaling and other pathways, designated as Canonical pathways. Molecules in these pathways can be colored by a variety of criteria, including fold-change (e.g. FIG. 4A). After import of data, IPA was used to rank Canonical pathways according to a measure of how unlikely it would be for the genes in the gene lists to be in the pathway by chance, resulting in a negative log p-value.

Figure 4A:
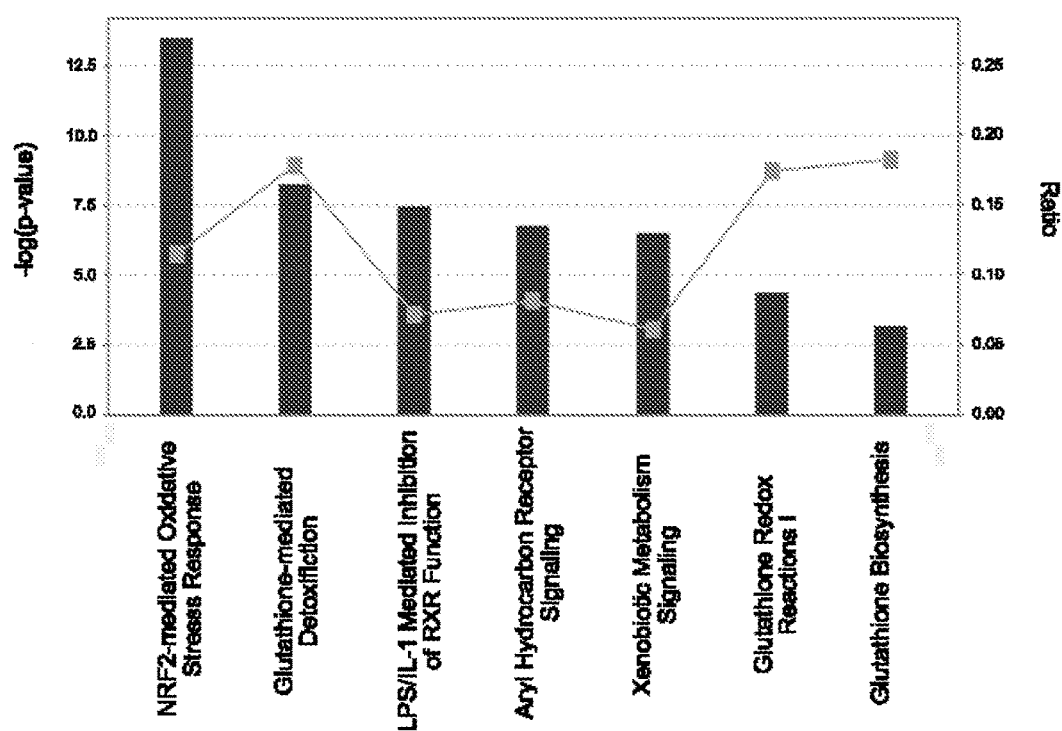
FIG. 4A illustrates the pathway analysis resulted in lists of IPA "Canonical" pathways, sorted according to Fisher's exact test right-tailed p-value. The top Canonical Pathway was NRF2-mediated Oxidative Stress Response. This pathway had a highly significant log(p-value)=13.496. Other pathways are shown in decreasing order of significance to the right. The orange boxes are ratios of the number of MIND4 affected genes in the pathway to the total number in the pathway altogether.
Figure 4B:
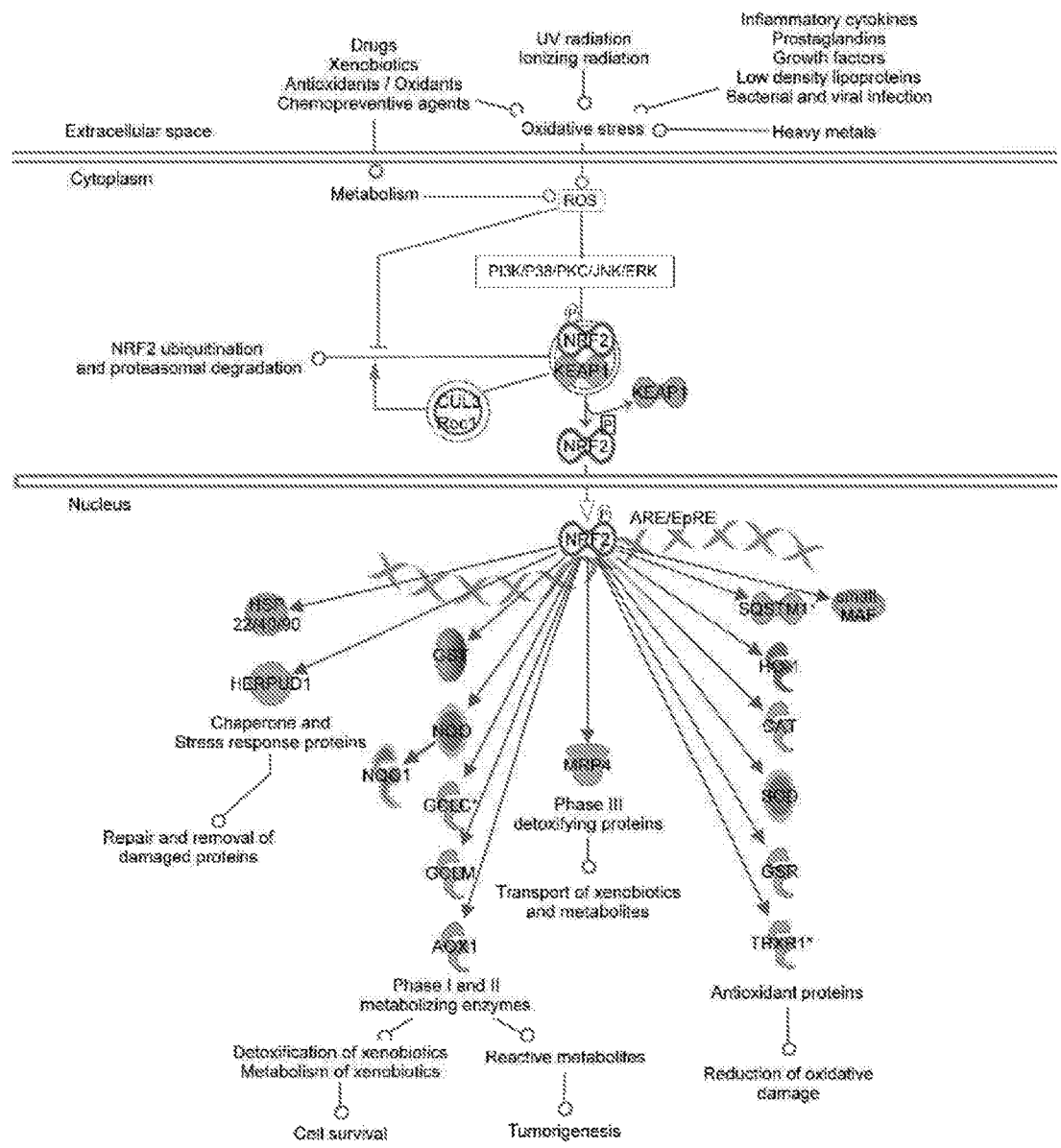
FIG. 4B shows that the fragment of the NRF2 pathway (Case III) shows a fold-change increase of gene expressions as a function of color intensity. Large fold changes are shaded with dark red and decreasing values are shown in lighter red. The pathway shows differential expression in NRF2 downstream targets in mutant HTT expressing cells in the presence and absence of MIND4.
Figure 5A:
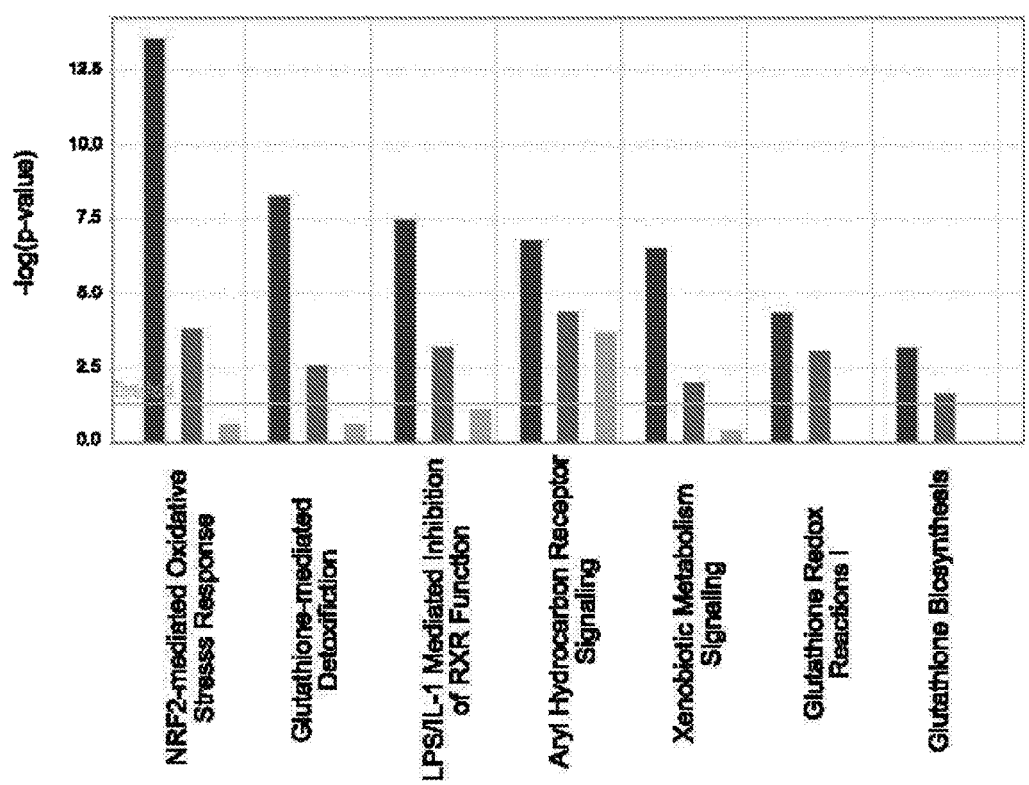
FIG. 5A illustrates the top seven Canonical Pathways, relative to Case III, are sorted by significance as calculated by IPA. NRF2, which is the most significant pathway in Case III, is on the left, with less significant pathways to the right.

Surprisingly, in Case III, MT treated cells compared to untreated MT cells, the top seven most significant Canonical pathways were, in decreasing order of significance: 1) NRF2-mediated oxidative stress response, 2) glutathione-mediated detoxification, 3) LPS/IL-1 mediated inhibition of RXR function, 4) aryl hydrocarbon receptor signaling, 5) xenobiotic metabolism signaling, 6) glutathione redox reactions, and 7) glutathione biosynthesis (FIG. 4A). A comparison of the significance of these seven pathways and lists of modulated genes in all three cases are shown (FIG. 5). FIG. 4B shows a fragment of the IPA Canonical pathway of "NRF2-mediated oxidative stress", colored by red intensity correlative to fold-change of gene expression occurred in Case III. A list of NRF2 responsive genes up-regulated by drug treatment is shown in Table 2. Altogether, the analysis of Case III (MT/MIND4 treated versus MT untreated) shows that drug-dependent changes of transcriptional expression are associated and highly enriched with ARE-responsive genes. The results suggest that MIND4 induces broadly cytoprotective NRF2-dependent responses and implicate efficacy of this newly identified compound activity on mutant HTT-mediated pathogenesis.

TABLE 2

| Gene | Fold Increase |
| --- | --- |
| AOX1 | 3.18 |
| CAT | 1.72 |
| DNAJA4 | 1.53 |
| DNAJB9 | 1.63 |
| FRA1 | 3.17 |
| GCLC | 2.11 |
| GCLM | 3.32 |
| GSR | 2.14 |
| GSTA3 | 20.09 |
| GSTM5 | 1.89 |
| GSTP1 | 2.21 |
| GSTT2/GSTT2B | 1.96 |
| HERPUD1 | 1.55 |
| HO-1 | 6.14 |
| KEAP1 | 1.53 |
| MAFF | 1.75 |
| MGST1 | 1.84 |
| MGST2 | 2.94 |
| MRP4 | 3.37 |
| NQO1 | 7.34 |
| SQSTM1 | 1.82 |
| TRXR1 | 3.31 |

The effects of MIND4 treatment on NRF2 signaling were elucidated through a systems biology approach using biostatistics by Partek Genome Suite to identify genes of interest followed by pathway analysis by IPA. This systems approach strongly indicated that NRF2-mediated oxidative stress signaling was impacted by MIND4 and that this effect was not due to alterations in ER-Stress pathways, further supporting highly specific mechanisms of NRF2 activation through inhibition of KEAP1. Notably, an increase of KEAP1 transcriptional expression was detected (Table 1). Upregulation of KEAP1 synthesis de novo as a response to NRF2 activation is a known negative feedback loop, in which upon nuclear translocation NRF2 induces expression of KEAP1 inhibitor (Lee et al., 2007). The presence of an evolutionary conserved auto-regulatory mechanism suggests that constitutive activation of NRF2 may have adverse effects. This was supported by our results with prolonged constitutive exposure of HD primary neurons with NRF2 activators at high doses, highlighting the necessity of a careful balance of duration and frequency of drug administration in the design of potential treatment paradigms.

The mechanism of NRF2 activation by MIND4 analogs appears to be SIRT2-independent. Although not formally excluded, SIRT2 appeared to be an upstream regulator of the NRF2/KEAP1/ARE pathway and the results clearly showed a dissociation of robust NRF2 activating responses and SIRT2 inhibitory activity of MIND4 compounds. However, the potential benefit of combinatorial treatment, contributed by NRF2 activation and possibly by SIRT2 inhibition or other unidentified activity of MIND4 compounds, should be examined further and offers the exciting possibility of developing compounds with poly-pharmacological therapeutic benefits.

Figure 6:
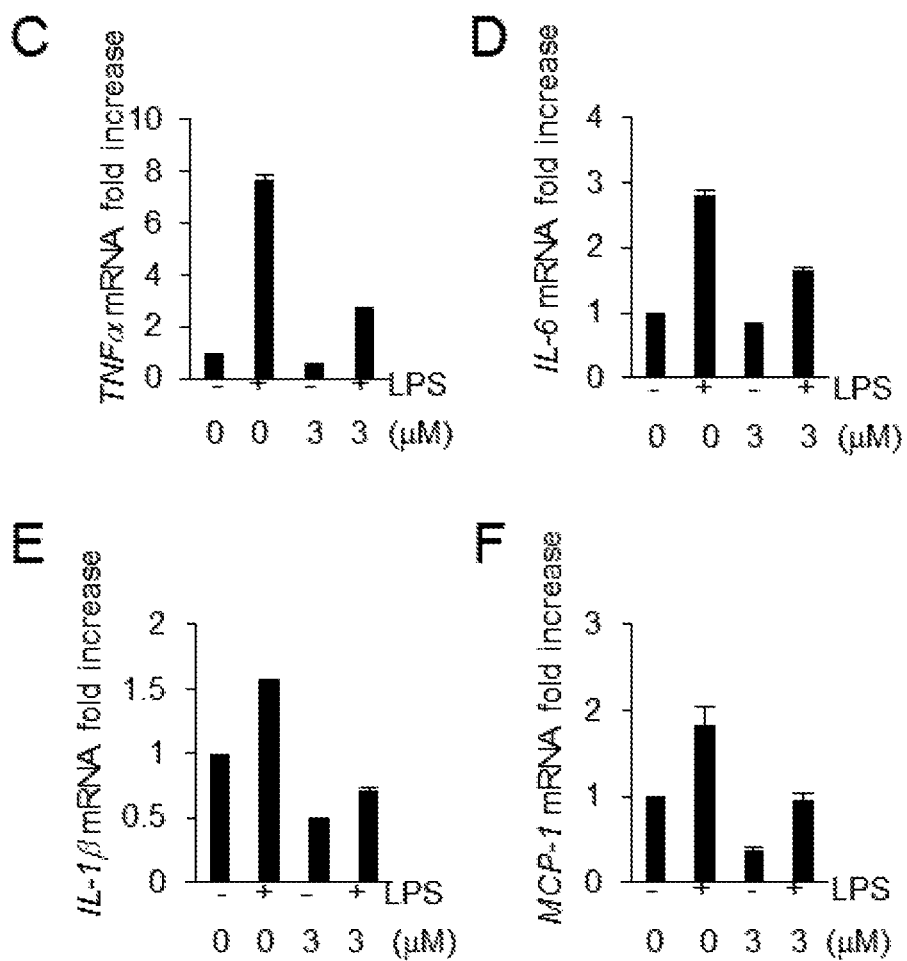
FIG. 6 shows the characterization of NRF2 activation properties by MIND4.

Example 8—Evaluation NRF2-Activating Properties Associated with MIND4 Treatment The major NRF2-reponsive downstream proteins, NQO1 and GCLM, were selected to confirm pathway activation detected by microarray analysis at the protein level. Consistent with the detected transcriptional changes, expression of these reference proteins was increased in differentiated HD mutant and wild type ST14A cells treated with MIND4 (FIG. 6A-B). In both cell lines, MIND4 treatment induced dose-dependent increases of NQO1 and GCLM protein, however the response in HD cells appeared to be more robust (FIG. 6A-B). These data provided further support that the transcription-related effects of MIND4 occur predominantly through NRF2 signaling.

Example 9—Compound Transcriptional Expression Profiling in LPS-Induced Microglia BV2 Cells To further validate the NRF2 activating properties of MIND4, effects of the compound on repression of inflammatory responses were tested in LPS-induced BV2 microglia cells, a model in which the influence of NRF2 signaling on inflammation has been well established (Koh et al., 2011). A BV2 mouse microglia cell line was maintained in DMEM media supplemented with 10% FBS (Sigma) and antibiotic-antimycotic mix. Cells were seeded into 12 well plates at the density of $3 \times 10^5$ cells/well. Cells were treated with the indicated concentrations of MIND4, MIND4-17, and MIND4A compounds for 24 hr. Cells were then stimulated with 10 ng/ml LPS (E. coli) for 2 hr. Total RNA was isolated using ZR Miniprep kit (Zymo Research). 1 µg of total RNA was used to prepare cDNA. Gene expression was analyzed using VeriQuest SYBR green assay in Roche480 thermocycler. The sequences of gene-specific primers for qPCR were as follows:

SEQ ID NO. 1: mIL-1beta for
5'-GCAACTGTTCCTGAACTCAACT-3'

SEQ ID NO. 2: mIL-1beta rev
5'-ATCTTTTGGGGTCCGTCAACT-3'

SEQ ID NO. 3: mIL-6 for
5'-TAGTCCTTCCTACCCCAATTTCC-3'

SEQ ID NO. 4: mIL-6 rev
5'-TTGGTCCTTAGCCACTCCTTC-3'

SEQ ID NO. 5: mGAPDH for
5'-TGTGTCCGTCGTGGATCTGA-3'

SEQ ID NO. 6: mGAPDH rev
5'-GGTCCTCAGTGTAGCCCAAG-3'

SEQ ID NO. 7: mNQO1 for
5'-AGGATGGGAGGTACTCGAATC-3'

SEQ ID NO. 8: mNQO1 rev
5'-AGGCGTCCTTCCTTATATGCTA-3'

SEQ ID NO. 9: mGCLM for
5'-AGGAGCTTCGGGACTGTATCC-3'

SEQ ID NO. 10: mGCLM rev
5'-GGGACATGGTGCATTCCAAAA-3'

SEQ ID NO. 11: mTNFalpha for
5'-CCCTCACACTCAGATCATCTTCT-3'

SEQ ID NO. 12: mTNFalpha rev
3'-GCTACGACGTGGGCTACAG-3'

SEQ ID NO. 13: mMCP-1 for
5'-TTAAAAACCTGGATCGGAACCAA-3'

SEQ ID NO. 14: mMCP-1 rev
5'-GCATTAGCTTCAGATTTACGGGT-3'

Expression of inflammatory genes was assessed in BV2 microglial cells pretreated with MIND4 at 3 µM for 24 hr followed by induction with LPS and q-PCR using gene specific primers. Levels of inflammatory genes TNFα and IL-6, which are induced by LPS, were correspondingly reduced in LPS-activated BV2 cells by MIND4 (FIG. 6C-D). MIND4 treatment also resulted in repression of both basal and LPS-induced transcription of IL-1β and MCP-1 (FIG. 6E-F). In contrast, other structurally diverse bioactive SIRT2 inhibitors tested show no effect on inflammatory responses in activated microglia cells (data not shown). These results were consistent with MIND4 having unique structural features that influence NRF2 activation responses in this in vitro model of induced inflammation.

Example 10—Detection of MIND4 Compound in Mouse Brain

Figure 7:
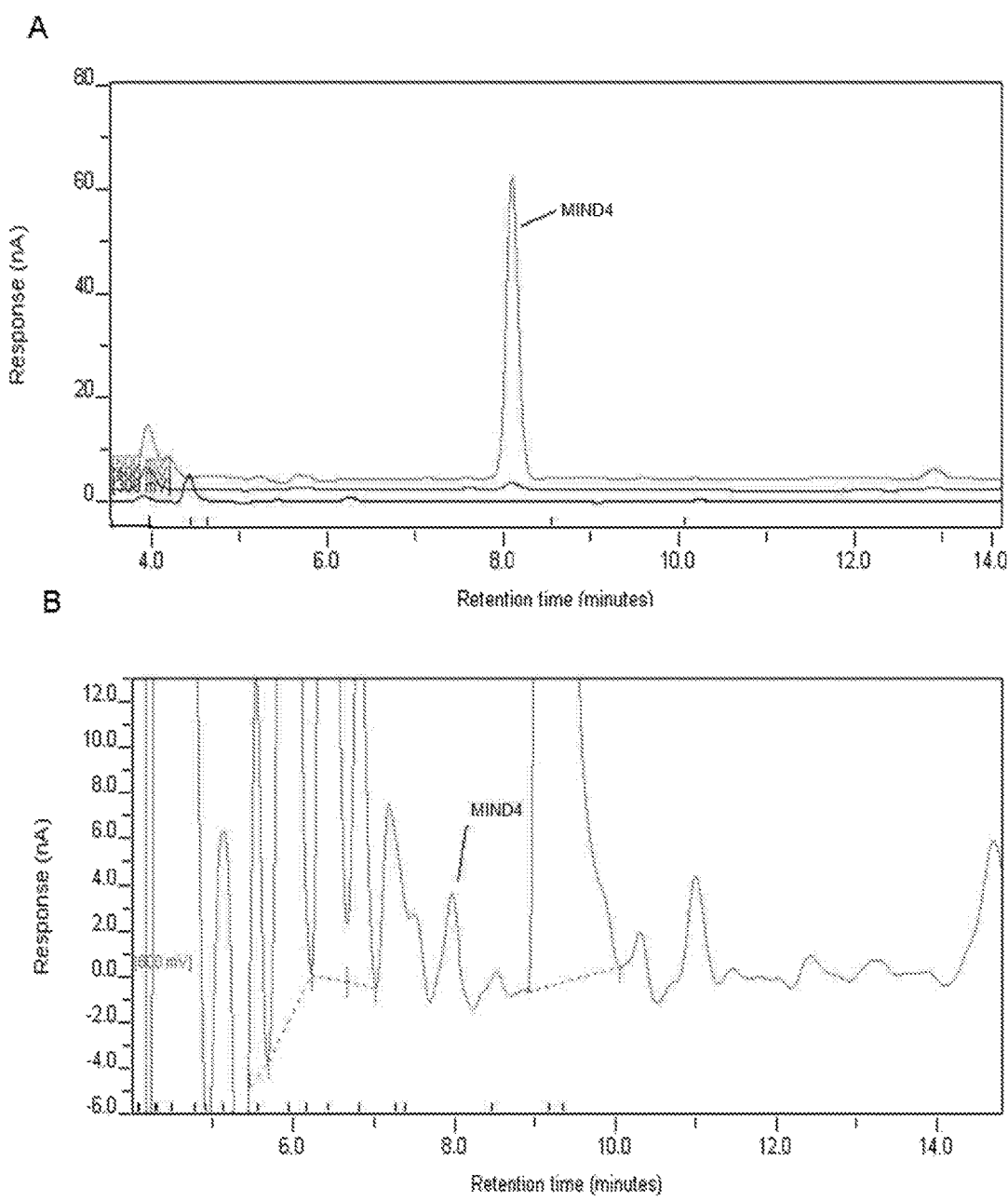
FIG. 7 shows detection of the MIND4 compound in mouse brain. The Compound was administered by intraperitoneal injections to wild type mice. Gradient chromatography coupled with 4-channel colorimetric array detection was enabled the identification of MIND4 in cortex from compound-treated mice.

To evaluate whether MIND4 would also confer an anti-inflammatory effect in vivo, pilot studies were performed to assess brain permeability of MIND4 in mice (FIG. 7A-B). MIND4 was solubilized at 5 mg/ml in 7.5% Cremophor EL (BASF)/2.375% Ethanol in PBS, Wild type mice (N=3) were subjected to MIND4 treatment at escalated dosing from 50 mg/kg up to a final dose of 275 mg/kg administered daily by intraperitoneal (i.p.) injection. No weight loss or sudden death were observed suggesting lack of acute toxicity of MIND4 in that dose range. Mice were sacrificed 2 hours following the last drug administration and isolated cortical samples were subjected to HPLC analysis.

Specifically, frozen mouse cortical tissues were extracted in ice cold methanol containing 0.4% acetic acid (approximately 1:6 ratios), probe sonicated for 5 sec and centrifuged at 22000×g for 20 min at 4 C. The supernatant was dried under centrifugation and vacuum and reconstituted with running buffer. Reverse phase-HPLC/ECA separation was accomplished on shisedo MG240 C18 HPLC column (4.6×

250 mm, 3μ particle size), flow rate 1 ml/min, using 50% methanol in 0.1M sodium phosphate buffer pH 3, isocratic elution was performed for 20 min using 4 channel electrochemical array. Levels of MIND4 in the brain samples were determined using integrated peak areas and the standard curves The peaks were detected in channel 3 at ~8-min retention time. HPLC analysis detected MIND4 presence in wild type mouse cortices at estimated ~0.5 μM concentration, providing preliminary evidence for compound brain permeability.

Example 11—MIND4 Treatment of HD Mouse Model R6/2

The in vivo effects of MIND4 treatment on levels of the inflammatory factor TNFα in vivo were assessed. These effects were most greatly impacted by compound treatment in vitro (e.g. FIG. 6C).

For this animal trial, the well-characterized transgenic R6/2 mouse model of HD was selected, in which severe neurological phenotypes and premature death at age of 12-13 week is conferred by expression of a human HTT exon 1 fragment containing a pathological ~150Q repeat tract (Mangiarini et al., 1996). Female R6/2 mice used in the study were generated by back-crossing R6/2 males with C57BL/6 X CBA F1 females. Mice were genotyped by PCR using tail-tip DNA and were housed five per cage under standard conditions with ad libitum access to water and food. Mice were administered MIND4 daily at the doses of 25 and 50 mg/kg by i.p. injections starting from 6 weeks of age and continued for 4 weeks. The drug suspension at 5 mg/ml in 7.5% Cremophor EL/2.375% Ethanol in PBS, was made fresh daily. Body weights were recorded weekly at the same time of day. At 10 weeks of age, mice were sacrificed 2 hrs after the last injection; brains were removed and snap frozen in liquid nitrogen and kept frozen at −80° C. until analyzed. All animal experiments were carried out in accordance with the National Institutes of Health Guide for the Care and Use of Laboratory Animals and were approved by local animal care committee.

Figure 8:
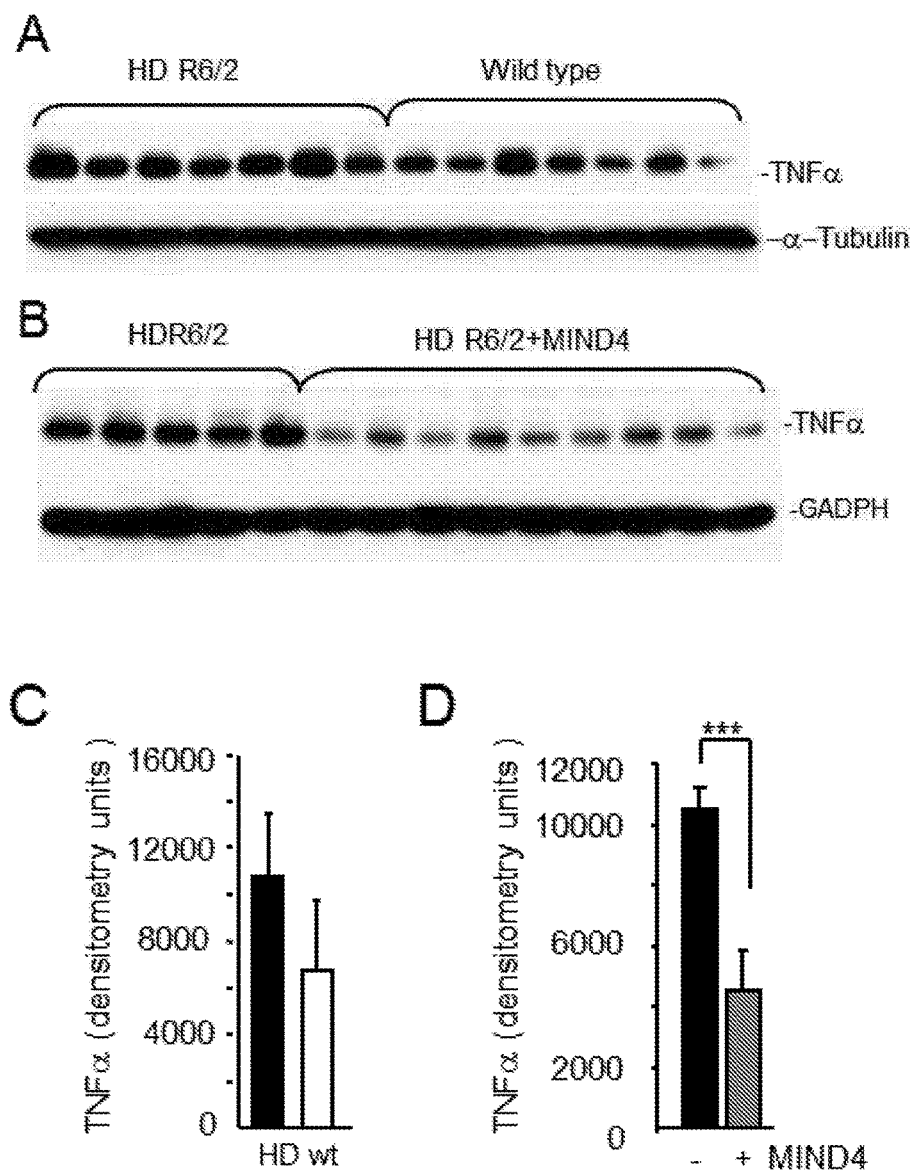
FIG. 8 illustrates the characterization of NRF2 activation properties by MIND4.

TNFα protein levels were measured in the samples by immunoblotting. TNFα levels appeared overall to be higher in R6/2 then in wild type samples, albeit levels were variable and differences were not statistically significant (FIG. 8A-D). A striking reduction of TNFα was observed in MIND4-treated R6/2 mice (FIGS. 8B and 8D). The results were highly reproducible in experiments using samples from two independent protein extractions from MIND4- and vehicle-treated mice. These results are consistent with in vitro observations and establish an important proof-of-concept that MIND4 acts as robust anti-inflammatory agent in brain and potentially might mediate neuroprotection by reducing neuroinflammation, a common pathological feature of neurodegenerative disorders including HD.

Example 12—Characterization NRF2 Activation Properties of MIND4 Scaffold

To further evaluate the NRF2-activating properties and therapeutic potential of the MIND4 scaffold, the properties of MIND4A analogs were tested.

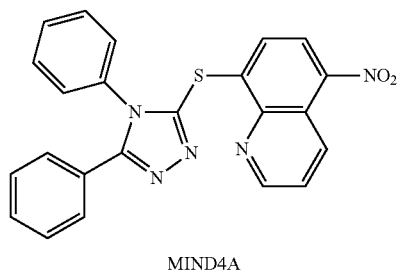 [SMILES: O=[N+]([O-])c1ccc(Sc2nnc(-c3ccccc3)n2-c2ccccc2)c2ncccc12]

MIND4A

Figure 9:
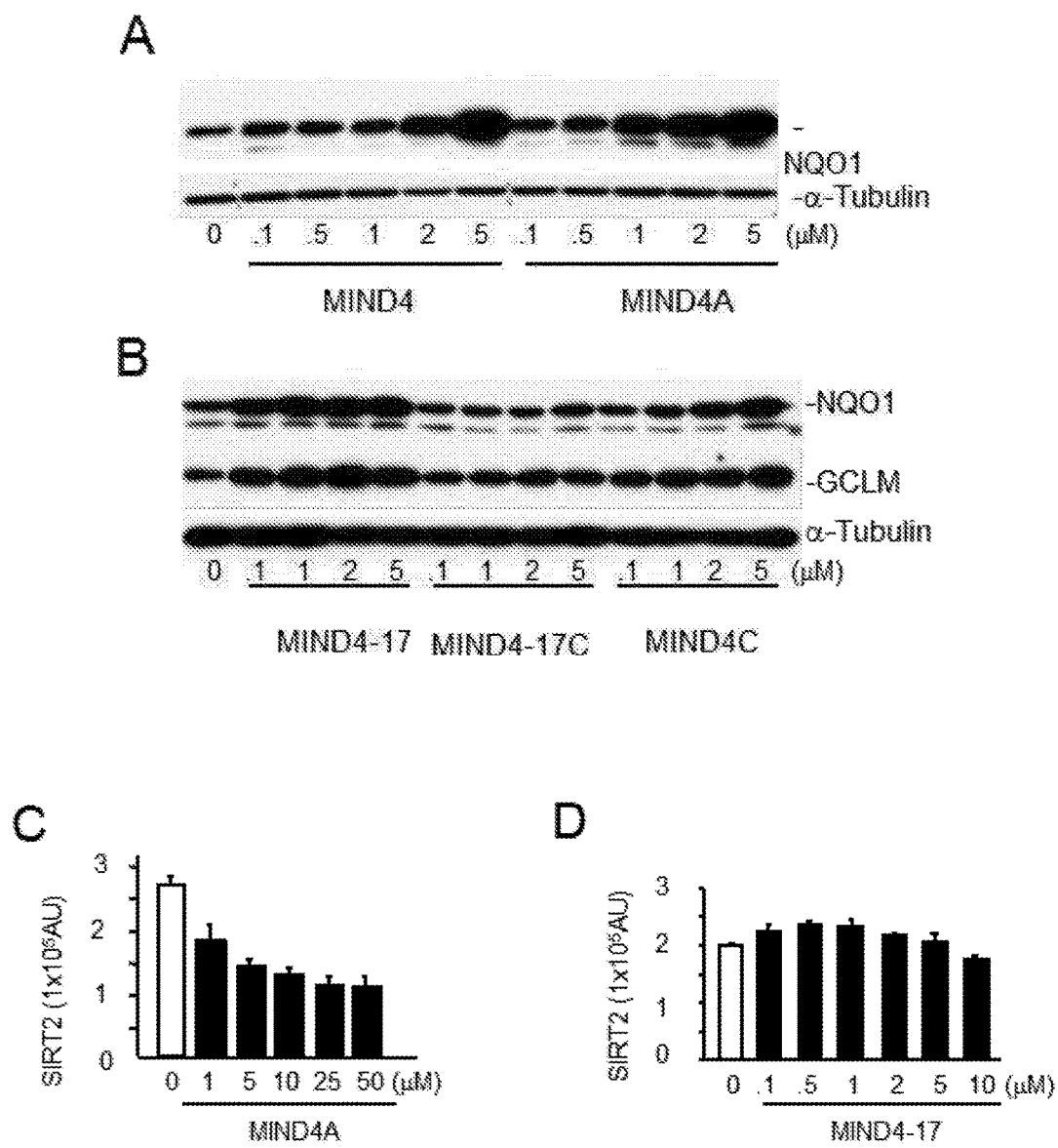
FIG. 9 provides characterization of NRF2 activation properties of MIND4 analogs.

MIND4A showed a higher potency induction of NRF2-responsive proteins NQO1 and GCLM and lower potency of SIRT2 inhibition then the parent compound, suggesting a dissociation of these two activities (FIGS. 9A and 9C). To further evaluate a structure-activity relationship of MIND4 analogues, structural analogs MIND4C, MIND4-17 and MIND4-17C were tested.

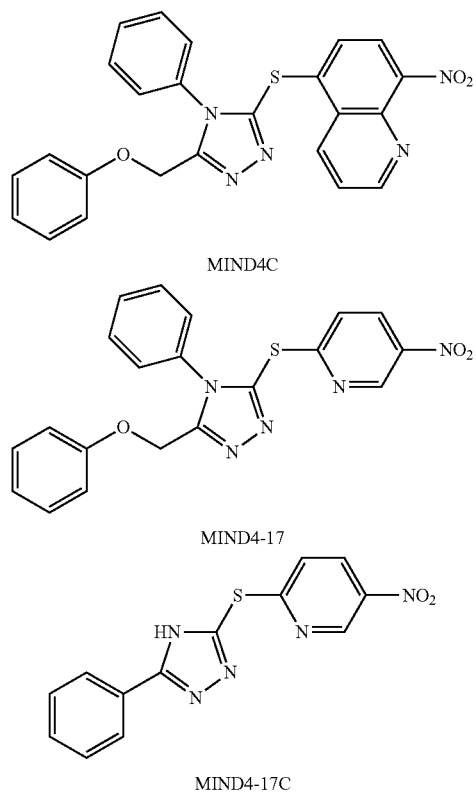

MIND4C

MIND4-17

MIND4-17C

These structural analogs have NRF2 activating properties as measured by induction of NQO1 and GCLM protein expression in differentiated ST14A cells (FIG. 9B). MIND4-17 potently induces NRF2-responses, followed by weaker activation by MIND4C, while MIND4-17C was essentially inactive. In further dose-response experiments, MIND4-17 potently induced expression of NQO1 and GCLM proteins in HD mutant and wild type ST14A cells (FIG. 10A); a known NRF2 activator dimethyl fumarate (Ellrichmann et al., 2011) was included as a reference (FIG. 10B). When tested against SIRT2 deacetylase in biochemical assay, MIND4-17 had no inhibitory activity (FIG. 9D). These results clearly show that robust NRF2 activating properties of MIND4 analogs are independent of SIRT2 inhibition activity and are due to specific properties of the structural scaffold.

The NRF2 activation properties of further MIND4 structural analogs with variable potencies of SIRT2 inhibition were tested as described previously (see Table 1) Changes in expression of the canonical NRF2-responsive proteins NQO1 and GCLM, the transcription of which was induced by MIND4, was selected as a readout of pathway activation. Protein levels of NQO1 and GCLM were examined by immunoblotting in compound treated mutant HD and wild-type ST14A cells. With the exception of MIND4, treatment with the other structural analogs, tested at a concentration range of 0.1-10 µM, did not increase NQO1 or GCLM (see Table 1), clearly demonstrating dissociation of NRF2 activation and biochemical SIRT2 inhibition properties. The results also suggested that NRF2 activation required a critical proximity of sulfur to nitrogen within an aromatic ring of MIND4 as this functionality was only present in the structure of MIND4. This hypothesis was tested using a second panel of MIND4 analogs (see Table 3).

TABLE 3

| Compound ID | Structure | SIRT2 IC50 | NQD1 CD |
|---|---|---|---|
| MIND4 | 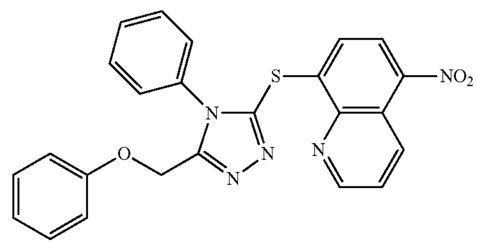 [SMILES: O=[N+]([O-])c1ccc(Sc2nnc(COc3ccccc3)n2-c2ccccc2)c2ncccc12] | 3.5 µM | 1.3 µM |
| MIND4A | 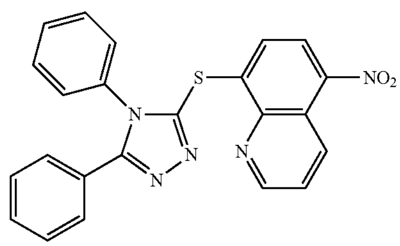 [SMILES: O=[N+]([O-])c1ccc(Sc2nnc(-c3ccccc3)n2-c2ccccc2)c2ncccc12] | 7.5 µM | 1 µM |
| MIND4B | 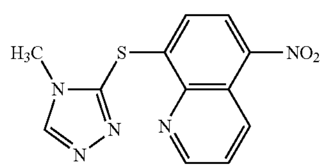 [SMILES: Cn1cnnc1Sc1ccc([N+](=O)[O-])c2cccnc12] | >50 µM | 2 µM |
| MIND4C | 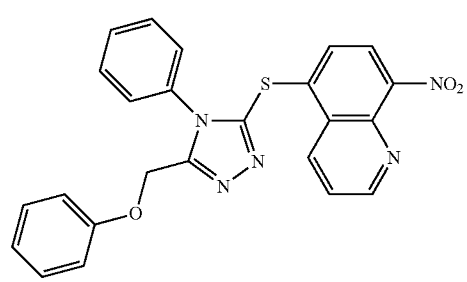 [SMILES: O=[N+]([O-])c1ccc(Sc2nnc(COc3ccccc3)n2-c2ccccc2)c2cccnc12] | >20 µM | 5 µM |
| MIND4-17 | 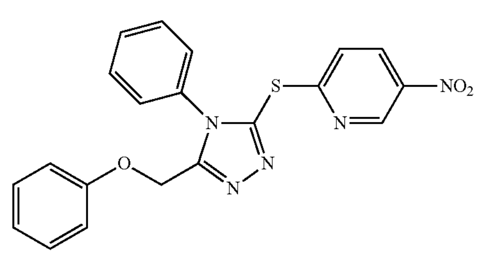 [SMILES: O=[N+]([O-])c1ccc(Sc2nnc(COc3ccccc3)n2-c2ccccc2)nc1] | >50 µM | 0.15 µM |

TABLE 3-continued

| Compound ID | Structure | SIRT2 IC50 | NQD1 CD |
|---|---|---|---|
| MIND4-17-3 | 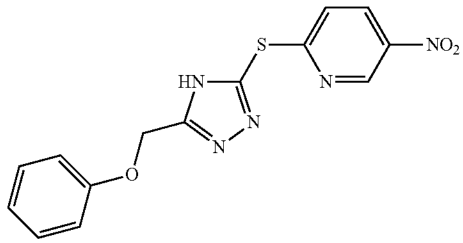 [SMILES: O=[N+]([O-])c1ccc(Sc2nnc(COc3ccccc3)[nH]2)nc1] | >50 μM | 7.5 μM |
| MIND4-17-15 | 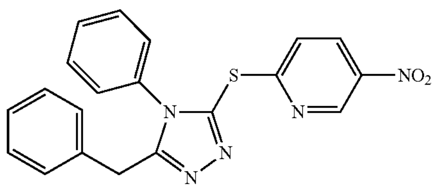 [SMILES: O=[N+]([O-])c1ccc(Sc2nnc(Cc3ccccc3)n2-c2ccccc2)nc1] | >50 μM | 0.3 μM |
| MIND4-17-33 | 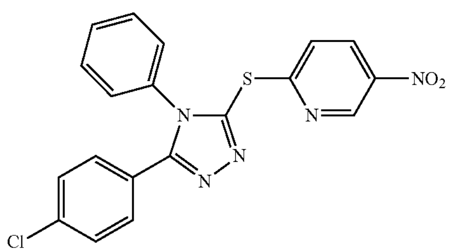 [SMILES: O=[N+]([O-])c1ccc(Sc2nnc(-c3ccc(Cl)cc3)n2-c2ccccc2)nc1] | 7.5 μM | 0.3 μM |
| MIND4-17-56 | 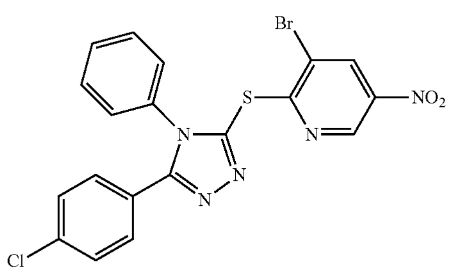 [SMILES: O=[N+]([O-])c1cnc(Sc2nnc(-c3ccc(Cl)cc3)n2-c2ccccc2)c(Br)c1] | 0.75 μM | 2.5 μM |
| MIND4-11 | 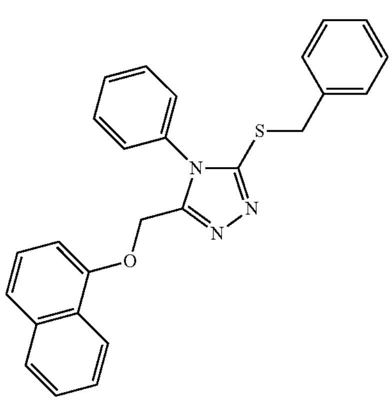 [SMILES: c1ccc(CSc2nnc(COc3cccc4ccccc34)n2-c2ccccc2)cc1] | 4.5 μM | >10 μM |

TABLE 3-continued

| Compound ID | Structure | SIRT2 IC50 | NQD1 CD |
|---|---|---|---|
| MIND4-21 | (structure: 4-phenyl-3-((4-nitrobenzyl)thio)-5-(phenoxymethyl)-4H-1,2,4-triazole) | 10 μM | ND |

Figure 20A:
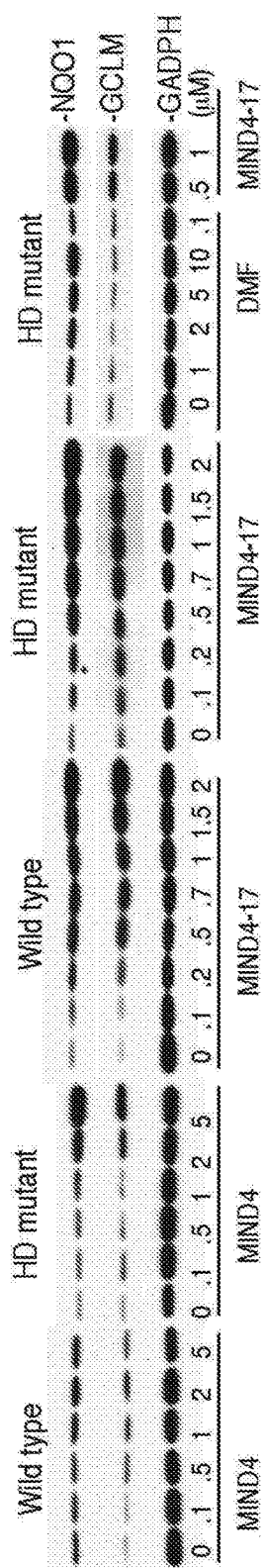
FIG. 20A shows induction of NRF2 responsive proteins NQO1 and GCLM by MIND4 and MIND4-17 in differentiated HD mutant and wild type rat embryonic ST14A cells. The effect of DMF, a known inducer of NRF2, is shown for comparison. Levels of α-tubulin were used as loading control. B) Dose-response effects of MIND4 analogs, DMF and sulforaphane (SFP) in a quantitative NQO1 inducer bioassay in Hepa1c1c7 cells. Cells grown in 96-well plates were exposed to serial dilutions of each compound for 48 hr, and the NQO1 enzyme activity was determined in cell lysates. Results are shown as average values of 8 replicate wells. The standard deviation in each case was less than 5%.

The structural analog MIND4-17 was the most potent inducer, which was significantly more potent than the clinically-approved NRF2 activator dimethyl fumarate (DMF) (FIG. 20A).

Figure 20B:
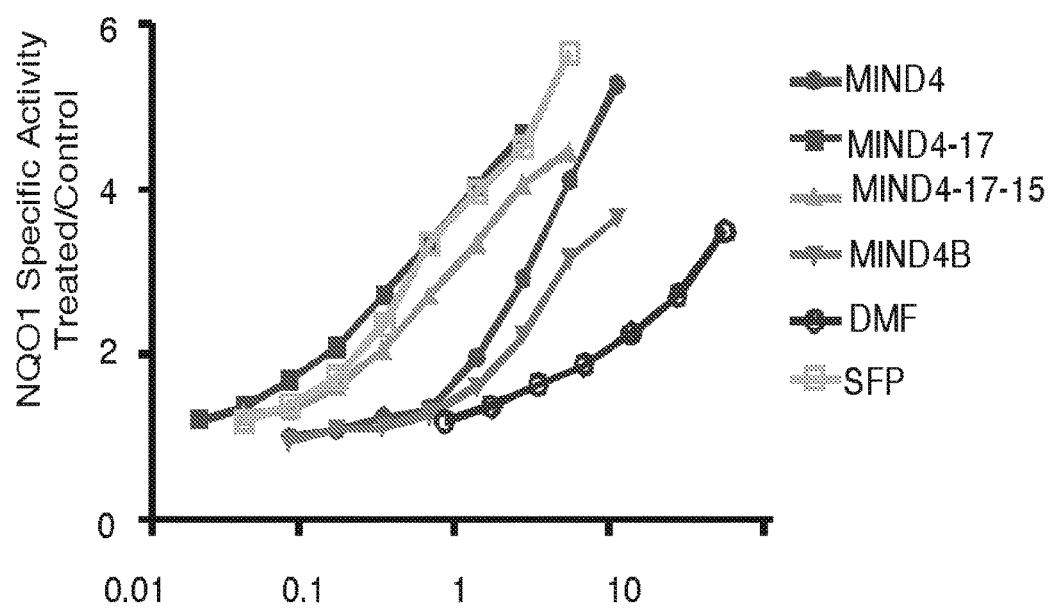

Next, using a quantitative NQO1 inducer bioassay in murine Hepa1c1c7 cells and the CD value (Concentration which Doubles the specific activity of NQO1) as a measure of potency (see Table 2), the activities of the MIND4 analogs were tested and ranked. MIND4-17 (CD=0.15 μM) displayed the highest potency, comparable to sulforaphane (SFP), the most potent naturally-occurring inducer known (CD=0.18 μM) (FIG. 20B). The parent MIND4 (CD=1.3 μM) was less potent than MIND4-17, yet each was significantly more potent than dimethyl fumarate (DMF) (CD=9 μM). Strikingly, there was no correlation between potency of NRF2 activation and inhibition of SIRT2 deacetylase activity. Furthermore, the most potent NRF2 inducer, MIND4-17, had no detectable SIRT2 inhibition activity within the tested range of 0.1-10 μM.

Example 13—Treatment Effects of NRF2 Activators on HD Neurons

Figure 11A:
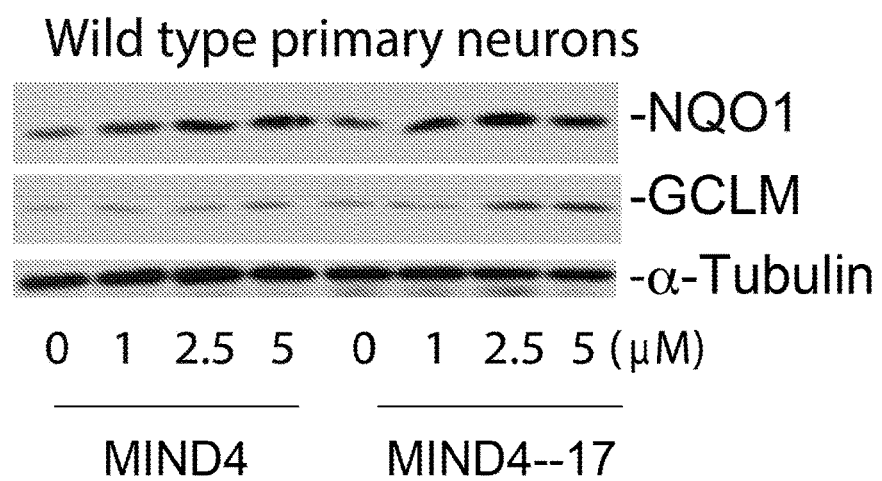
FIG. 11A shows the dose-dependent induction of NRF2-responsive proteins NQO1 and GCLM by MIND4 and MIND4-17 in wild type mouse cortical neurons (6 DIV). Proteins of interest were detected by immunoblotting. Levels of α-tubulin were used as loading control.

Given the NRF2 activating properties of MIND4 and MIND4-17, the effects of these compounds on neuronal NRF2 activation responses were tested and demonstrated in primary cortical neurons (DIVE) derived from wild type mice (FIG. 11A) Functional tests with primary cortical neurons from wild type (WT) and 140CAG full-length HTT knock-in (HD) mice were performed similar to experiments described above (FIG. 3A), with MIND4 and MIND4-17 (FIG. 11B-C). Cell survival was measured as MTT transformation at 10 days in vitro (DIV). Neurons were treated three times with the compounds at 4, 6 and 8 DIV at the indicated concentrations. Two independent experiments were performed with a total of 13 embryos per genotype, 6 WT and 7 HD respectively; 6 wells were used for each experimental condition (compound dose). In these back-to-back comparative tests, the treatment with both analogs MIND4 and MIND4-17 at an intermediate 0.25 μM dose resulted in enhanced survival of HD neurons, but at 0.5 μM and higher the compounds were cytotoxic. MIND4 was most effective, with even a low treatment dose 0.1 μM showing partially improved survival (FIG. 11B-C).

Figure 12:
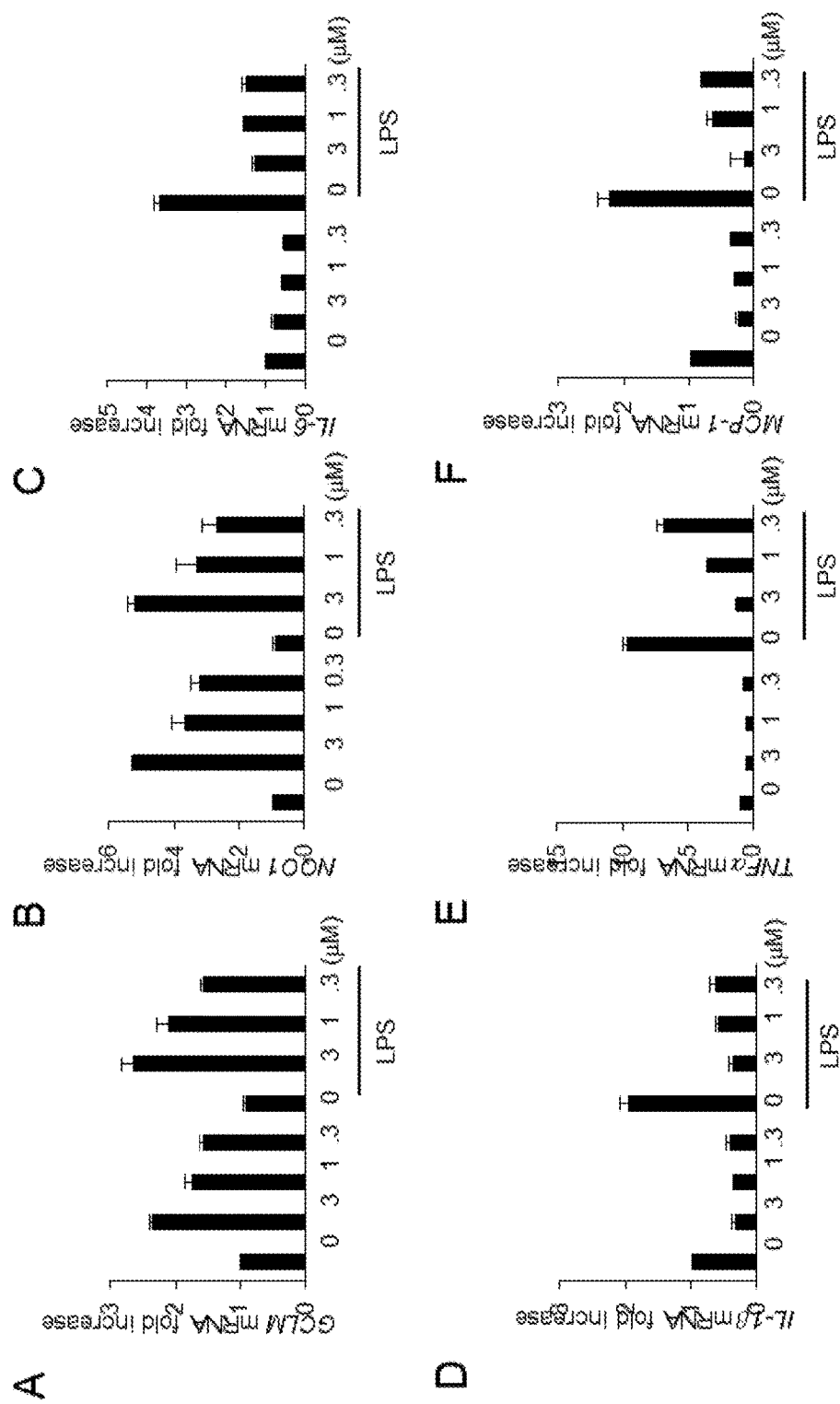
FIGS. 12A-F illustrate the NRF2 activation effects of MIND4-17 in LPS induced and non-induced BV2 microglia cells. Dose-dependent effects of MIND4-17 treatment on mRNA expression of NRF2-responsive genes GCLM (12A) and NQO1 (12B), and inflammatory factors Il-6 (12C), IL-1β (12D), TNFα (12E), and MCP-1 (12F) measured using qRT-PCR with gene-specific primers; the effects on gene expression were assessed in duplicates.
Figure 13:
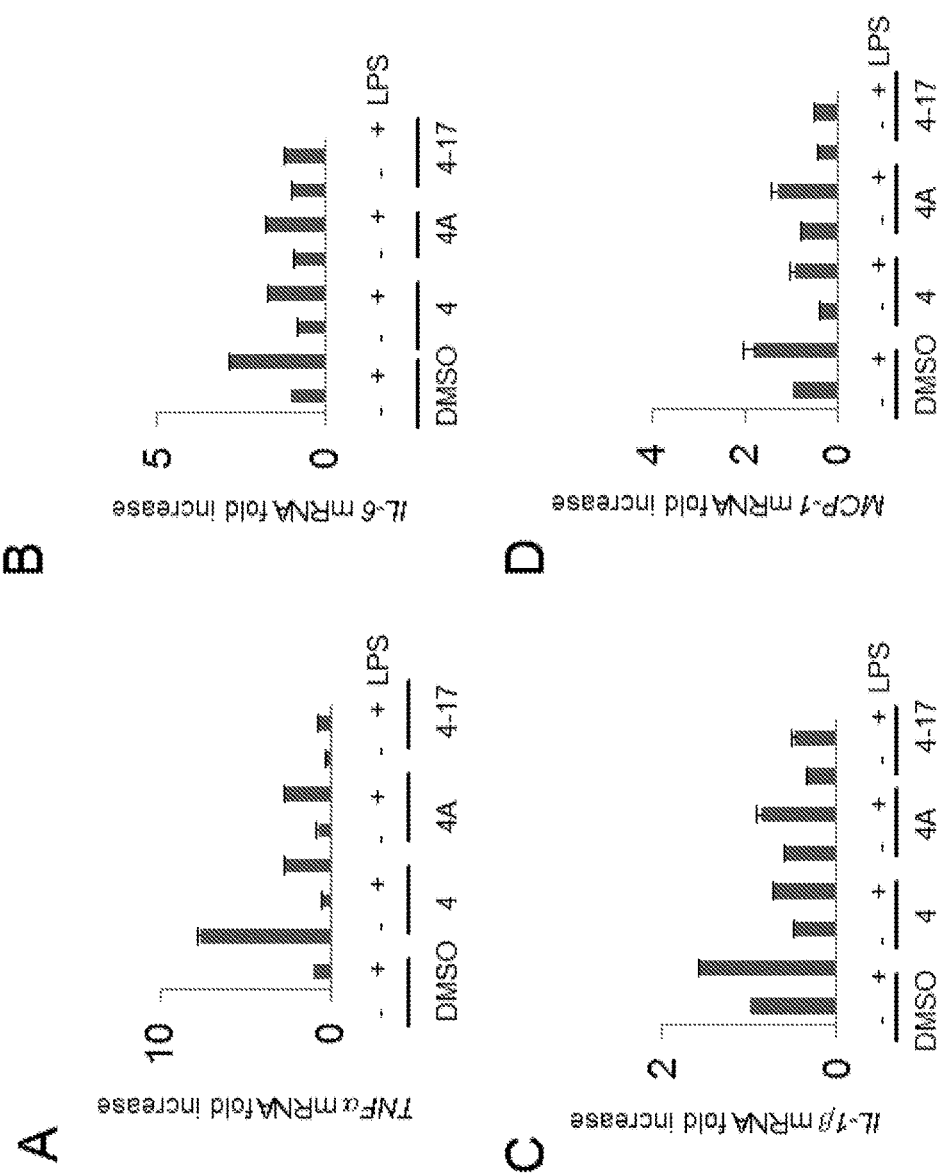
FIGS. 13A-D show comparative analysis of anti-inflammatory properties off MIND4, MIND4A, and MIND4-17 in macroglia BV2 cells. Compound effects on transcriptional expression of inflammatory factors TNFα (13A), Il-6 (13B), IL-1p (13C), and MCP-1 (13D) genes have been tested in un-induced and LPS-induced BV2 cells pre-treated with compounds at 3 µM dose for 24 hours and measured using qRT-PCR with gene-specific primers; the assessment of each gene expression was performed in duplicates.

Example 14—NRF2 Activator MIND4-17 Potently Represses Inflammation in Activated Microglia Cells Because of the pronounced effect of MIND4 on inflammatory responses, MIND4-17 was evaluated in microglia BV2 cells activated by LPS. MIND4-17 potently and in a dose-dependent manner increased transcription of GCLM and NQO1 (FIG. 12A-B) and repressed expression of inflammatory factors TNFα, IL-6, IL-1β, and MCP-1 (FIG. 11C-F). Identical results were obtained with LPS-induced iBMM macrophages treated with compound MIND4-17 (not shown). When anti-inflammatory activities of MIND4, MIND4A, and MIND4-17 were compared, the latter entity showed a superior repression of inflammatory responses in LPS-induced microglia BV2, consistent with high potency of NRF2 activation of this compound (FIG. 13A-D).

Taken together, the results demonstrate the strong potential of the NRF2-activating MIND4 scaffold and analogs to repress inflammation in vitro and in vivo.

Example 15—Modeling of the Drug Binding to Keap1 and the Induced Fit

Our collective data strongly suggests that MIND4 compounds are likely to function at an upstream regulatory arm of the NRF2/KEAP1/ARE pathway. One potential drug mechanism could involve a ligand binding to Kelch domain of KEAP1, resulting in interference of KEAP1/NRF2 interactions (Marcotte et al., 2013, Hua et al., 2013). Based on the available crystal structures of the human and mouse KEAP1 protein complex with an NRF2 peptide, the KEAP1 pocket of interest is visualized as cup-shaped upper and lower cylinder-like cavities separated by "bottleneck" in closed conformation by gate-keeping residue Arginine-415 (Agr 415) (FIG. 14A-B) (Beamer et al., 2005; Li et al., 2004; Lo et al., 2006). Side chain simulations using structural superposition of three known human KEAP1 structures suggested gate-keeping residue Arg 415 as flexible; note that Arg 415 is critical for KEAP1 interaction with NRF2 loop (Hu et al., 2013; Marcotte et al., 2013; Tong et al., 2006).

The modeling was based on eight existing crystal structures of the three human and five mouse KEAP1 proteins, while the complex structure 2flu with the peptide removed was used as the master template (PDB codes: 2flu, 1zgk, 1u6d, 3ade, 1x2j, 1x2r, 2z32, 2dyh) (Beamer et al., 2005; Li et al., 2004; Lo et al., 2006). For initial docking positions of MIND4 and MIND4-17, the study used a well-established and recently validated Internal Coordinate ligand docking protocol (Neves et al., 2012; Totrov and Abagyan, 1997). For the follow-up extensive simulations of MIND4-17 ligand, the study employed the extended protocol based on the Internal Coordinate Mechanics (ICM) method (Abagyan et al., 1994) combined with the Biased Probability sampler (Abagyan and Totrov, 1994). It included continuous rotameric distributions as implemented in the Molsoft ICM program, which permits to perform a full stochastic resampling of the vicinity of the NRF2 peptide binding site on multiple KEAP1 templates in the presence of MIND4-17 ligand. This method was used to assess ligand-induced rearrangements of potentially flexible side chains of amino acid residues within KEAP1 pocket, including Tyr 334, Ser 363, Arg 380, Arg 415, Arg 483, Ser 508, Gln 530, Ser 555, Ser 602. The model and the pose with ligand lowest binding score estimates has been calculated as described (Totrov and Abagyan, 2001). The simulations were performed from five starting points until convergence was attained as measured by inability to find a lower energy conformation for over 30,000 iterations.

Figure 14:
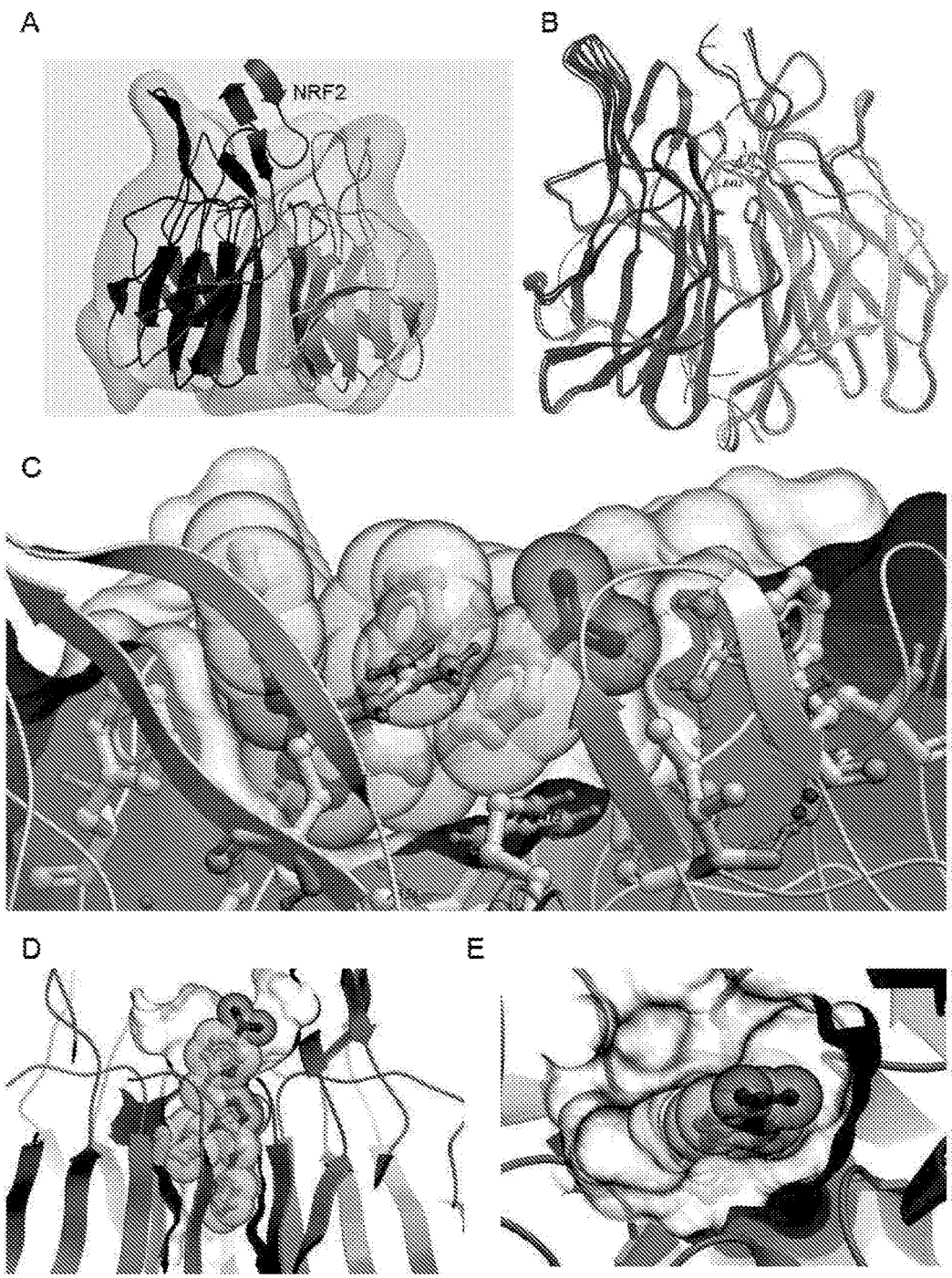
FIG. 14 shows a docking model of MIND4 and MIND4-17 binding to the KEAP1 pocket.

Initial analysis was performed without site-chain re-sampling and in the absence of NRF2 peptide. Generated by the flexible docking the ligand lowest energy conformation, compatible with both van der Waals and shape complementarity, suggested that MIND4 and MIND4-17 could bind with high affinity to the KEAP1 upper cavity (FIG. 14C). In that docking pose MIND4 ligand(s) shield Arg 415 from exposure to NRF2 loop and form hydrogen bonds with Arg 483, suggested as critical for KEAP1 binding to NRF2 (Tong et al., 2006).

The extensive docking study was continued with the most potent NRF2 activator MIND4-17. The extended Internal Coordinate Mechanics (ICM) method was used to assess a full stochastic re-sampling within the vicinity of the NRF2 binding site in the presence of MIND4-17 (Experimental Procedures). The simulation shows that MIND4-17 in relaxed extended conformation induces rearrangements of the Arg 415 side chains, which created a new cavity by changing bottleneck conformation from closed to open. MIND4-17 shows a nearly perfect complementarity to the new cavity and binds to the re-arranged KEAP1 pocket as a tight molecular plug (FIG. 14D-E). This induced fit model of MIND4-17 binding predicts shielding of critical Arg 415 and Arg 380 side chains from interaction with both ETGE and DLG binding motifs of NRF2 (Tong et al., 2006).

The docking model suggested that MIND4 and MIND4-17 are reversible inhibitors and do not bind covalently to reactive cysteines, mimicking effects of oxidative stress. The reversible binding of MIND4 and MIND4-17 to recombinant human KEAP1 protein was evaluated and confirmed by SPR (Surface Plasmon Resonance)-based Biacore assay (FIG. 15A-B).

Briefly, compound MIND4-17 and MIND4 binding to baculovirous expressed KEAP1 by Surface Plasmon Resonance (SPR) binding Biacore assay was performed by CRO Precision Antibody, Inc. Binding experiments were performed on Biacore T-200 at 25° C. using CM5 chip. Anti-GST tag antibody was immobilized by amine coupling. The ligand KEAP1 was captured until 800 RU was reached. Antigen was flowed over the chip at variable concentrations. Binding of analyte to the ligand was monitored in real time to obtain on (ka) and off (kd) rates. The equilibrium constant (KD) was calculated from the observed ka and kd. In pilot experiment the analytes MIND4 and MIND4-17 were flowed over the chip at 3 different concentrations as indicated and kinetic analysis was performed. Full kinetic analysis was performed for MIND4-17 using analyte concentrations of 140 µM (the saturating amount) and run at serial dilutions 70, 35, 17.5, 8.75, 4.375 and 0. Chi square ($\chi^2$) analysis was carried out between the actual Sensorgram (colored line) and the sensorgram generated from the BIAnalysis software (black line) to determine the accuracy of the analysis. ($\chi^2$) value within 2-1 is considered significant (accurate) and below 1 is highly significant (highly accurate). The flow rate used for capturing the ligand was 10 ml/min and the flow rate for kinetics analysis was 30 ml/min. The Biacore binding assay was performed using assay buffer: 10 mM HEPES buffer (pH 7.4), 150 mM NaCl, 3 mM EDTA, 0.005% P20 (polyoxyethylenesorbitan), 5% DMSO; regeneration buffer: 10 mM HEPES buffer (pH 7.4), 150 mM NaCl, 3 mM EDTA, 0.005% P20 (polyoxyethylenesorbitan), 5% DMSO; and conjugation buffer: 10 mM sodium acetate buffer (pH 4.5).

Figure 15A:
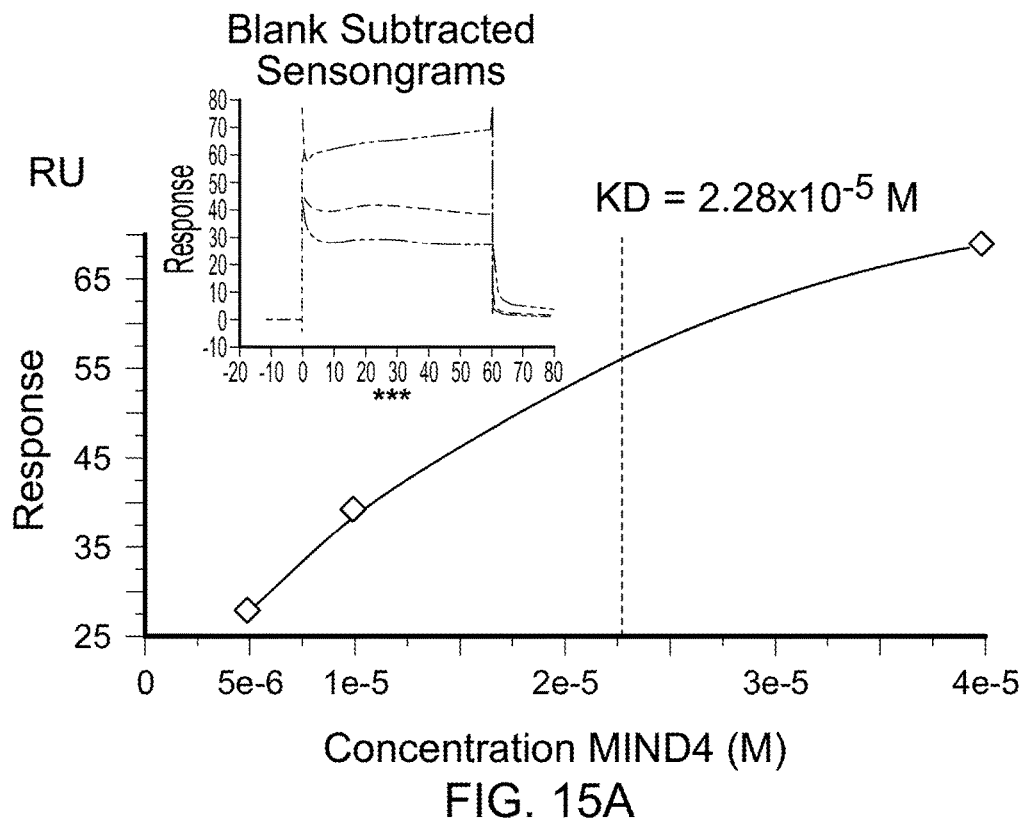
FIGS. 15A-B shows that the SPR-based (Surface Plasmon Resonance) Biacore assay confirmed reversible binding of MIND4 and MIND4-17 to KEAP1 and established $K_D=2.28\times10^{-5}(M)$ for MIND4 (15A) and determined $K_D=1.65\times10^{-5}(M)$ for MIND4-17 (15B) by full kinetic analysis; chi square $(\chi^2)=0.445$. $\chi^2<1$ is highly significant. C) Induction of NQO1 protein in differentiated HD ST14A cells with MIND4-17-33 and MIND4-17-56. Levels of α-tubulin used as loading control.
Figure 15B:
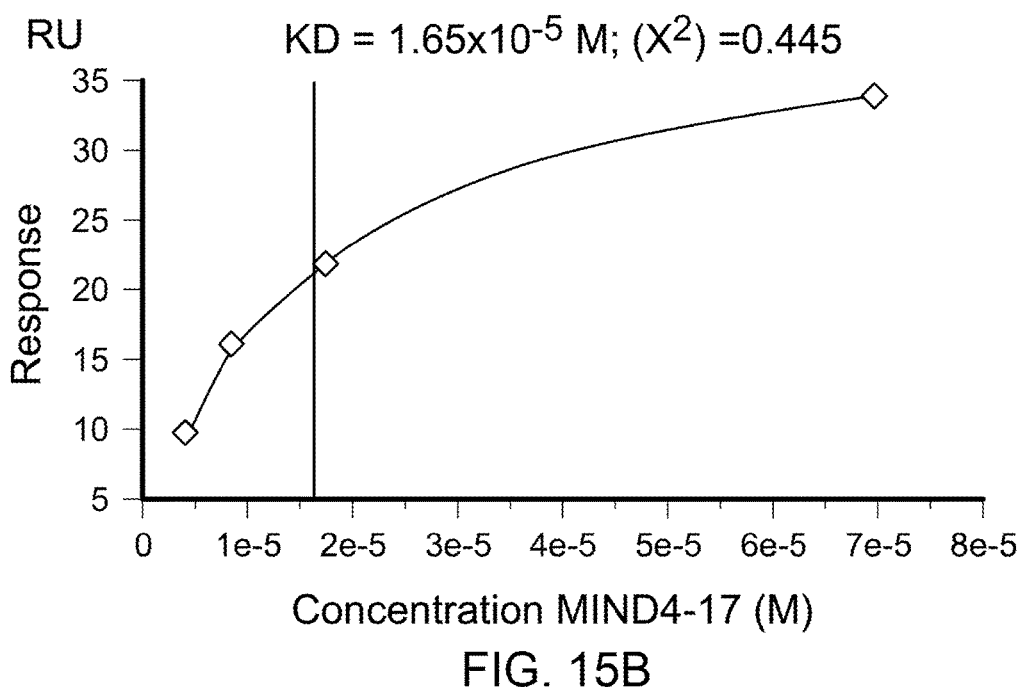
Figure 15:
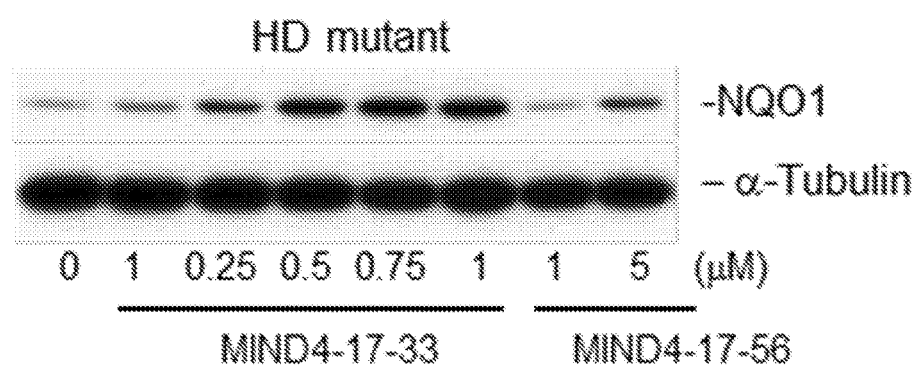
FIG. 15 shows the validation of the docking model and reversible KEAP1 binding of MIND4 and MIND4-17.

Importantly the study confirmed a reversible binding of MIND4 and MIND4-17 to KEAP1 as a proof-of-principle, supporting the validity of the docking model (FIG. 15A-B). The established $K_D=2.28\times10^{-5}$M and $K_D=1.65\times10^{-5}$M for MIND4 and MIND4-17 respectively were higher than expected from results with cell models, in which induction of NRF2 activation responses were achieved with compound doses in 0.25-2 µM range. Such discrepancy can be due to various factors including inaccurate folding of baculovirous-expressed recombinant KEAP1 protein.

To further test and validate the predictability and accuracy of the docking model, NRF2 activating properties of additional structural analogs of MIND4-17 were tested: MIND4-17-33 and MIND4-17-56.

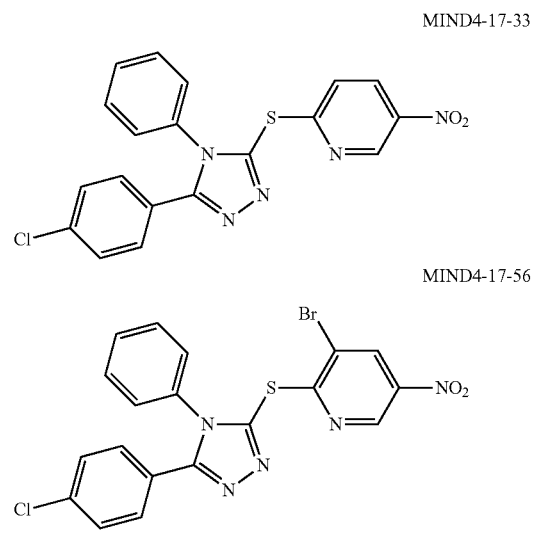

MIND4-17-33 could also adapt a similar confirmation in the KEAP1 pocket as MIND4-17, and resulted in potent induction of NQO1 protein in HD cells (FIG. 15C). In contrast, an inclusion of a Br group was expected to interfere with optimal compound binding to the KEAP1 pocket, and in accord with the model prediction, compound MIND4-17-56 had apparent lower potency in its ability to induce NQO1 than MIND4-17-33 (FIG. 15C).

While an ultimate validation by X-ray crystallography and other direct physical studies would shed additional light on the exact binding mode of MIND4 ligands, the docking model was shown already to be a good predictor and provided a framework for selection of KEAP1 inhibitors with potent NRF2 activating properties.

Example 16—Effect of MIND4-17 in Macrophages

Immortalized bone marrow derived mouse macrophages (iBMMs) and BV2 mouse microglia cell line were used in the present study. Both cell types were maintained in DMEM media supplemented with 10% FBS and antibiotic-antimycotic mix. Cells were seeded into 12 well plates at the density of $3\times10^5$ cells/well. Cells were treated with the indicated concentrations of MIND4-17 compounds for 24 hr. Cells were then stimulated with 10 ng/ml LPS (*E. coli*, Sigma) for 2 hr. Total RNA was isolated using ZR Miniprep kit (Zymo Research). 1 mg of total RNA was used to prepare cDNA. Gene expression was analyzed using VeriQuest SYBR green assay (Affymetrix) in Roche480 thermocycler. Primer sequences are as described above (see Example 9).

Figure 16:
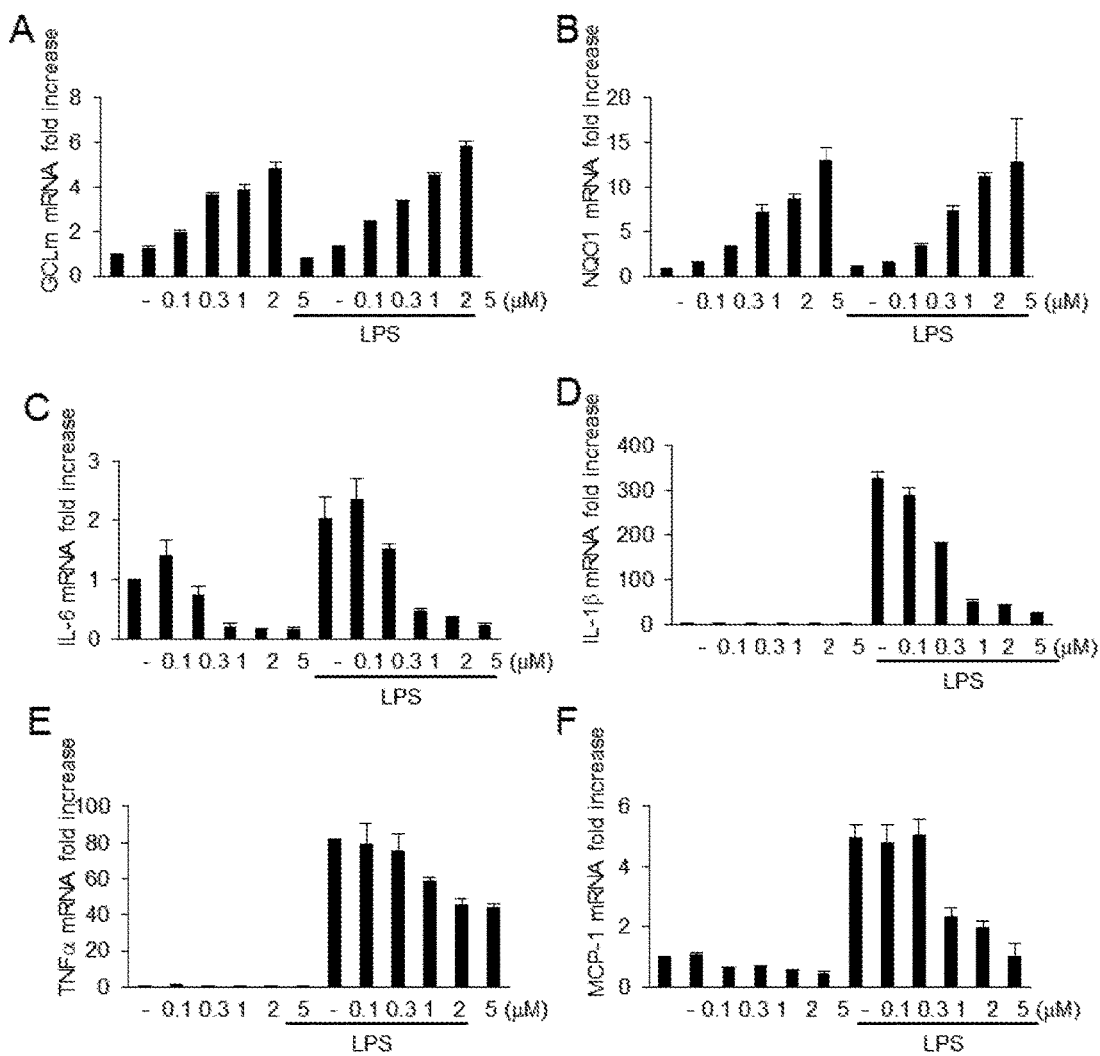
FIGS. 16A-F show the effects of MIND4-17 treatment on NRF2 activation and repression of inflammation responses in iBMM macrophages. Effects of MIND17 on transcriptional expression of NRF2-responsive GCLm (16A) and NQO1 (16B) and inflammatory 11-6 (16C), IL-1β (16D), TNFα (16E), and MCP-1 (16F) genes in un-induced and LPS-induced macrophages pre-treated with compound for 24 hours and measured using qRT-PCR with gene-specific primers.

Data from this study is shown in FIG. 16. MIND4-17 has been tested in microglia BV2 cells and iBMM macrophages activated by LPS. MIND4-17 potently and in a dose-dependent manner increased transcription of GCLM and NQO1 (FIG. 16A-B) and repressed expression of inflammatory factors TNFα, IL-6, IL-1β, and MCP-1 (FIG. 16C-F). When anti-inflammatory activities of MIND4, MIND4A, and MIND4-17 were compared in LPS-induced microglia, the latter entity showed a superior repression of inflammatory responses, consistent with high potency of NRF2 activation of this compound Example 17—HTT Clearance Effects of NRF2 activators on degradation (clearance) misfolded proteins have been tested in a rat embryonic striatal cell lines, which express either mutant (128Q) or wild type (26Q) N-terminus 546 amino acid huntingtin (HTT) fragments [Ehrlich, 2001; Quinti, 2010]. Cells were induced for neuronal differentiation and simultaneously treated with NRF2 activators in dose-dependent manner. The levels of misfolded HTT polypeptides were assessed by western analysis. The effects of NRF2 activating MIND4 analogs on reduction HTT levels have been established and found correlative with potency of induction NRF2 inducible proteins NQO1 and GCLM. FIGS. 17A-B show the effects of MIND4 and MIND4A analogs on clearance mutant and wild HTT fragments. Similar results were obtained with other MIND4 analogs, which corresponded to potency of NRF2 activation.

In effects of brain-permeable MIND4 on clearance misfloded mutant HTT fragments have been tested in HD mouse model R6/2, expressing mutant HTT exon 1 fragment. Symptomatic HD mice (5 week old) have been treated with MIND4 at 50 mg/kG daily dose for 3 weeks. Treatment effects on levels of mutant exon 1 HTT have been measured by a highly sensitive HTRF method (FIG. 17C) as described (Mosckovitch-Lopatin, 2010; Chopra, 2012). Significant reduction of mutant HTT exon I fragments were observed in cortexes of MIND4-treated R6/2 mice.

Example 18—Neuroprotection by SIRT2 Inhibitors in a Mouse Model of Parkinson's Disease SIRT2 is one of seven sirtuins that belong to the class III histone deacetylase family. In dividing cells, SIRT2 regulates mitosis and cytoskeleton dynamics. In post-mitotic neurons, a growing body of evidence indicates a broad role of SIRT2 in neuronal death and survival across different models of neurological disorders including Parkinson's disease (PD). Previous data demonstrated that genetic and pharmacological inhibition of SIRT2 rescues α-synuclein toxicity in human neuroglioma cells and it protects against α-synuclein toxicity in primary midbrain cultures as well as in a *drosophila* model of PD. The present study investigates the neuroprotective potentials of CPD4 (aka MIND4) in a well-established mouse MPTP (1-methyl-4-phenyl-1,2,3,6-tetrahydropyridine) model of PD. The toxin causes inhibition of mitochondrial activity and specific neurodegeneration of dopaminergic neurons, for example, in a mimic of that which occurs during Parkinson' disease. Comprehensive behavioral, neurochemical, and neuropathological measures were assessed.

Male C57BL/6 mice (~25 g) from Charles River Laboratories, Wilmington, Mass. were housed in temperature- and humidity-controlled rooms with a 12 hr dark: light cycle and had free access to food and water. Subacute MPTP paradigm (20 mg/kg i.p. injection once daily for 4 days) was employed to test dose response of MIND4 at 30 mg/kg, 60 mg/kg, or 90 mg/kg (i.p. 10 min before and 50 min after each MPTP injection). The effective dose of 60 mg/kg was used in the subsequent experiments (i.p. 10 min before and 50 min after each MPTP injection). Control animals received saline (control for MPTP) and 10% propylene glycol and 90% dextrose as vehicle for MIND4 by i.p. Mice were sacrificed 7 days after the last MPTP administration and striatal DA and metabolite HVA were determined by high performance liquid chromatography (HPLC) coupled with electrochemical detection (ECD) Immunostaining for tyrosine hydroxylase (TH), a marker for dopaminergic neurons was performed using mouse anti-TH antibody (Sigma, ST. Louis, Mo.). Total numbers of TH positive neurons in the substantia nigra (SN) were counted under blinded conditions using the Bioquant Image Analysis System (R&M Biometrics, Nashville, Tenn.).

Figure 18:
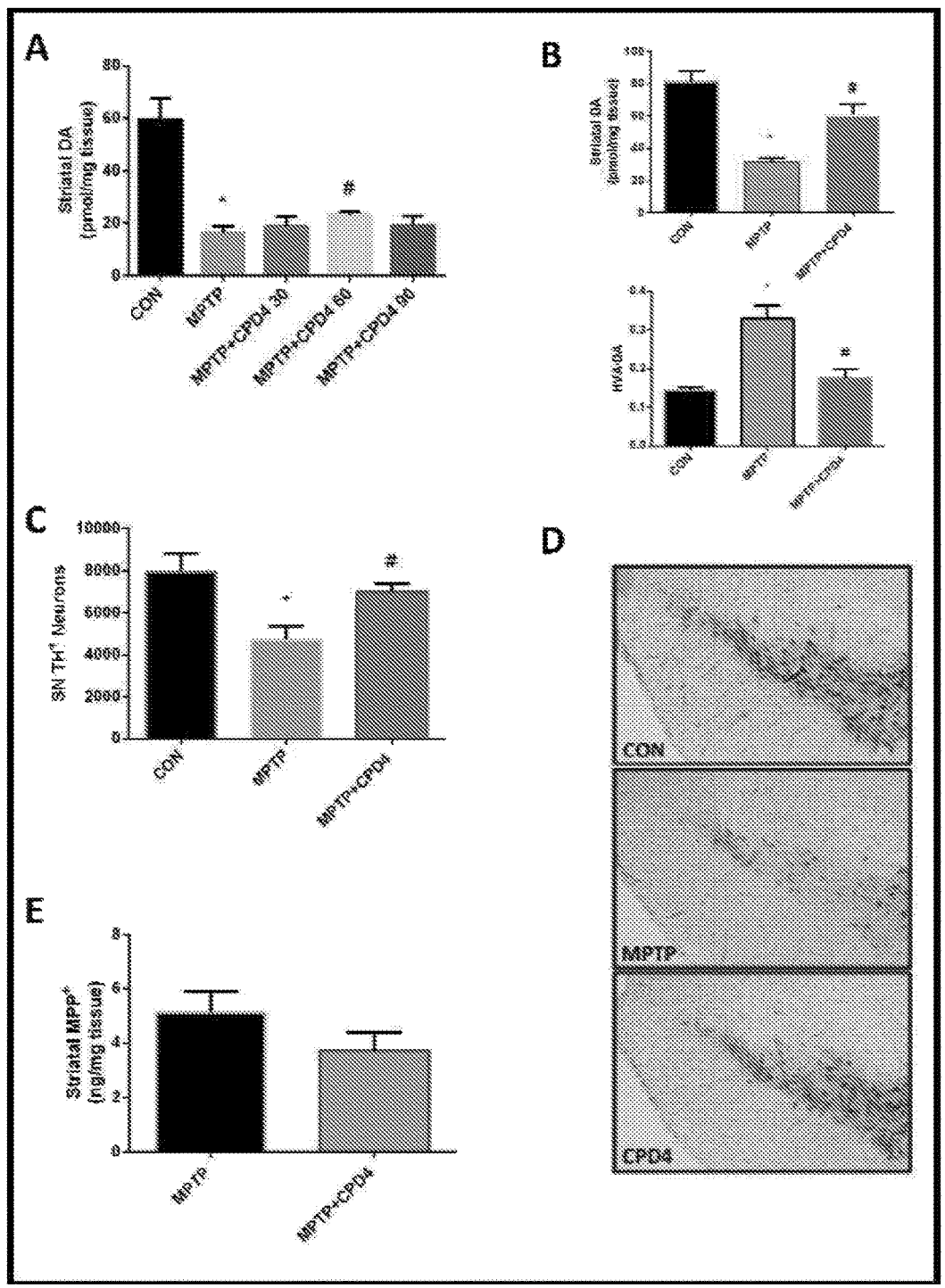
FIG. 18 illustrates CPD4 protects dopaminergic neurons in MPTP mouse model of PD. Mice were treated with MPTP at 20 mg/kg once daily for 4 days and sacrificed 5 days after the last injection (FIGS. 18A-D), or at 40 mg/kg once and sacrificed 90 min after (FIG. 18E). CPD4 was injected i.p. 10 min before and 50 min after MPTP administration. Striatal DA and metabolites (FIGS. 18A-B), MPP+ (FIG. 18E) were detected by HPLC-ECD. Nigral dopaminergic neurons were counted by stereological analysis of TH positive neurons (FIGS. 18C-D). (*p<0.05 vs. CON; # p<0.05 vs. MPTP).

The protective effects of CPD4 have been confirmed in both acute and subchronic PTP paradigms by comprehensive behavioral, neurochemical, and neuropathological evaluations (FIG. 18). CPD4 was administrated i.p. at 20 mg/kg 10 min before and 50 min after MPTP 20 mg/kg i.p. once daily for 4 days (subchronic regimen) (FIG. 18A). High performance liquid chromatography (HPLC) coupled with electrochemical detection was used to show attenuated dopamine (DA) loss induced by MPTP in the striatum (FIG. 18B). Dopaminergic cell counts in the substantia nigra (SN) were also measured in treated mice and compared to the control (MPTP group) (FIG. 18C). Tyrosine hydroxylase (TH) immunostained dopaminergic neurons were also imaged in the SN (FIG. 18D). Increased levels of MPP$^+$, the active, toxic metabolite of MPTP were detected in the striatum of AK7 treated animals 90 min after MPTP injection (FIG. 18E).

CPD4 appeared to have a narrow effective dose window. At 60 mg/kg, it showed mild but significant protection of MPTP induced DA loss in the striatum (FIG. 18A). Separate experiments later confirmed increased level of residual DA and decreased DA turnover rate (HVA/DA) in 60 mg/kg CPD4 group in comparison to MPTP group (FIG. 18B). Stereological analysis demonstrated that CPD4 treated mice had more remaining dopaminergic neurons in the SN than MPTP alone group (FIGS. 18C-D). CPD4 does not seem to change MPTP metabolism. There is no difference in MPP+ concentration in the striatum between MPTP mice and MPTP+CPD4 mice 90 min after MPTP injection (FIG. 18E).

Figure 19:
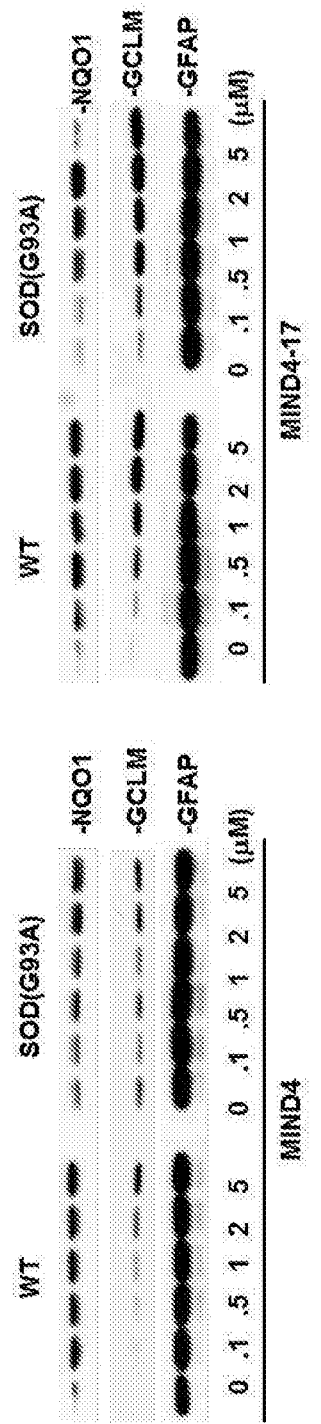
FIG. 19 shows the results of an evaluation of NRF2-activating response in wild type and ALS mutant primary astroglia cells.

Example 19—Effects of MIND4 and MIND4-17 on Activation of NRF2 Responses in Mouse Wild Type and Mutant SOD1 Primary Astroglia Cells Primary glia was derived from wild type and mutant SOD1 (G93A) mice and treated with MIND4 and MIND4-17 at indicated doses. The expression NRF2 responsive NQO1 and GCLM proteins were detected by immunochemistry. The results show that Nrf2 responses in mutant SOD1 (G93A) cells were comparable to that observed in wild type cells (FIG. 19). Importantly, compounds had no effects on human mutant SOD1 transgene, expressing in mice from human promoter.

Example 20—Evaluation of the NRF2-Activating Properties of the MIND4 Scaffold

Mouse embryonic fibroblasts (MEFs) from wild-type (WT), NRF2-knockout (NRF2-KO) or KEAP1-knockout (KEAP1-KO) mice, were cultured in plastic dishes (Invitrogen) coated for 30 min with 0.1% (w/v) gelatin before use. The cell culture medium was Iscoves Modified Dulbecco's Medium (with L-glutamine) supplemented with human recombinant epidermal growth factor (10 ng/mL), 1× insulin/transferrin/selenium, and 10% (v/v) heat-inactivated FBS, all from Invitrogen. Cells were maintained at 5% $CO_2$ in air at 37° C. For experiments, cells (250,000 per well) were grown for 24 hr on 6-well plates, and then treated with solvent control (0.1% DMSO, v/v) or compounds for either 5 hr or 24 hr. For western blot analysis, cells were washed twice with ice-cold phosphate buffered saline (PBS) and lysed in 150 µl of RIPA buffer (50 mM Tris-Cl pH 7.5, 150 mM NaCl, 0.5% sodium deoxycholate, 1% NP-40, 0.1% SDS and 1 mM EDTA), containing 1 protease inhibitor cocktail tablet (Roche) per 10 ml of buffer. Cell debris were removed by centrifugation at 16,300×g for 10 mM at 4° C., and protein concentrations were determined by the BCA assay (Thermo). Proteins were resolved by SDS/PAGE, transferred to immobilon-P membranes, and probed with specific antibodies against NQO1 (1:1000) or NRF2 (1:1000). Equal loading was confirmed by probing the blots with an antibody against β-actin (mouse monoclonal, 1:10000), from Sigma, Dorset, United Kingdom.

Figure 21:
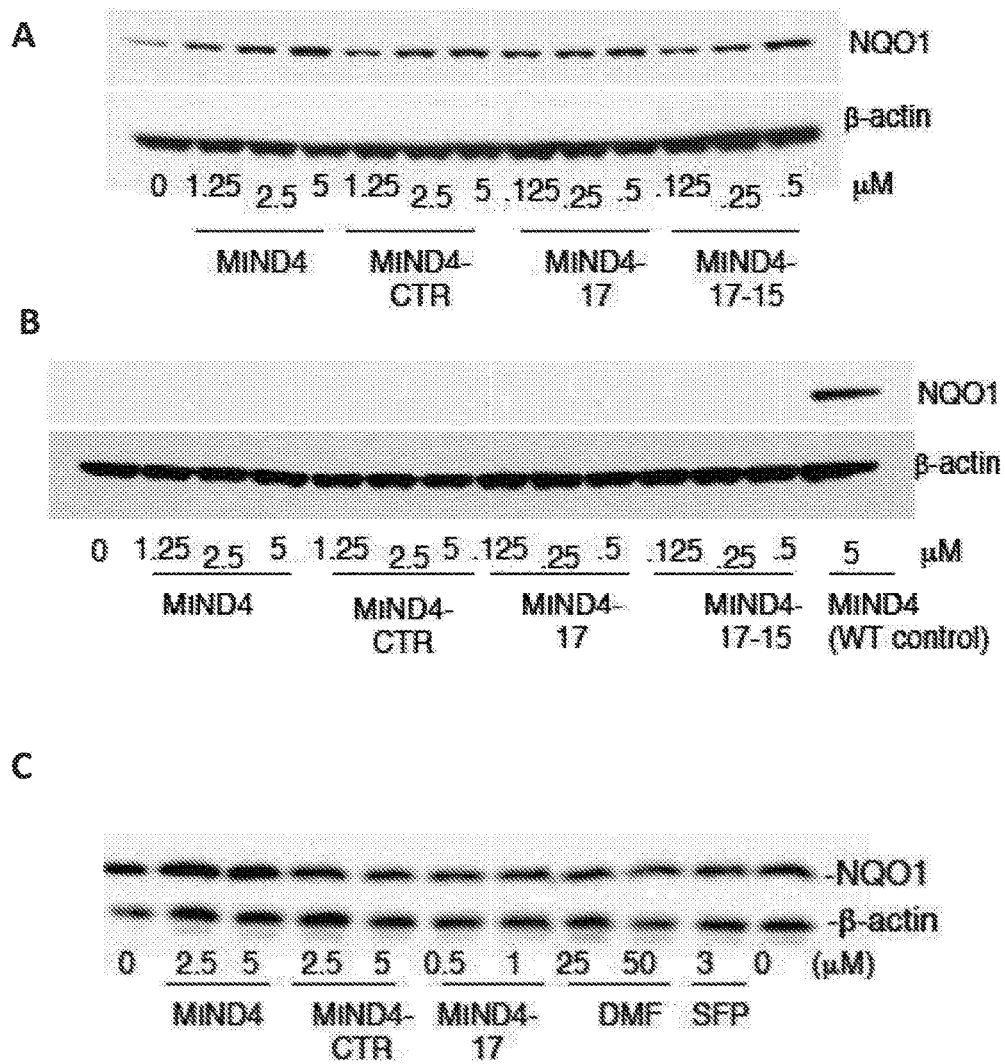
FIG. 21A) MIND4 analogs induce NQO1 in wild-type mouse embryonic fibroblasts (MEFs). The protein levels of NQO1 were detected by immunoblotting. B) Effects of MIND4 analogs on induction of NQO1 in NRF2-null (NRF2-KO) MEFs. Cell lysate from wild-type MEFs that had been exposed to MIND4 was loaded in the last lane for comparison. C) Effects of MIND4 analogs on the levels of NQO1 in KEAP1-null MEFs. b-Actin was used as a loading control.

In wild-type MEFs, MIND4 analogs increased the levels of NQO1 protein to varying degrees (FIG. 21A), while in NRF2-null cells the effects were completely lost (FIG. 21B). MIND4 analogs were further tested in KEAP1-null MEFs, in which the lack of KEAP1, the main cytoplasmic repressor of NRF2, results in stabilization and nuclear translocation of NRF2, and in constitutively high transcription of NRF2-responsive genes. Treatment with MIND4 analogs did not upregulate NQO1 expression further (FIG. 21C), suggesting that these compounds target the cytoplasmic NRF2/KEAP1 complex.

To test whether induction of NRF2-dependent enzymes is preceded by stabilization and nuclear translocation of NRF2, cells were treated with MIND4-17, the most potent NRF2 inducer in the MIND4 series, and evaluated NRF2 localization. For nuclear-cytoplasmic separation, WT MEFs (500,000 per dish) were grown for 24 hr on 6-cm plates, and then treated with solvent control (0.1% DMSO, v/v) or 0.5 µM MIND4-17. At the end of each treatment time, cells were placed on ice and washed twice with ice-cold PBS and subsequently lysed in buffer A [10 mM KCl, 5 mM $MgCl_2$, 50 mM Tris-HCl (pH 7.5), 0.5% Nonidet P-40 (Roche), 1 mM dithioretitol (DTT) (Sigma), containing one protease inhibitor tablet and one phosphatase inhibitor tablet (both from Roche) per each 10 ml of buffer]. The lysates were subjected to centrifugation (Spectrafuge 24D, Labnet) at 1,000×g for 5 min at 4° C. The supernatant (cytoplasmic fraction) was transferred to a fresh Eppendorf tube. The pellet (nuclear fraction) was washed three times in buffer A before being dissolved in buffer B [2% SDS, 150 mM NaCl, 65 mM Tris-HCl (pH 8.0)] and sonicated for 30 sec. Finally, the lysates were subjected to western blot analysis. The blots were probed with antibodies against GAPDH (rabbit polyclonal, 1:5000) and Lamin A/C (rabbit polyclonal, 1:1000, Gene Tex, Calif., United States of America) to confirm fraction purity and equal protein loading.

Figure 22:
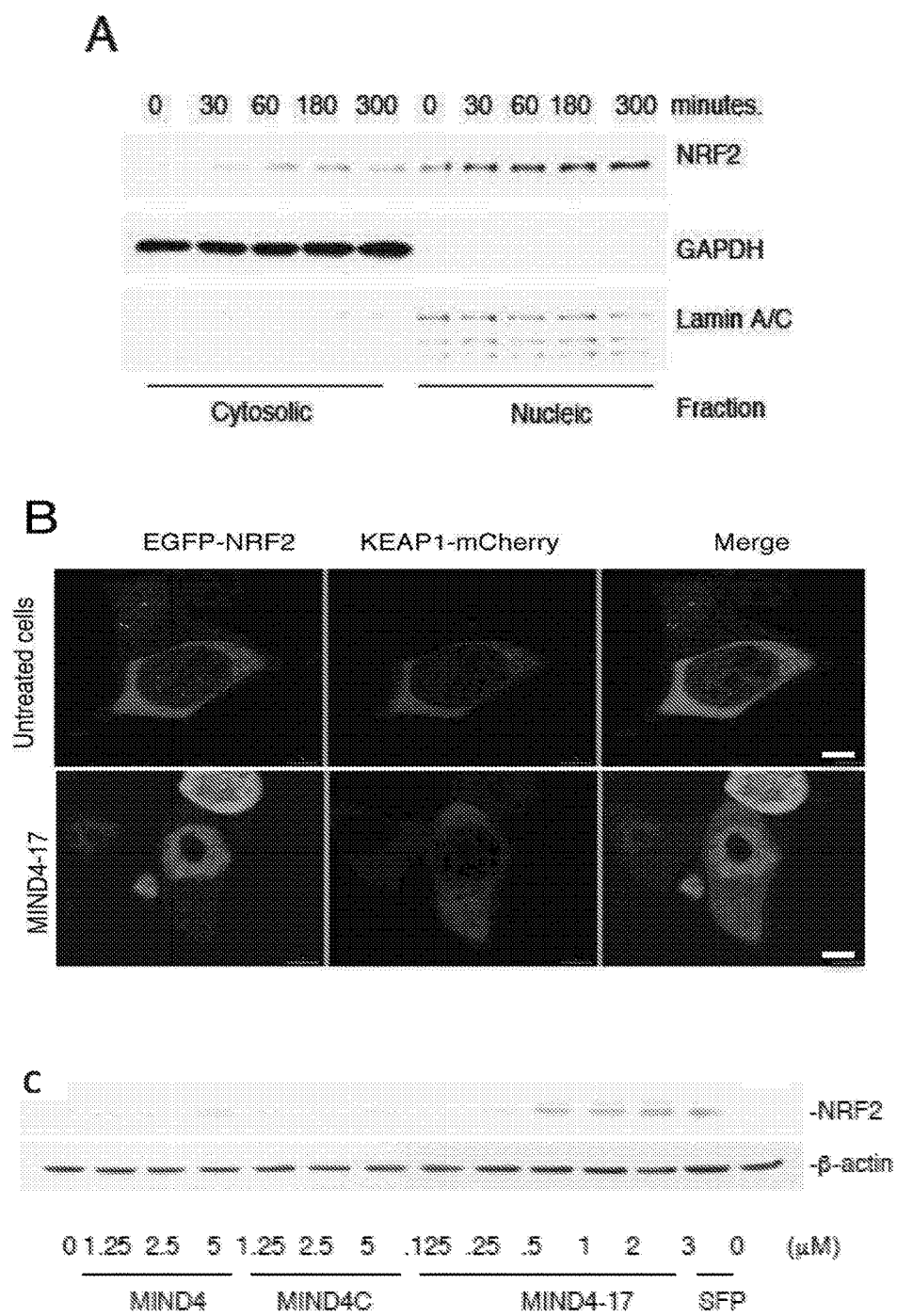
FIG. 22 NRF2 activating properties and antioxidant activity of MIND4-17. A, B) Exposure to MIND4-17 causes stabilization and nuclear translocation of NRF2. A) Time-dependent accumulation of NRF2 in nuclear fractions from wild-type MEFs treated with MIND4-17 (0.5 µM); cell lysis and biochemical fractionation were performed at indicated times after treatment. The levels of NRF2, cytoplasmic GAPDH and nuclear LAMIN AC reference controls, were detected by immunoblotting. B) Nuclear translocation of NRF2 protein in live HEK293 cells treated with MIND4-17 at 1 µM dose for 1 hr. HEK293 cells were transiently transfected with fluorescent-tagged proteins, EGFP-NRF2 and KEAP1-mCherry, and imaged 24 hr later. C) Effects of MIND4 analogs on NRF2 levels in wild-type MEFs treated with compounds for 5 hr. The levels of NQO1 and the loading control β-actin were detected by immunoblotting. Sulforaphane (SFP) was used as positive control.
Figure 23:
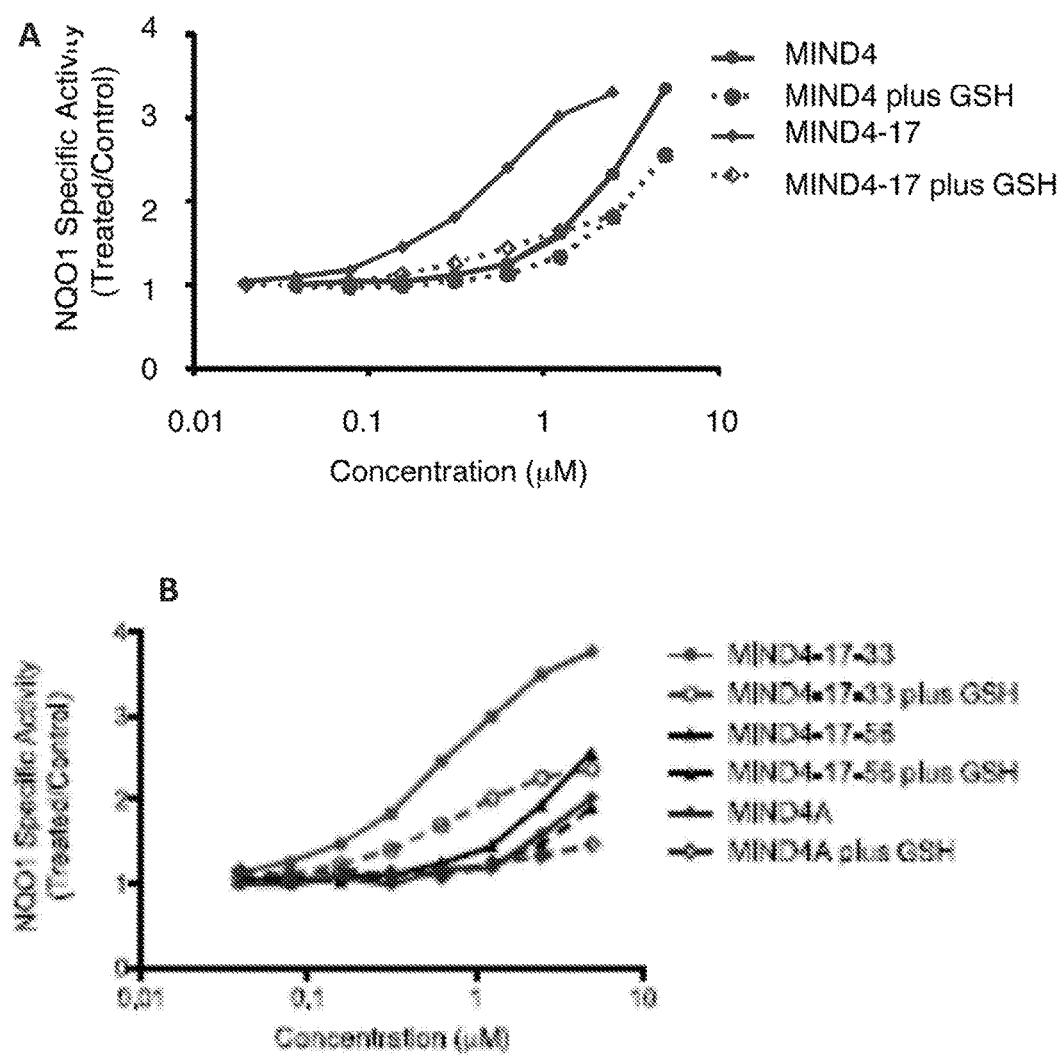
FIG. 23A shows the effect of GSH on the NQO1 inducer activity MIND4 and MIND4-17 in Hepa1c1c7 cells. Each compound was incubated in cell culture medium in the presence or absence of 1 mM GSH at 37° C. for 30 min before administering to cells grown on 96-well plates. After a 48 hr exposure, the NQO1 enzyme activity was determined in cell lysates. Results are shown as average values of 8 replicate wells. The standard deviation in each case was less than 5%.
FIG. 23B shows the effect of GSH on the NQO1 inducer activity MIND4 analogs in Hepa1c1c7 cells. Each compound was incubated in cell culture medium in the presence or absence of 1 mM GSH at 37° C. for 30 min before administering to cells grown on 96-well plates. After a 48 hr exposure, the NQO1 enzyme activity was determined in cell lysates. Results are shown as average values of 8 replicate wells. The standard deviation in each case was less than 5%.

An increase of NRF2 levels was detected in nuclear and also in cytoplasmic fractions as early as 30 min after cell exposure to MIND4-17 (0.5 µM), and NRF2 remained elevated for at least 5 hr (FIG. 22A). In parallel, live-cell imaging of human HEK293 cells expressing EGFP-NRF2 and KEAP1-mCherry fusion proteins confirmed the stabilization and nuclear translocation of EGFP-NRF2 after exposure to MIND4-17 (1 µM) for 1 hr (FIG. 22B). Consistent with compound potencies, accumulation of total NRF2 protein was readily detectable in wild-type MEFs after 5 hr exposure with SFP and MIND4-17 and to much lesser extent with MIND4 and MIND4C (FIG. 22C).

The absolute requirement for a sulfur in proximity with electron-deficient aromatic systems in the structures of the active MIND4 analogs suggested that these compounds could be chemically reactive with cysteine nucleophiles. Inducer potency was quantified by use of the NQO1 bioassay in Hepa1c1c7 cells as described [Prochaska, 1988]. To examine the effect of GSH on inducer potency, compounds were incubated in cell culture medium containing 1 mM GSH at 37° C. for 30 min before cell treatment.

To examine the effect of MIND4-17 on the stabilization and sub-cellular localization of NRF2 in live cells, HEK293 cells (200,000 per dish) grown in α-MEM supplemented with 10% heat-inactivated FBS on 6-cm glass dishes, were co-transfected with constructs encoding EGFP-NRF2 and KEAP1-mCherry using Lipofectamine 2000 (Invitrogen) as described [Baird, 2013]. Cells were imaged 24 hr post-transfection before and after 1 hr-exposure to 1 µM MIND4-17. All images were acquired by confocal microscopy using a laser-scanning confocal microscope (LSM780; Carl Zeiss). The microscope was equipped with a thermostated chamber suitable to maintain the live cells and optics at constant 37° C. Imaging was performed using a 63× oil immersion NA 1.4 Plan-Apochromat objective from Zeiss.

Without being bound by theory, it was believed that if a compound was able to react with a cysteine, such compound will form a conjugation product with the cysteine of GSH during the pre-incubation time in cell-free medium, and thus the concentration of the free MIND4 analog that is available for binding to the cysteine sensors of KEAP1 will be lower, and consequently, its inducer potency will be reduced. Furthermore, analogs with higher cysteine reactivity will react faster with GSH, and therefore the effect of GSH on their inducer potency is expected to be greater. Indeed, we found that pre-incubation with GSH drastically reduced the potency of MIND4-17 but had a much less pronounced effect on the activity of the less potent MIND4 (FIG. 4C), suggesting a correlation between cysteine reactivity and inducer potency. This conclusion was further strengthened by the finding that, similar to MIND4-17, the activity of a highly potent inducer MIND4-17-33 (CD=0.3 µM) was significantly affected by pre-incubation with GSH, whereas the effect of GSH was much more modest on the activities of the weaker MIND4-17-56 (CD=2.5 µM) and MIND4A (CD=1 µM) analogs (Fig. S3D). Together with the microarray analysis showing that all affected cellular pathways are related to the activity of NRF2, these data suggests that KEAP1 is the major intracellular target for the MIND4 scaffold.

Example 21—ARE Transcriptional Assays in Primary Corticostriatal Neuronal Co-cultures Primary corticostriatal neuronal co-cultures were prepared from E18 mouse brains as previously described [Kaltenbach, 2010]. Mice were maintained in accordance with Duke University Medical Center Institutional Animal Care and Use Committee guidelines. For 5×-ARE-luciferase reporter assays, neurons were transfected following their isolation (Nucleofector, Lonza) with 2.5 µg Cignal Antioxidant Response Reporter dual luciferase plasmids (Qiagen/SABiosciences) and plated onto pre-established glial beds in 96 well plates. After 4 days in culture at 37° C. under 5% $CO_2$, co-cultures were treated with the indicated compounds for 4 hr or 16 hr then harvested and read for luminescence from firefly and Renilla luciferases according to the Dual Glo luciferase protocol (Promega) using a SpectraMaxL luminometer (Molecular Devices). Each sample was measured in technical triplicate. For quantitative RT-PCR (qPCR) of ARE target genes, corticostriatal co-cultures were prepared as described above and, after 4 days in culture, treated for 6 hr with the indicated compounds followed by RNA harvesting according to the Absolutely RNA miniprep protocol (Agilent Technologies). Purified RNA was converted to cDNA using random hexamers and SuperScript First-Strand RT-PCR Synthesis (Invitrogen). Resulting cDNA samples were used for qPCR using Power SYBR Green (Applied Biosystems) and the ViiA 7 qPCR System (Applied Biosystems). $C_t$ values were determined using primer sets against ARE genes Hmox1, Gclc and Nqo1]. Each sample was run in technical triplicate and relative expression expressed as fold-change over control after normalizing each sample to $C_t$ values for GAPDH.

Figure 24:
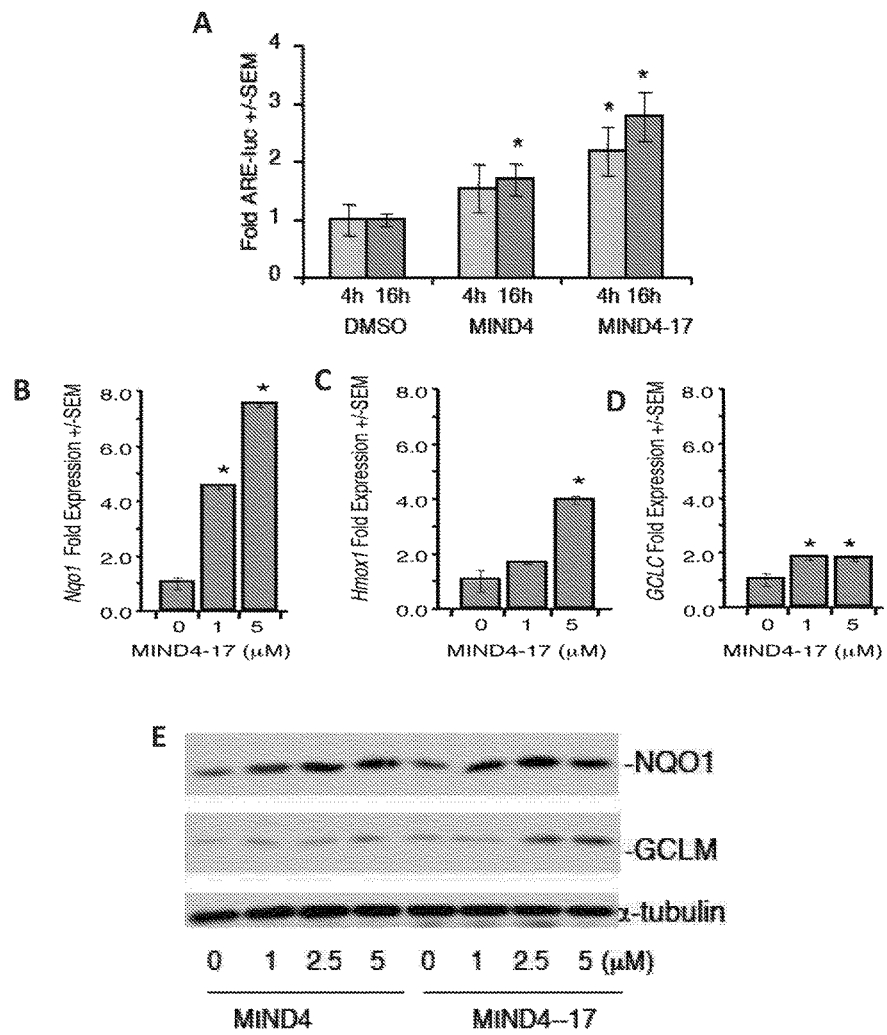
FIG. 24A) Treatment of corticostriatal co-cultures with 5 µM MIND4 and MIND4-17 induced time-dependent increases in the transcriptional rate of a 5x-ARE promoter-luciferase reporter. *=p<0.05 (Student's t-test with respect to DMSO-only controls). B-D) MIND4-17 induces a concentration-dependent increase in transcription of the ARE genes Nqo1 (B), Hmox1 (C) and to a lesser degree Gclc (D) as quantified by qPCR. *=p<0.05 (Student's t-test with respect to DMSO-only controls ("0"). E) Dose-dependent induction of NRF2-responsive proteins NQO1 and GCLM by MIND4 and MIND4-17 in wild type mouse cortical neurons (6 DIV). Proteins of interest were detected by immunoblotting. Levels of α-tubulin were used as loading control.

As shown in FIG. 24A, both MIND4-17 and MIND4 were able to induce increases in the transcriptional rate of a 5×-ARE promoter-luciferase reporter construct transiently transfected into these corticostriatal co-cultures. The superior induction of ARE-dependent transcription by MIND4-17 was entirely consistent with the established higher potency of the former compound. Next, we asked directly whether activation of ARE-dependent transcription by MIND4-17 resulted in increased expression levels for known NRF2-target genes. In fact, treatment with MIND4-17 for 6 hr increased the expression of the canonical ARE genes Nqo1, Hmox1 (heme oxygenase 1), and to a lesser degree (~2 fold) Gclc (FIG. 24B, C, D). Dose-response induction of NRF2-target proteins NQO1 and GCLM in wild type mouse cortical neurons (6 DIV) treated with MIND4 and MIND4-17 for 24 hr was consistent with the compound effects on ARE-dependent gene transcription (FIG. 24E). MIND4 and MIND4-17 increased the expression of NQO1 protein to the same extent, but the latter compound was a more potent inducer of GCLM expression.

Example 22—ROS Detection Assay

Elevated levels of reactive oxygen species (ROS) have been implicated in normal brain aging and in the pathogenesis of numerous neurodegenerative diseases, including HD. The neuroprotective properties of NRF2 activation have been reported to boost antioxidant defenses in astrocytes, but in this study it was determined whether NRF2 induction mediates protective antioxidant activity in mutant Htt expressing primary neurons. It was determined whether NRF2 activation could reduce mHtt associated ROS in primary neurons isolated from embryonic brains (E15-E17) of HD140CAG mice, which display strikingly elevated ROS levels compared to cells derived from wild type mice. HD and wild type neurons were treated with MIND4-17 at 0.1 µM and 0.25 µM doses for 4 days, and ROS were measured.

ROS detection in primary neurons was performed as previously described by [Valencia, 2013]. Briefly, neurons were plated on glass coverslips pretreated with poly-L-lysine for 24 hours. At 4 DIV wild type and HDQ140 neurons were treated with compound MIND4-17 at 4 DIV, then ROS were measured in live cells at 8 DIV. Prior to ROS measurements, neurons were loaded with 2 mM of the non-fluorescent ROS-detector carboxy-DCFDA-AM (Invitrogen) for 15 min at 37° C. Cells were washed three times with pre-warmed PBS and the coverslip was mounted in a stage top incubation system INU-NI-F1 (Tokai Hit Co.) with controlled temperature at 37° C. Images of live neurons were obtained using a Bio-Rad Radiance 2100 confocal laser-scanning microscope with krypton-argon laser. Images were acquired through a 60× oil immersion Nikon Apo objective DIC H (NA 1/4 1.4) and quantified using ImageJ software (NIH).

Figure 25:
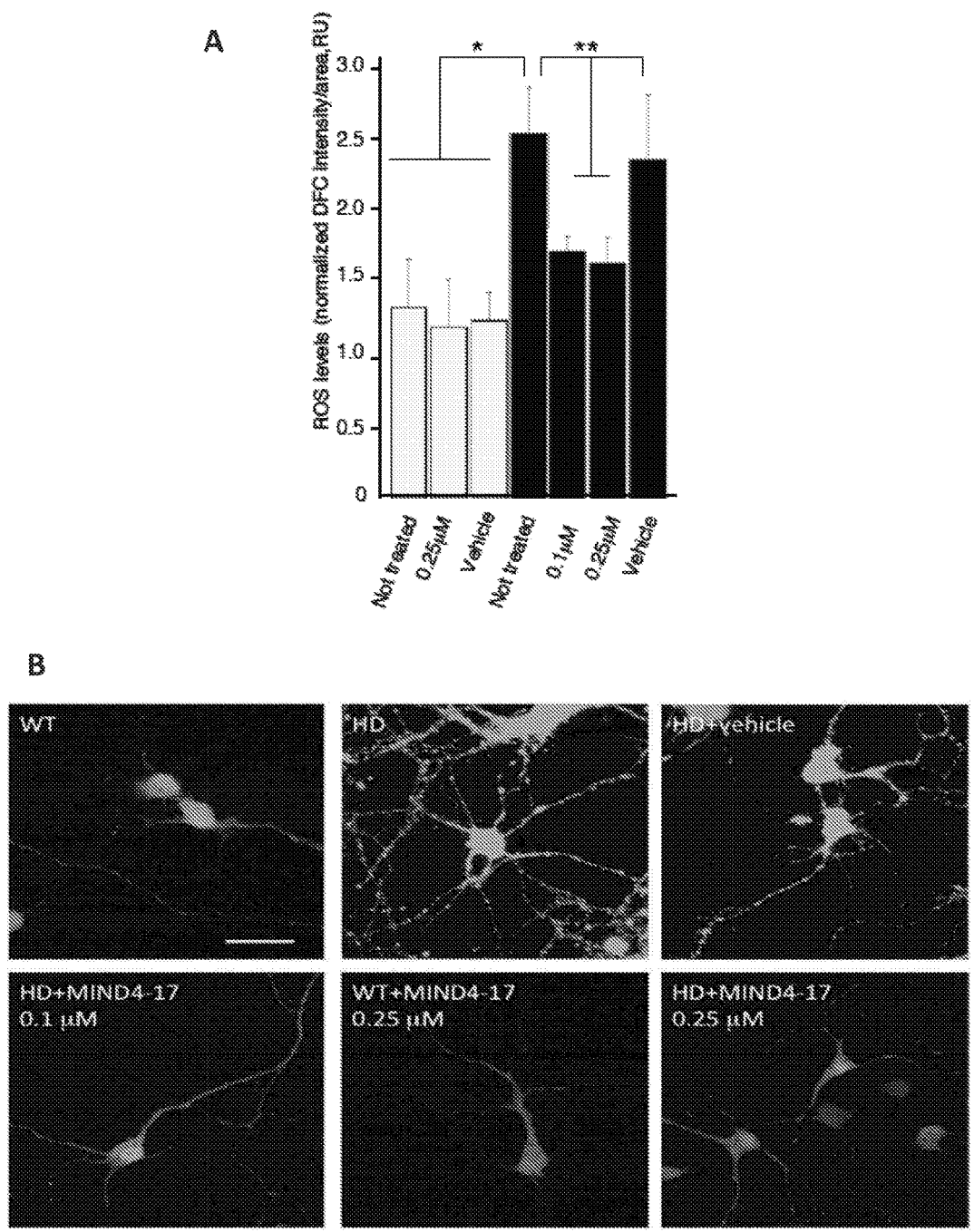
FIG. 25 Reduction of ROS levels in primary mouse neurons from 140CAG Htt knock-in mice treated with MIND4-17. Cells were treated with MIND4-17 at indicated doses at 4 DIV and ROS were measured at 8 DIV in live cells using the fluorescent indicator $H_2DCFDA$. A) Graph represents the mean of ROS levels measured in single neurons; the average intensity/area of the neuron's soma was quantified using ImageJ software. N=53 neurons was quantified in each condition; wild-type (open barograph) vs untreated HD (black barographs)*=p<0.01; untreated HD vs MIND4-17 treated HD **=p<0.05. B) Panels show fluorescent images of ROS levels in wild type (WT) and HD neurons in presence or absence of MIND4-17.

Treatment with MIND4-17 resulted in a significant reduction of ROS in HD neurons (FIG. 25A). This antioxidant effect correlated with improved cell morphology (FIG. 25B), including prevention of varicosity-like structures in neuritis and neurite thinning, and reduced swelling of soma of affected neurons [Valencia, 2013]. No effects on basal ROS levels were detected in compound-treated wild type neurons, although subtle reduction could be beyond the assay sensitivity (FIG. 25A, B). Therefore, we concluded that NRF2 activation effectively counteracted aberrantly high ROS levels induced by mHtt expression and could potentially ameliorate the burden of oxidative stress impacted by neurodegeneration.

Example 23—Drug Tests Using ROS/RNI Assays in Stimulated Microglia Cells

Dysfunction in non-neuronal cell types is recognized as a potential contributor to neurodegeration, in which a critical role for activated microglia has emerged. The antioxidant and anti-inflammatory responses in activated microglia cells by NRF2 activation have been demonstrated, providing a starting point for validating the activity of MIND4 analogs in this cell type and in the context of mHTT expression.

N9 microglial cells were cultured in RPMI medium containing Glutamax (Invitrogen) and supplemented with 10% FBS (Endotoxin levels lower than 10 EU/ml). Cells were plated in 96 well plates ($5 \times 10^4$ per well) and cultured overnight before stimulation with LPS (100 ng/ml) and TNFα (10 ng/ml) for 20 hr in medium supplemented with DMSO or with the tested compounds. ROS were detected by flow cytometry after microglia incubation with 10 mM of 5-(and-6)-chloromethyl-2',7'-dichlorodihydrofluorescein diacetate, acetyl ester (CM-$H_2$DCFDA) (Invitrogen) for 20 min. The production of NO by iNOS was measured indirectly by assaying nitrites in the culture supernatant using the Griess reaction [Liu, 2013]. Briefly, 100 ml of supernatants were incubated with equal amount of Griess reagent (1% sulphanilamide, 0.1% naphthylethylenediamine in 2% phosphoric acid solution) and the absorbance read at 550 nm after 20 min of incubation at room temperature.

Figure 26:
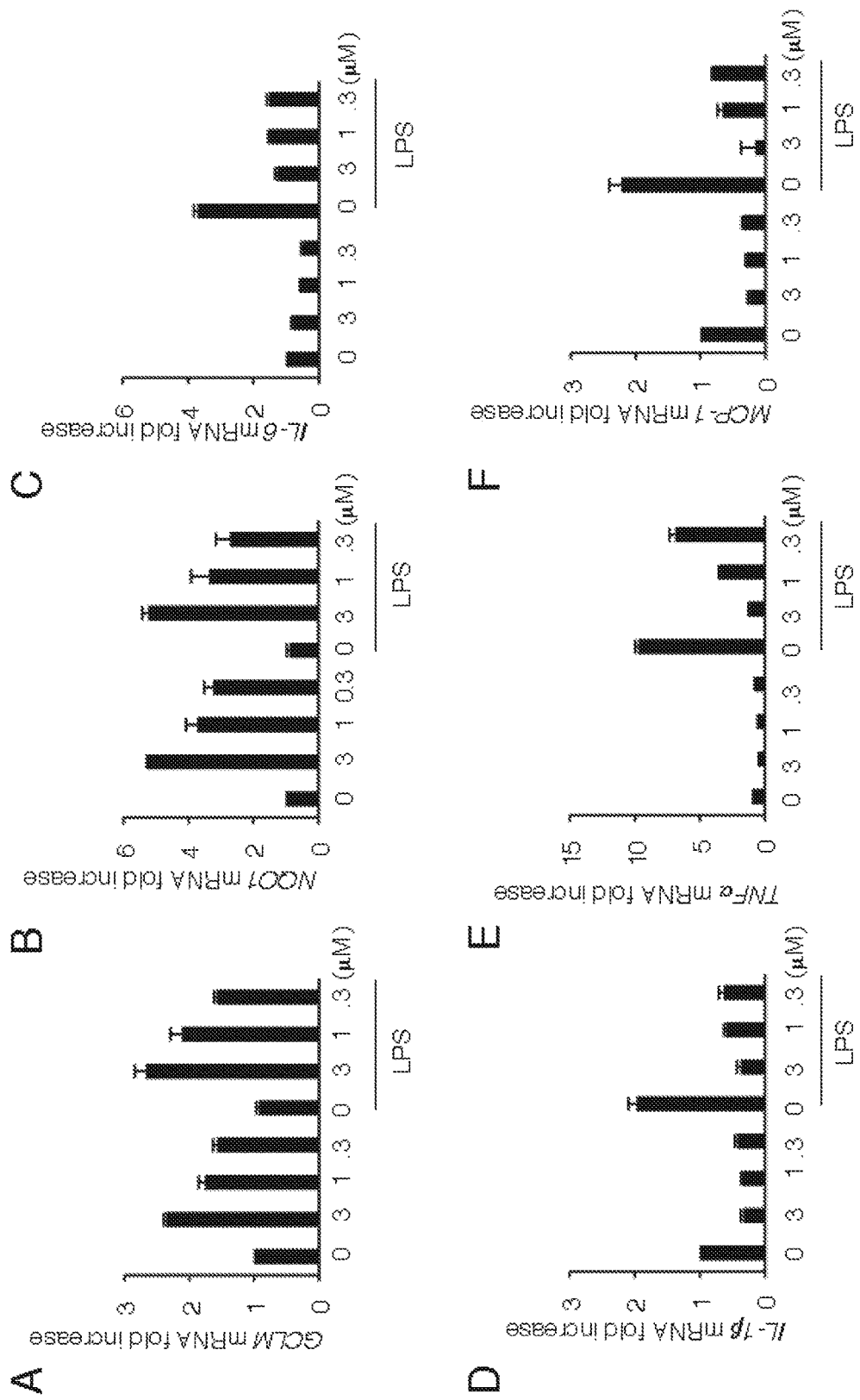
FIG. 26 NRF2 activators repress ROS and RNI in microglia cells. A-F) Dose-dependent induction of NRF2-specific transcriptional responses by MIND4-17 in resting and LPS-activated microglia cells BV2. MIND4-17 induces mRNA expression of antioxidant NRF2-responsive genes GCLM (A) and NQO1 (B) and represses expression of inflammatory factors Il-6 (C), IL-1β (D), TNFα (E), and MCP-1 (F).
Figure 27:
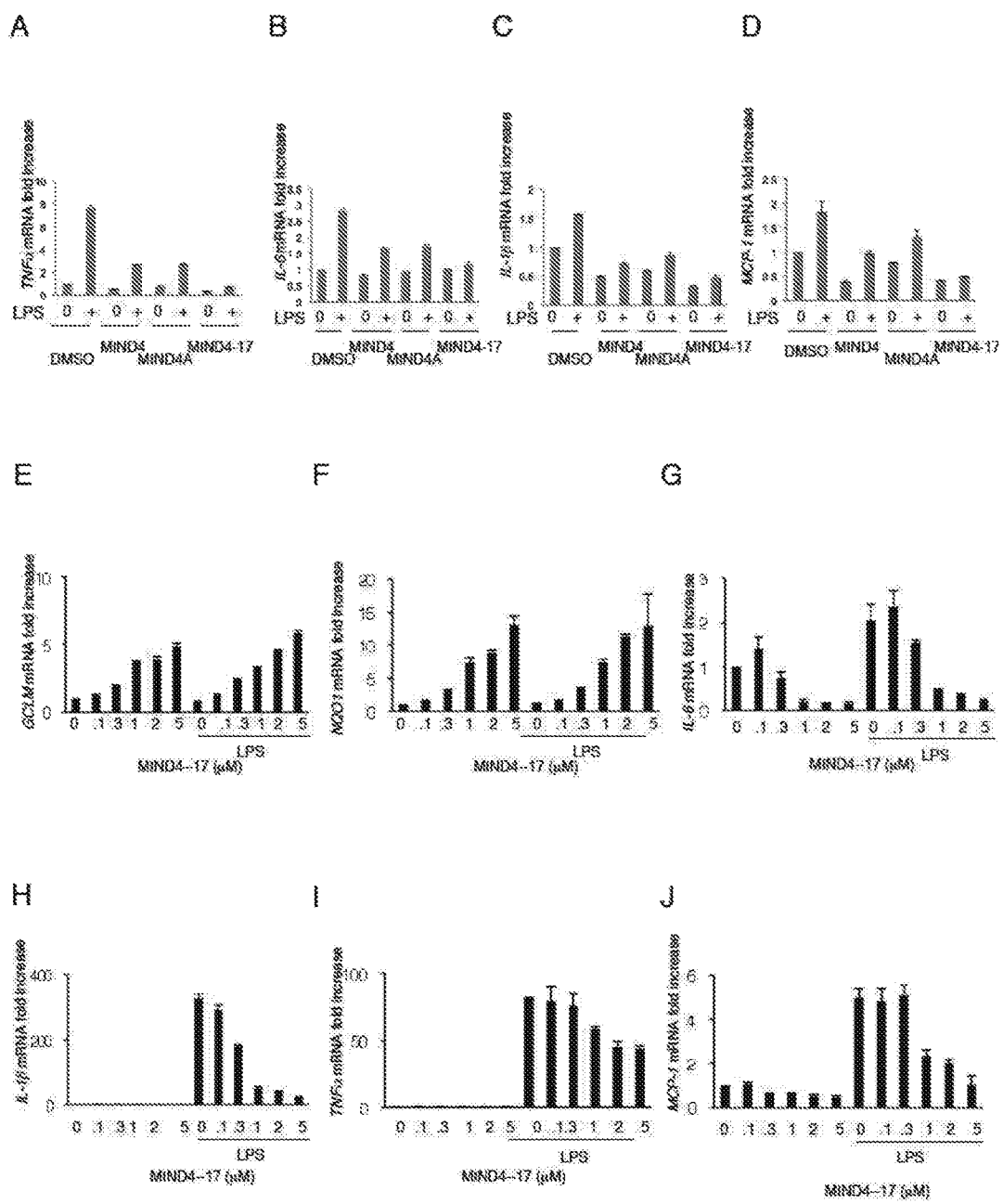
FIG. 27A-D) Comparative analysis of anti-inflammatory properties of MIND4, MIND4A, and MIND4-17 in macroglia BV2 cells. Compound effects on transcriptional expression of inflammatory factors TNFα (A), Il-6 (B), IL-1β (C), and MCP-1 (D) genes have been tested in un-induced and LPS-induced BV2 cells pre-treated with compounds at 3 µM dose for 24 hr and measured using qRT-PCR with gene-specific primers; the assessment of each gene expression was performed in duplicates. E-J) NRF2 activation-specific transcriptional responses in LPS-induced iBMM macrophages treated with MIND4-17. Dose-dependent effects of MIND4-17 treatment on mRNA expression of NRF2-responsive genes GCLM (E) and NQO1 (F), and inflammatory factors Il-6 (G), IL-1β (H), TNFα (I), and MCP-1 (J) measured using qRT-PCR with gene-specific primers; the effects on gene expression were assessed in duplicates.

Treatment with MIND4-17 potently and dose-dependent manner increased transcription of the canonical NRF2 target genes GCLM and NQO1 in resting and in activated with lipopolysaccharide (LPS) microglia cells (FIG. 26A, B). Furthermore, MIND4-17 in a dose-dependent manner repressed transcriptional expression of inflammatory factors IL-6 (FIG. 26C), IL-1β, TNFα, and MCP-1 in resting and LPS-activated microglia cells (FIG. 26D-F). The effects of MIND4-17, MIND4, and MIND4A were compared and were consistent with their NRF2 activation potencies; MIND4-17 produced greater repression of inflammatory responses in microglia cells than any of the analogs (FIG. 27A-D). The potent effects of MIND4-17 on transcriptional activation of NQO1 and GCLM and robust repression of pro-inflammatory factors were also observed in LPS-induced macrophages, suggesting a broad impact of NRF2 activation in various cell types (FIG. 27E-J).

Figure 28:
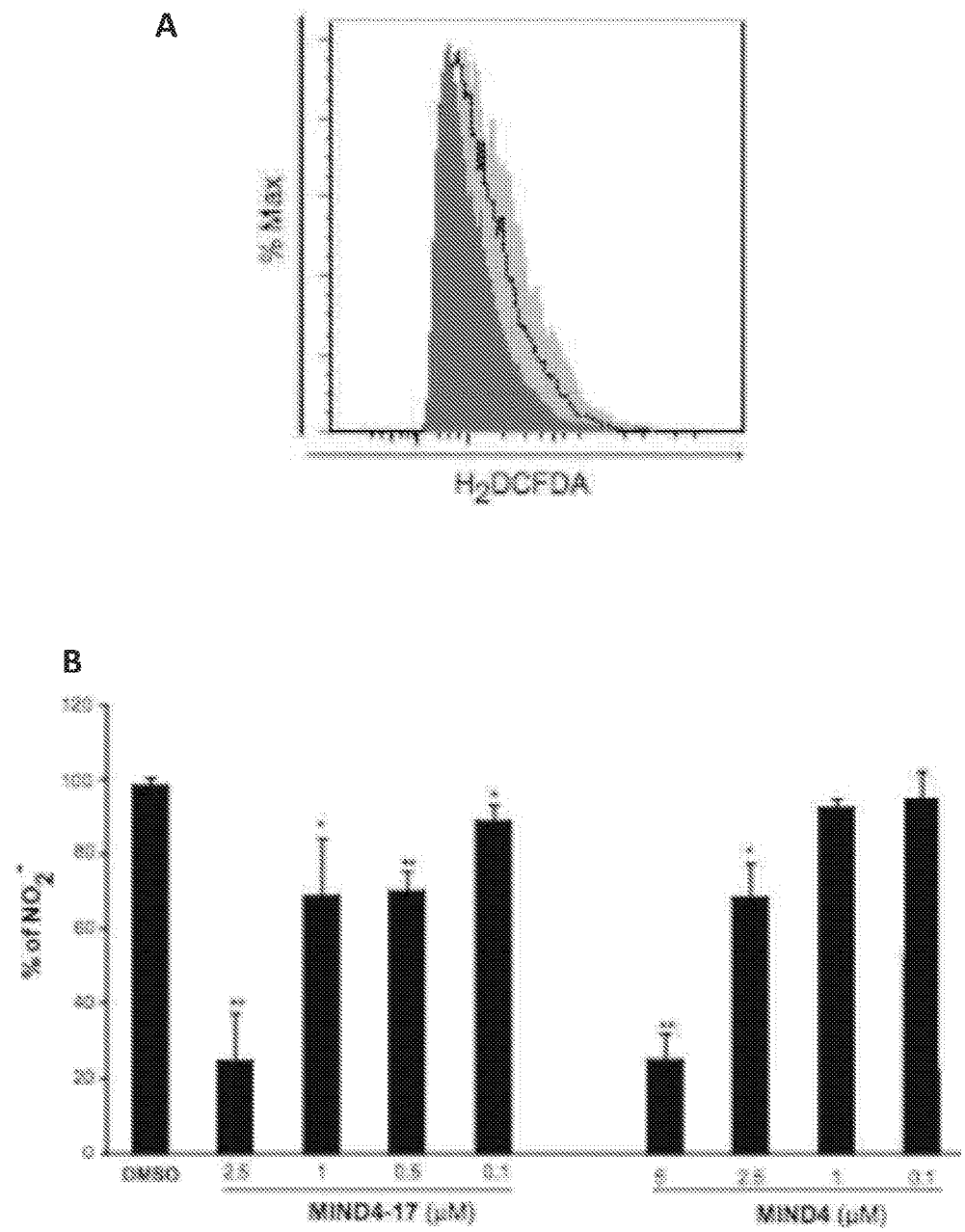
FIG. 28A) ROS production in activated microglia treated with MIND4-17 and MIND4. Representative histograms of the fluorescence intensity for the ROS probe showing the overlays of vehicle (DMSO)-treated cells (filled light gray), treated with MIND4-17 (2.5 µM) (filled dark gray) and with MIND4 (5 µM) (dotted line). B) RNI production in stimulated microglia. Cells were treated with vehicle (DMSO) or with MIND4-17 and MIND4 at indicated concentrations. RNI were assessed by measurement of iNOS-dependent release of nitrites in the culture supernatants and quantified as percent from control (DMSO treated cells). Data are presented as mean±SD of four independent experiments. t-test *=p<0.05; **=p<0.01.

The effects of NRF2 activators MIND4-17 and MIND4 on ROS levels were also examined in LPS- and TNFα-activated microglial cells. Both compounds reduced ROS levels in accord with their NRF2 activating potency (FIG. 28A). Production of nitric oxide by nitric oxide synthase (NOS) or by microglial iNOS has been proposed to participate in neurotoxicity. The effects of NRF2 activation on production of reactive nitrogen intermediates (RNAI) were examined, which has not been described previously. Treatment with MIND4-17 and MIND4 reduced the production of RNI in microglia cells, as determined by measurements of the nitrites in the cell supernatants, to levels consistent with the potencies of the compounds (FIG. 28B). These results demonstrate potent reduction of induced reactive oxygen and nitrogen species in microglia by the NRF2 activators MIND4-17 and MIND4.

Example 24—Drug Test in Primary Astrocytes and Microglia from Wild Type and YAC128 HD Mice The release of pro-inflammatory cytokines, which is associated with the harmful effects of activated microglia in brain, creates a cytotoxic environment for neighboring neurons]. Neuroinflammation responses appear to be altered relatively early in HD, suggesting that mHTT promotes abnormal release of cytokines by activated microglia. Therefore, the effects of MIND4-17 on release of pro-inflammatory cytokines in the presence and absence of mHTT was examined. First, the impact of MIND4-17 treatment on inflammatory responses in primary microglia derived from wild type and YAC128 mice was examined. The YAC128 mouse model of HD expresses a full-length human transgene with 128 CAG repeats, and replicates key elements of HD phenotypes and selective neurodegeneration. Previous studies in peripheral blood monocytes from the YAC128 focused on IL-6 as a marker of inflammation.

Whole brains were obtained from post-natal 1 to 3 day old wild type and YAC128 mouse pups on the FVB/N strain background and placed in Hanks Balanced Salt Solution (HBSS; Invitrogen) on ice. Meninges were removed and the remaining brain tissue was placed into growth medium (DMEM [Invitrogen], 10% FBS [PAA], 1% L-glutamine [Invitrogen], 1% penicillin/streptomycin [Invitrogen]), and homogenized using a 5 ml pipette. Cells of each brain were pelleted, re-suspended in growth medium and transferred into a T150 flask, cultured at 37° C. with 5% CO2. Growth medium was replaced after 24 hr and then every 7 days. After 18 to 21 days in culture, loosely attached microglia were harvested and seeded at $1.4 \times 10^5$ cells/ml with pre-incubated conditioned media into 96-well PRIMARIA™ tissue culture plates (BD Falcon). Adherent astrocytes were plated at $1.4 \times 10^5$ cells/ml in 10% FBS media for 24 hr in 96-well PRIMARIA™ tissue culture plates. After the initial isolation microglia and astrocytes were seeded at a density of $1.4 \times 10^5$ cells/ml into 96-well PRIMARIA™ tissue culture plates. 24 hours later, the culture media was replaced with media containing MIND4-17 at different concentrations in growth medium containing 1% FBS. 24 hr later medium, containing Interferon-γ (INF-γ; final concentration 10 ng/ml; R&D Systems) with or without CSE (Control Standard Endotoxin), purified from *Escherichia coli* O113: H10 (Associates of Cape Code), at final concentration 100 ng/ml. Supernatants were collected at 9 hr, and stored at −20° C. Cells were lysed and total protein levels were determined using the microBCA kit (Thermo Scientific). Supernatants were analyzed using mouse IL-6 ELISA (e-Biocience) and IL-6 levels were normalized to total protein levels.

Figure 29:
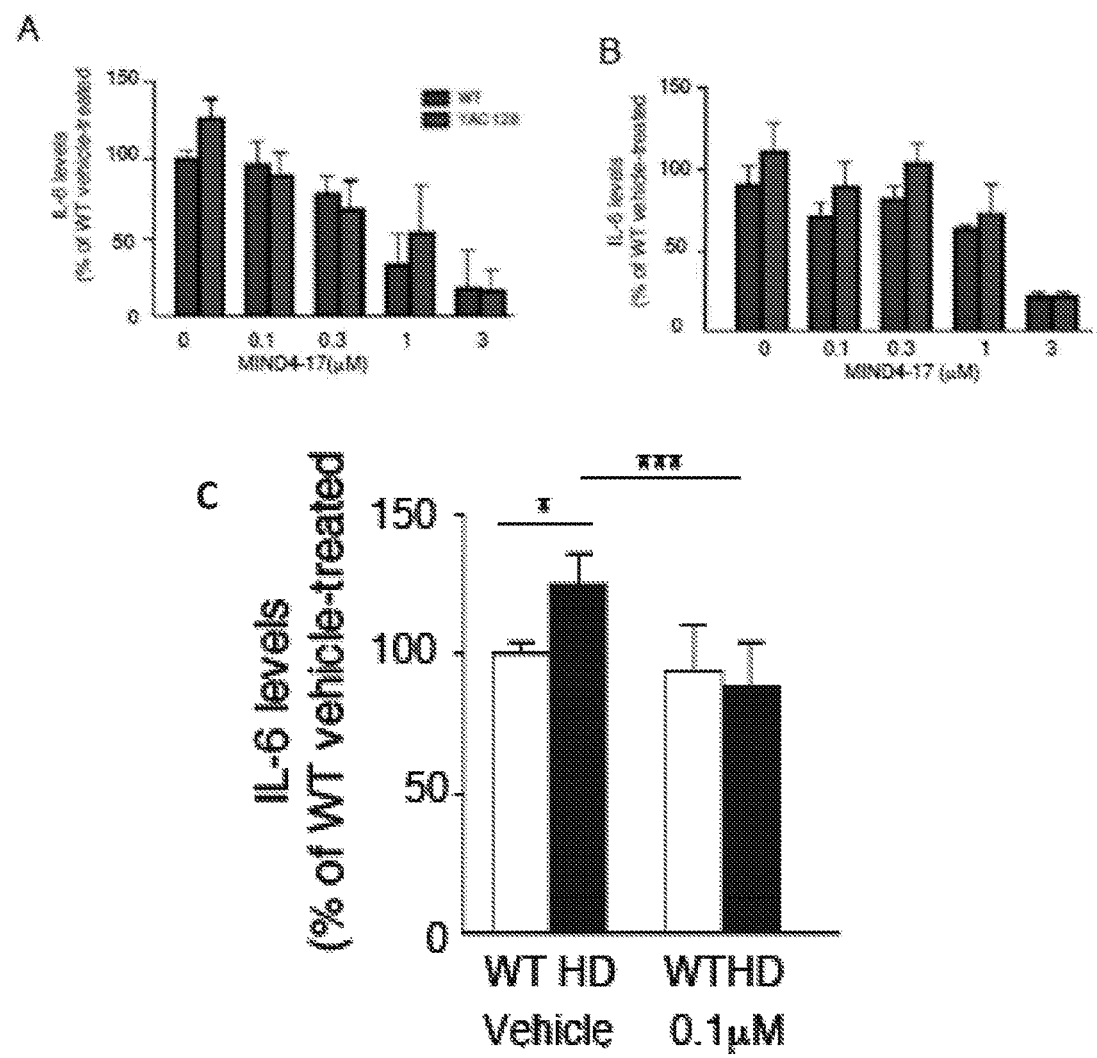
FIG. 29 MIND4-17 represses aberrant inflammatory responses in primary mouse and human cells. A-B) MIND4-17 represses release cytokine IL-6 in primary microgla (A) and astrocytes (B) from WT and YAK128 HD mice in dose dependent manner. In both cell types MIND4-7 significantly decreased the IL6 response for both genotypes with a clear dose-related response. C) Treatment with MIND4-17 reduced IL-6 secretion in both wild type (WT) and YAC128 (HD) astrocytes.
Figure 30:
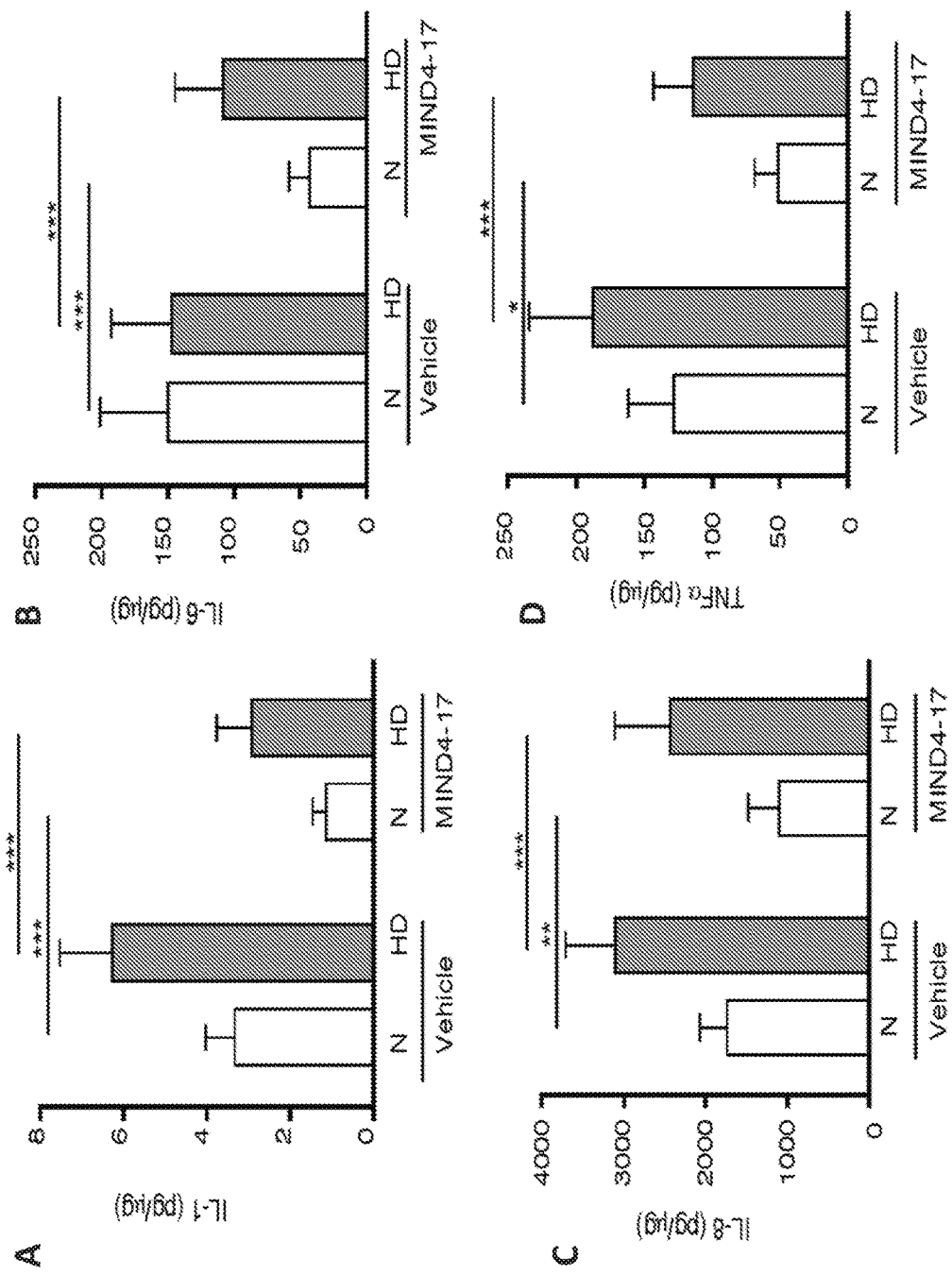
FIG. 30 A-D) MIND4-17 represses expression of induced inflammatory cytokines in primary monocytes from HD patients and normal controls. IL-1 (A), IL-6 (B), IL-8 (C), and TNFα (D) production by IFN-γ and LPS stimulated HD patient monocytes. Cytokine expression, measured by multiplex ELISA, was compared in cells treated with 3 µM MIND4-17 or vehicle (DMSO). (Linear mixed model on log transformed data, n=10 controls, n=13 for HD patients, *=p<0.05; =p<0.01, *=p<0.001.)

Release of IL-6 from wild type and YAC128 microglia was induced by stimulation with control standard endotoxin (CSE) and INF-γ. MIND4-17 reduced the amount of IL-6 secreted from wild type and YAC128 primary microglia in a dose-dependent manner (FIG. 29A). Interestingly, at low doses, MIND4-17 inhibited IL-6 release in YAC128 cells only, compensating for the apparent pro-inflammatory hyper-response of HD cells (FIG. 29C).

Experiments were extended to primary astrocytes derived from wild type and YAC128 mice. MIND4-17 treatment resulted in a similar dose-response reduction of IL-6 release in CSE-stimulated primary astrocytes derived from wild type and YAC128 mice (FIG. 29B). The results suggest a broad anti-inflammatory potential of NRF2 activation, not limited to cell type or disease context.

Example 25—MIND4-17 Treatment of Primary Human HD and Control Monocytes

The effects of the NRF2 activator MIND4-17 on inflammatory responses in primary human monocytes derived from HD patients and healthy controls was determined. Ex vivo peripheral immune cells from HD patients have been shown to produce significantly more pro-inflammatory cytokines in response to LPS and IFN-g stimulation compared to cells isolated from control subjects [Bjorkqvist, 2008; Träger, 2013].

Blood samples were obtained from control subjects and genetically-diagnosed, symptomatic HD patients. Patients were classed as having early or moderate-stage disease using the total functional capacity (TFC) scale (13-7, early; 6-3, moderate) [Marder, 2000]. Subjects with inflammatory or infective conditions were excluded. Cells were isolated from whole blood, as previously described [Björkqvist, 2008]. In brief, 50 ml whole blood was collected in heparin (CP Pharmaceuticals) and leukocytes were isolated by density gradient centrifugation. Monocytes were sorted via magnetic cell separation columns using anti-CD14 microbeads (Miltenyi Biotec). Monocytes were seeded at $1 \times 10^5$ cells per well in 96-well PRIMARIA™ tissue culture plates (BD Falcon) with R10 media (RPMI culture medium supplemented with 10% FCS, 2 mM L-glutamine, 50 U/ml penicillin and 50 mg/ml streptomycin (Invitrogen)). After resting for 16 hr, the culture media was replaced with R10 media containing either vehicle (DMSO) or MIND4-17 at different concentrations (0.3 mM, 1 mM and 3 mM). After 24 hr treatment, media was changed again using R10 containing both MIND4-17 at the same concentration and, to stimulate cytokine production, 10 ng/ml TNF-γ (R&D Systems) and 2 mg/ml lipopolysaccharide (LPS, Sigma-Aldrich, *E. coli* 055:B5, strain 1644-70. Cat. number L6529). Supernatants were collected at 24 hr, and stored at −70° C. Supernatants were analyzed using the human pro-inflammatory II (4-plex) MSD assay measuring IL-1b, IL-6, IL-8 and TNFα. Cytokine levels were normalised to total protein concentration in each well. Cells were lysed in 50 mM Tris pH 8, 150 mM NaCl, 0.5% sodium deoxycholate, 0.5% Triton X-100 and assayed for total protein concentration using a BCA assay (Thermo-Fisher). To test toxic effect of MIND4-17 on primary human leukocyte cultures, monocytes were treated with MIND4-17 but not IFN-g and LPS, mimicking the treatment duration used in the cytokine profiling experiments. Cell death was measured using a LDH assay (Cyto-Tox-Fluor™ Cytotoxicity Assay from Promega). Normalized cytokine levels have been analyzed on the logarithmic scale due to their skewed distribution. Statistical analysis was performed using a linear mixed model, to allow for correlation between measurements from the same subject. A constant correlation was assumed between all six measurements from each subject; with robust standard errors to allow for deviation from this assumption. An advantage of this approach, is that linear mixed models will provide unbiased estimates of each comparison even if there is missing data, provided the data is assumed missing at random. Contrasts of interest were then calculated using linear combinations of parameter estimates.

Information on Cohorts of HD and Healthy Subjects Participated in the Study

HD (n=13): age=56.84+/−9.23; CAG repeats=42.46+/−1.80; female/male ratio=53/47 Healthy subjects (n=10): age=49.98+/−15.03; female/male ratio=53/47

In this study, pre-treatment of primary monocytes from HD patients and normal subjects with different doses of MIND4-17 led to reduced IL-1, IL-6, IL-8, and TNFα production in response to LPS and IFN-g stimulation as compared to vehicle (DMSO) treated control (FIG. 30A-F). Treating HD patient cells with 3 mM MIND4-17 showed a significant decrease in the levels of all four cytokines (FIG. 30A-F). MIND4-17 also demonstrated a similar effect on control cells from healthy subjects (FIG. 30A-F). A full dose response curve, ranging from 0.3 µl to 3 mM, showed a similar trend over all drug doses tested. Neither vehicle (DMSO) or MIND4-17 had a toxic effect on viability of primary human monocytes at any concentration.

Notably, monocytes from HD patients showed an apparent hyper-response to stimulation, i.e. higher expression levels of pro-inflammatory cytokines IL-1, IL-8, and TNFα than cells from healthy subjects when treated with vehicle. Remarkably, the abnormally high expression of IL-1 and TNFα were returned to normal levels, and IL-8 was significantly reduced in HD monocytes treated with MIND4-17 (FIG. 30A-F). The results, demonstrating potent anti-inflammatory effects of MIND4-17 in patient's cells, strongly suggest that the NRF2 pathway is intact and responsive in HD. Altogether, the data show that aberrant inflammatory responses in HD could be attenuated by NRF2 activation as a part of neurotherapeutic strategy.

Example 26—Drug Test in Viability Assay Using Differentiated LUHMES Cells Overexpressing aSyn Given the overlap in phenotypes related to the protective effects of NRF2 signaling in both HD and PD [Johnson, 2008; Joshi, 2012; Lastres-Becker, 2012], it was determined whether the newly identified NRF2 activators were also protective against alpha-synuclein (αSyn) toxicity.

LUHMES cells were maintained as proliferating cultures and differentiated into post-mitotic-like neurons on Nunclon plates and flasks, pre-coated with 50 µg/mL poly-L-ornithine (Sigma) and 1 µg/mL fibronectin (Sigma). Specifically, 8×10$^6$ proliferating LUHMES cells were seeded into a T175 flask containing proliferation medium, consisting of advanced DEMEM/F12 (Invitrogen), 2 mM L-glutamine (Sigma-Aldrich), 1×N2 supplement (Invitrogen) and 40 ng/mL recombinant human bFGF (R&D Systems). After 24 hr, proliferation medium was replaced with differentiation medium, composed of advanced DMEM/F12 (Invitrogen), 2 mM L-glutamine (Sigma-Aldrich), 1×N2 supplement (Invitrogen), 1 mM dibutyryl 3', 5'-cyclic adenosine monophosphate (Sigma-Aldrich), 2.25 µM tetracycline and 2 ng/mL recombinant human GDNF (R&D Systems). 48 hr later, cells were trypsinized and seeded into 24-well plates, containing 1 mL of differentiation medium and 250,000 cells/well.

For lenti-virus based expression the following transfer plasmids have been constructed. Full-length human alpha-synuclein cDNA was subcloned into a second-generation of lentiviral vector pWPI (Tronolab, Switzerland), followed by an IRES-EGFP sequence. The original promoter (EF1α) was replaced by the chicken/β-actin promoter. The vector including only the IRES-GFP cassette was used for control experiments. The correct nature of all cloned sequences was confirmed by automated sequencing (StarSeq, Mainz Germany). For lentiviral snRNA production a third generation lentiviral vector pLKO.1 puro (from Sigma Aldrich) containing the following sequence 5'ACCAAAGAGCAAGT-GACAAAT-3' (SEQ ID NO. 15) was used to knock down the gene expression for human SNCA. Control experiments were performed with the vector pLKO.1 puro containing the scrambled sequence 5'CCTAAGGTTAAGTCGCCCTCG3 (SEQ ID NO. 16). Second-generation lentiviral particles were generated as described previously (Zufferey et al., 1997). After purification of the modified transfer-vectors and cotransfection with the packaging vectors (Tronolab, Switzerland) into 293 FT cells (Invitrogen) for 48 hr, the supernatant was collected, concentrated by PEG-it Virus Precipitation Solution (System Biosciences) and resuspended in Panserin 401 (PAN, Germany). The measurement of transgene expression has been determined by qRT PCR using SYBR GREEN, after infection of 293-Hek-cells, and specific primers to the woodchuck hepatitis virus posttranscriptional regulatory element (WPRE) as described previously (PMID: 12718761). Viruses were used equimolarly in all applications, stored at ~80° C., and kept on ice during cell culture procedures. Transduction was accomplished by incubating undifferentiated LUHMES cells with virus-containing supernatant for 48 hr. GFP-positive cells were selected via FACS sorting (BD Aria II). Viruses were used equimolarly in all applications, stored at ~80° C., and kept on ice during cell culture procedures.

Cell viability was measured by cellular release of adenylate kinase (AK) using quantitative bioluminescent cytotoxicity assay (ToxiLight BioAssay (Lonza) according to the manufacturer's protocol. 72 hr after cells were seeded into 24-well plates, 500 mL of conditioned supernatants were replaced with fresh differentiation medium, containing each of the compounds or vehicle control (DMSO). 96 hr after that, 20 mL of cell culture supernatants were added to individual wells of a black-walled, clear-bottom, 96-well microtiter plate. Next, 100 mL of ToxiLight AK reagent was added to each well and incubated at room temperature for 5 min. Luminescence was measured, using an Infinte M200 PRO (Tecan) plate reader, and luminescence results of the test wells were expressed as percentage of the control wells. Statistical significance was determined by t test.

The potent NRF2 activator MIND4-17 showed significant protective effects at the 0.4 µM and 1 µM doses, while the less potent MIND4 provided only mild protection in this dose range (FIG. 7A-E). These results are consistent with previously published results in fly and microglia models of PD [Barone, 2011; Beraud, 2012], demonstrating that NRF2 activation counters aSyn toxicity in dopaminergic neuronal cells.

Example 27—Docking Model of Selective Binding of MIND4 to SIRT2 Deacetyalse

For generating the SIRT2/MIND4 complex model, the compound was docked using the program FlexX (BioSolveIT, Germany) and a SIRT2/ADP-ribose structure (PDB ID 3ZGV) [Moniot, 2013]; ligand omitted for the calculation) as a receptor. The overlay with SIRT1 (PDB ID 4KXQ) and with SIRT3 in complex with carba-NAD and acetylated peptide (PDB ID 4FVT) was generated and visualized in PyMol (Schrödinger LLC, Portland, USA).

The model suggests that MIND4 blocks the binding site for the NAD$^+$ nicotinamide moiety with its phenyl group, similar to the SIRT1 inhibitor Ex-527, and the NAD$^+$ ribose binding region with its nitro quinoline group. MIND4 appears to extend its phenyl-oxo-methyl group into the hydrophobic active site pocket of SIRT2, which is larger than in SIRT1 or in SIRT3, providing a possible rationale for the compound's SIRT2 selectivity.

REFERENCES (1993). A novel gene containing a trinucleotide repeat that is expanded and unstable on Huntington's disease chromosomes. The Huntington's Disease Collaborative Research Group. Cell 72, 971-983.

Abagyan, R., and Totrov, M. (1994). Biased probability Monte Carlo conformational searches and electrostatic calculations for peptides and proteins. Journal of molecular biology 235, 983-1002.

Abagyan, R. A., Tortov, M., and Kuznetsov, D. (1994). ICM—a new method for protein modelling and design. Applications to docking and structure prediction from the distorted native conformation. J Comp Chem 15, 488-506.

Apostol, B. L., Illes, K., Pallos, J., Bodai, L., Wu, J., Strand, A., Schweitzer, E. S., Olson, J. M., Kazantsev, A., Marsh, J. L., et al. (2006). Mutant huntingtin alters MAPK signaling pathways in PC12 and striatal cells: ERK1/2 protects against mutant huntingtin-associated toxicity. Human molecular genetics 15, 273-285.

Beamer, L. J., Li, X., Bottoms, C. A., and Hannink, M. (2005). Conserved solvent and side-chain interactions in the 1.35 Angstrom structure of the Kelch domain of Keap1. Acta crystallographica 61, 1335-1342.

Bjorkqvist, M., Wild, E. J., Thiele, J., Silvestroni, A., Andre, R., Lahiri, N., Raibon, E., Lee, R. V., Benn, C. L., Soulet, D., et al. (2008). A novel pathogenic pathway of immune activation detectable before clinical onset in Huntington's disease. The Journal of experimental medicine 205, 1869-1877.

Bonifati, D. M., and Kishore, U. (2007). Role of complement in neurodegeneration and neuroinflammation. Molecular immunology 44, 999-1010.

Browne, S. E., and Beal, M. F. (2006). Oxidative damage in Huntington's disease pathogenesis. Antioxid Redox Signal 8, 2061-2073.

Calkins, M. J., Vargas, M. R., Johnson, D. A., and Johnson, J. A. (2010). Astrocyte-specific overexpression of Nrf2 protects striatal neurons from mitochondrial complex II inhibition. Toxicol Sci 115, 557-568.

Cheung, K. L., Lee, J. H., Shu, L., Kim, J. H., Sacks, D. B., and Kong, A. N. (2013). Ras GTPase-activating-like protein (IQGAP1) mediates Nrf2 activation via MEK-ERK pathway. The Journal of biological chemistry.

Chopra, V., Quinti, L., Kim, J., Vollor, L., Narayanan, K. L., Edgerly, C., Cipicchio, P. M., Lauver, M. A., Choi, S. H., Silverman, R. B., et al. (2012). The Sirtuin 2 Inhibitor AK-7 Is Neuroprotective in Huntington's Disease Mouse Models. Cell reports 2, 1492-1497.

Crittenden, J. R., Dunn, D. E., Merali, F. I., Woodman, B., Yim, M., Borkowska, A. E., Frosch, M. P., Bates, G. P., Housman, D. E., Lo, D. C., et al. (2010). CalDAG-GEFI down-regulation in the striatum as a neuroprotective change in Huntington's disease. Human molecular genetics 19, 1756-1765.

Cullinan, S. B., Gordan, J. D., Jin, J., Harper, J. W., and Diehl, J. A. (2004). The Keap1-BTB protein is an adaptor that bridges Nrf2 to a Cul3-based E3 ligase: oxidative stress sensing by a Cul3-Keap1 ligase. Molecular and cellular biology 24, 8477-8486.

Dalrymple, A., Wild, E. J., Joubert, R., Sathasivam, K., Bjorkqvist, M., Petersen, A., Jackson, G. S., Isaacs, J. D., Kristiansen, M., Bates, G. P., et al. (2007). Proteomic profiling of plasma in Huntington's disease reveals neuroinflammatory activation and biomarker candidates. Journal of proteome research 6, 2833-2840.

Das, C., Lucia, M. S., Hansen, K. C., and Tyler, J. K. (2009). CBP/p300-mediated acetylation of histone H3 on lysine 56. Nature 459, 113-117.

Ehrlich, M. E., Conti, L., Toselli, M., Taglietti, L., Fiorillo, E., Taglietti, V., Ivkovic, S., Guinea, B., Tranberg, A., Sipione, S., et al. (2001). ST14A cells have properties of a medium-size spiny neuron. Exp Neurol 167, 215-226.

Ellrichmann, G., Petrasch-Parwez, E., Lee, D. H., Reick, C., Arning, L., Saft, C., Gold, R., and Linker, R. A. (2011). Efficacy of fumaric acid esters in the R6/2 and YAC128 models of Huntington's disease. PloS one 6, e16172.

Frank-Cannon, T. C., Alto, L. T., McAlpine, F. E., and Tansey, M. G. (2009). Does neuroinflammation fan the flame in neurodegenerative diseases? Molecular neurodegeneration 4, 47.

Hersch, S. M., and Rosas, H. D. (2008). Neuroprotection for Huntington's disease: ready, set, slow. Neurotherapeutics 5, 226-236.

Hu, L., Magesh, S., Chen, L., Wang, L., Lewis, T. A., Chen, Y., Khodier, C., Inoyama, D., Beamer, L. J., Emge, T. J., et al. (2013). Discovery of a small-molecule inhibitor and cellular probe of Keap1-Nrf2 protein-protein interaction. Bioorganic & medicinal chemistry letters 23, 3039-3043.

Innamorato, N. G., Lastres-Becker, I., and Cuadrado, A. (2009). Role of microglial redox balance in modulation of neuroinflammation. Current opinion in neurology 22, 308-314.

Itoh, K., Chiba, T., Takahashi, S., Ishii, T., Igarashi, K., Katoh, Y., Oyake, T., Hayashi, N., Satoh, K., Hatayama, I., et al. (1997). An Nrf2/small Maf heterodimer mediates the induction of phase II detoxifying enzyme genes through antioxidant response elements. Biochemical and biophysical research communications 236, 313-322.

Jin, Y. N., Yu, Y. V., Gundemir, S., Jo, C., Cui, M., Tieu, K., and Johnson, G. V. (2013). Impaired mitochondrial dynamics and Nrf2 signaling contribute to compromised responses to oxidative stress in striatal cells expressing full-length mutant huntingtin. PloS one 8, e57932.

Johnson, J. A., Johnson, D. A., Kraft, A. D., Calkins, M. J., Jakel, R. J., Vargas, M. R., and Chen, P. C. (2008). The Nrf2-ARE pathway: an indicator and modulator of oxidative stress in neurodegeneration. Annals of the New York Academy of Sciences 1147, 61-69.

Johri, A., and Beal, M. F. (2012). Antioxidants in Huntington's disease. Biochimica et biophysica acta 1822, 664-674.

Joshi, G., and Johnson, J. A. (2012). The Nrf2-ARE Pathway: A Valuable Therapeutic Target for the Treatment of Neurodegenerative Diseases. Recent patents on CNS drug discovery.

Jung, K. A., and Kwak, M. K. (2010). The Nrf2 system as a potential target for the development of indirect antioxidants. Molecules 15, 7266-7291.

Kensler, T. W., Wakabayashi, N., and Biswal, S. (2007). Cell survival responses to environmental stresses via the Keap1-Nrf2-ARE pathway. Annual review of pharmacology and toxicology 47, 89-116.

Killoran, A., and Biglan, K. M. (2012). Therapeutics in Huntington's Disease. Current treatment options in neurology.

Koh, K., Kim, J., Jang, Y. J., Yoon, K., Cha, Y., Lee, H. J., and Kim, J. (2011). Transcription factor Nrf2 suppresses LPS-induced hyperactivation of BV-2 microglial cells. Journal of neuroimmunology 233, 160-167.

Kraft, A. D., Kaltenbach, L. S., Lo, D. C., and Harry, G. J. (2012). Activated microglia proliferate at neurites of mutant huntingtin-expressing neurons. Neurobiology of aging 33, 621 e617-633.

LaPash Daniels, C. M., Austin, E. V., Rockney, D. E., Jacka, E. M., Hagemann, T. L., Johnson, D. A., Johnson, J. A., and Messing, A. (2012). Beneficial effects of Nrf2 over-expression in a mouse model of Alexander disease. J Neurosci 32, 10507-10515.

Lee, J. M., Calkins, M. J., Chan, K., Kan, Y. W., and Johnson, J. A. (2003). Identification of the NF-E2-related factor-2-dependent genes conferring protection against oxidative stress in primary cortical astrocytes using oligonucleotide microarray analysis. The Journal of biological chemistry 278, 12029-12038.

Lee, O. H., Jain, A. K., Papusha, V., and Jaiswal, A. K. (2007). An auto-regulatory loop between stress sensors INrf2 and Nrf2 controls their cellular abundance. The Journal of biological chemistry 282, 36412-36420.

Li, X., Valencia, A., McCloiy, H., Sapp, E., Kegel, K. B., and Difiglia, M. (2012). Deficient Rab11 activity underlies glucose hypometabolism in primary neurons of Huntington's disease mice. Biochemical and biophysical research communications 421, 727-730.

Li, X., Zhang, D., Hannink, M., and Beamer, L. J. (2004). Crystal structure of the Kelch domain of human Keap1. The Journal of biological chemistry 279, 54750-54758.

Lo, S. C., Li, X., Henzl, M. T., Beamer, L. J., and Hannink, M. (2006). Structure of the Keap1:Nrf2 interface provides mechanistic insight into Nrf2 signaling. The EMBO journal 25, 3605-3617.

Luthi-Carter, R., Taylor, D. M., Pallos, J., Lambert, E., Amore, A., Parker, A., Moffitt, H., Smith, D. L., Runne, H., Gokce, O., et al. (2010). SIRT2 inhibition achieves neuroprotection by decreasing sterol biosynthesis. Proceedings of the National Academy of Sciences of the United States of America 107, 7927-7932.

Mangiarini, L., Sathasivam, K., Seller, M., Cozens, B., Harper, A., Hetherington, C., Lawton, M., Trottier, Y., Lehrach, H., Davies, S. W., et al. (1996). Exon 1 of the HD gene with an expanded CAG repeat is sufficient to cause a progressive neurological phenotype in transgenic mice. Cell 87, 493-506.

Marcotte, D., Zeng, W., Hus, J. C., McKenzie, A., Hession, C., Jin, P., Bergeron, C., Lugovskoy, A., Enyedy, I., Cuervo, H., et al. (2013) Small molecules inhibit the interaction of Nrf2 and the Keap1 Kelch domain through a non-covalent mechanism. Bioorganic & medicinal chemistry.

Marsh, J. L., Pallos, J., and Thompson, L. M. (2003). Fly models of Huntington's disease. Human molecular genetics 12 Spec No 2, R187-193.

Maxwell, M. M., Tomkinson, E. M., Nobles, J., Wizeman, J. W., Amore, A. M., Quinti, L., Chopra, V., Hersch, S. M., and Kazantsev, A. G. (2011). The Sirtuin 2 microtubule deacetylase is an abundant neuronal protein that accumulates in the aging CNS. Human molecular genetics 20, 3986-3996.

Moller, T. (2010). Neuroinflammation in Huntington's disease. J Neural Transm 117, 1001-1008.

Neves, M. A., Totrov, M., and Abagyan, R. (2012). Docking and scoring with ICM: the benchmarking results and strategies for improvement. Journal of computer-aided molecular design 26, 675-686.

Outeiro, T. F., Kontopoulos, E., Altmann, S. M., Kufareva, I., Strathearn, K. E., Amore, A. M., Volk, C. B., Maxwell, M. M., Rochet, J. C., McLean, P. J., et al. (2007). Sirtuin 2 inhibitors rescue alpha-synuclein-mediated toxicity in models of Parkinson's disease. Science 317, 516-519.

Pallos, J., Bodai, L., Lukacsovich, T., Purcell, J. M., Steffan, J. S., Thompson, L. M., and Marsh, J. L. (2008) Inhibition of specific HDACs and sirtuins suppresses pathogenesis in a Drosophila model of Huntington's disease. Human molecular genetics 17, 3767-3775.

Pavese, N., Gerhard, A., Tai, Y. F., Ho, A. K., Turkheimer, F., Barker, R. A., Brooks, D. J., and Piccini, P. (2006). Microglial activation correlates with severity in Huntington disease: a clinical and PET study. Neurology 66, 1638-1643.

Petri, S., Korner, S., and Kiaei, M. (2012). Nrf2/ARE Signaling Pathway: Key Mediator in Oxidative Stress and Potential Therapeutic Target in ALS. Neurology research international 2012, 878030.

Pizza, V., Agresta, A., D'Acunto, C. W., Festa, M., and Capasso, A. (2011). Neuroinflamm-aging and neurodegenerative diseases: an overview. CNS & neurological disorders drug targets 10, 621-634.

Politis, M., Pavese, N., Tai, Y. F., Kiferle, L., Mason, S. L., Brooks, D. J., Tabrizi, S. J., Barker, R. A., and Piccini, P. (2011). Microglial activation in regions related to cognitive function predicts disease onset in Huntington's disease: a multimodal imaging study. Human brain mapping 32, 258-270.

Poon, L. H., Kang, G. A., and Lee, A. J. (2010). Role of tetrabenazine for Huntington's disease-associated chorea. The Annals of pharmacotherapy 44, 1080-1089.

Quintanilla, R. A., and Johnson, G. V. (2009). Role of mitochondrial dysfunction in the pathogenesis of Huntington's disease. Brain research bulletin 80, 242-247.

Quinti, L., Chopra, V., Rotili, D., Valente, S., Amore, A., Franci, G., Meade, S., Valenza, M., Altucci, L., Maxwell, M. M., et al. (2010). Evaluation of histone deacetylases as drug targets in Huntington's disease models. Study of HDACs in brain tissues from R6/2 and CAG140 knock-in HD mouse models and human patients and in a neuronal HD cell model. PLoS currents 2.

Reinhart, P. H., Kaltenbach, L. S., Essrich, C., Dunn, D. E., Eudailey, J. A., DeMarco, C. T., Turmel, G. J., Whaley, J. C., Wood, A., Cho, S., et al. (2011). Identification of anti-inflammatory targets for Huntington's disease using a brain slice-based screening assay. Neurobiology of disease 43, 248-256.

Ribeiro, M., Rosenstock, T. R., Cunha-Oliveira, T., Ferreira, I. L., Oliveira, C. R., and Rego, A. C. (2012). Glutathione redox cycle dysregulation in Huntington's disease knock-in striatal cells. Free radical biology & medicine 53, 1857-1867.

Schwab, C., Klegeris, A., and McGeer, P. L. (2010) Inflammation in transgenic mouse models of neurodegenerative disorders. Biochimica et biophysica acta 1802, 889-902.

Shih, A. Y., Imbeault, S., Barakauskas, V., Erb, H., Jiang, L., Li, P., and Murphy, T. H. (2005). Induction of the Nrf2-driven antioxidant response confers neuroprotection during mitochondrial stress in vivo. The Journal of biological chemistry 280, 22925-22936.

Silvestroni, A., Faull, R. L., Strand, A. D., and Moller, T. (2009). Distinct neuroinflammatory profile in post-mortem human Huntington's disease. Neuroreport 20, 1098-1103.

Sorolla, M. A., Reverter-Branchat, G., Tamarit, J., Ferrer, I., Ros, J., and Cabiscol, E. (2008). Proteomic and oxidative stress analysis in human brain samples of Huntington disease. Free radical biology & medicine 45, 667-678.

Sorolla, M. A., Rodriguez-Colman, M. J., Vall-llaura, N., Tamarit, J., Ros, J., and Cabiscol, E. (2012). Protein oxidation in Huntington disease. BioFactors (Oxford, England) 38, 173-185.

Stack, C., Ho, D., Wille, E., Calingasan, N. Y., Williams, C., Liby, K., Sporn, M., Dumont, M., and Beal, M. F. (2010). Triterpenoids CDDO-ethyl amide and CDDO-trifluoroethyl amide improve the behavioral phenotype and brain pathology in a transgenic mouse model of Huntington's disease. Free radical biology & medicine 49, 147-158.

Steffan, J. S., Bodai, L., Pallos, J., Poelman, M., McCampbell, A., Apostol, B. L., Kazantsev, A., Schmidt, E., Zhu, Y. Z., Greenwald, M., et al. (2001). Histone deacetylase inhibitors arrest polyglutamine-dependent neurodegeneration in *Drosophila*. Nature 413, 739-743.

Stepkowski, T. M., and Kruszewski, M. K. (2011). Molecular cross-talk between the NRF2/KEAP1 signaling pathway, autophagy, and apoptosis. Free radical biology & medicine 50, 1186-1195.

Tai, Y. F., Pavese, N., Gerhard, A., Tabrizi, S. J., Barker, R. A., Brooks, D. J., and Piccini, P. (2007). Imaging microglial activation in Huntington's disease. Brain research bulletin 72, 148-151.

Tong, K. I., Kobayashi, A., Katsuoka, F., and Yamamoto, M. (2006). Two-site substrate recognition model for the Keap1-Nrf2 system: a hinge and latch mechanism Biological chemistry 387, 1311-1320.

Tong, K. I., Padmanabhan, B., Kobayashi, A., Shang, C., Hirotsu, Y., Yokoyama, S., and Yamamoto, M. (2007). Different electrostatic potentials define ETGE and DLG motifs as hinge and latch in oxidative stress response. Molecular and cellular biology 27, 7511-7521.

Totrov, M., and Abagyan, R. (1997). Flexible protein-ligand docking by global energy optimization in internal coordinates. Proteins Suppl 1, 215-220.

Totrov, M., and Abagyan, R. (2001). Rapid boundary element solvation electrostatics calculations in folding simulations: successful folding of a 23-residue peptide. Biopolymers 60, 124-133.

Tsunemi, T., Ashe, T. D., Morrison, B. E., Soriano, K. R., Au, J., Roque, R. A., Lazarowski, E. R., Damian, V. A., Masliah, E., and La Spada, A. R. (2012). PGC-1alpha rescues Huntington's disease proteotoxicity by preventing oxidative stress and promoting TFEB function. Science translational medicine 4, 142ra197.

Tufekci, K. U., Civi Bayin, E., Genc, S., and Genc, K. (2011). The Nrf2/ARE Pathway: A Promising Target to Counteract Mitochondrial Dysfunction in Parkinson's Disease. Parkinson's disease 2011, 314082.

Valencia, A., Sapp, E., Kimm, J. S., McClory, H., Reeves, P. B., Alexander, J., Ansong, K. A., Masso, N., Frosch, M. P., Kegel, K. B., et al. (2013). Elevated NADPH oxidase activity contributes to oxidative stress and cell death in Huntington's disease. Human molecular genetics 22, 1112-1131.

van Muiswinkel, F. L., and Kuiperij, H. B. (2005). The Nrf2-ARE Signalling pathway: promising drug target to combat oxidative stress in neurodegenerative disorders. Current drug targets 4, 267-281.

Varma, H., Cheng, R., Voisine, C., Hart, A. C., and Stockwell, B. R. (2007) Inhibitors of metabolism rescue cell death in Huntington's disease models. Proceedings of the National Academy of Sciences of the United States of America 104, 14525-14530.

Zadori, D., Klivenyi, P., Szalardy, L., Fulop, F., Toldi, J., and Vecsei, L. (2012). Mitochondrial disturbances, excitotoxicity, neuroinflammation and kynurenines: novel therapeutic strategies for neurodegenerative disorders. J Neurol Sci 322, 187-191.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a neurodegenerative disorder selected from the group consisting of: Parkinson's disease (PD), Huntington's disease (HD), multiple sclerosis (MS), frontotemporal dementia, and amyotrophic lateral sclerosis (ALS) in a subject, the method comprising administering to the subject a therapeutically effective amount of a compound selected from the group consisting of:

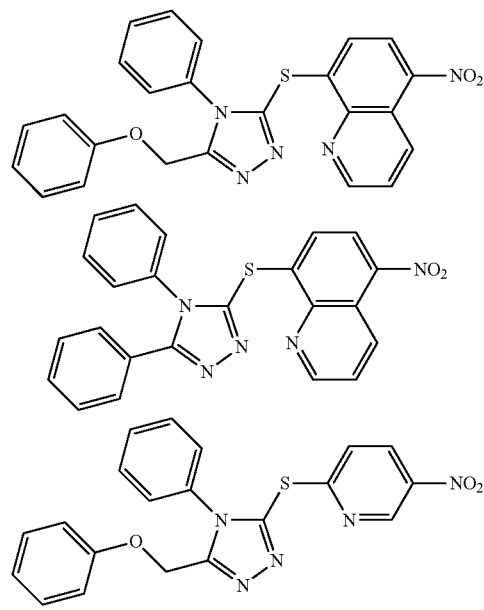

63
-continued
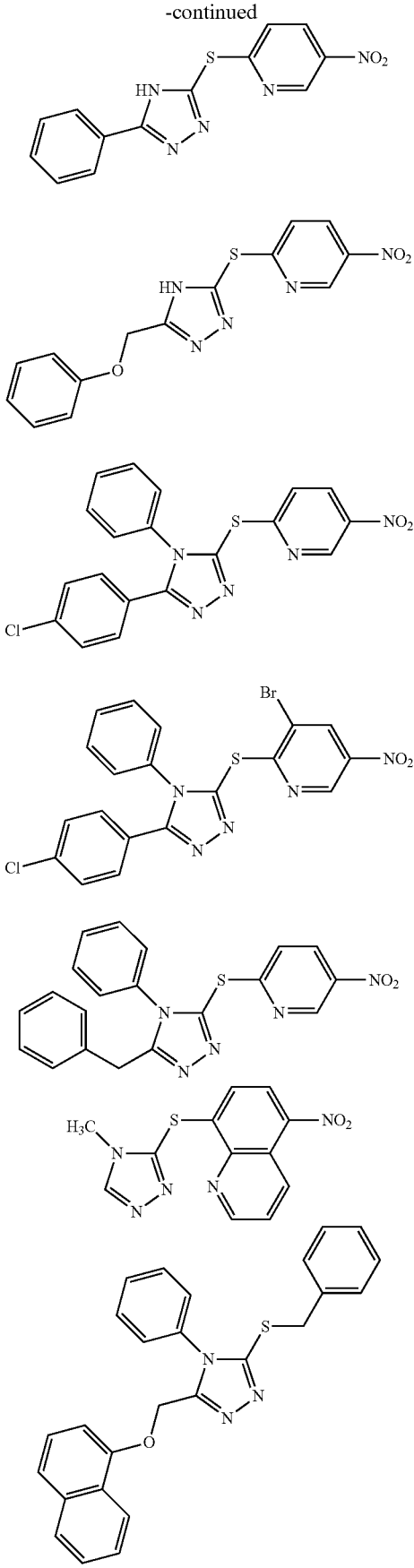
64
-continued
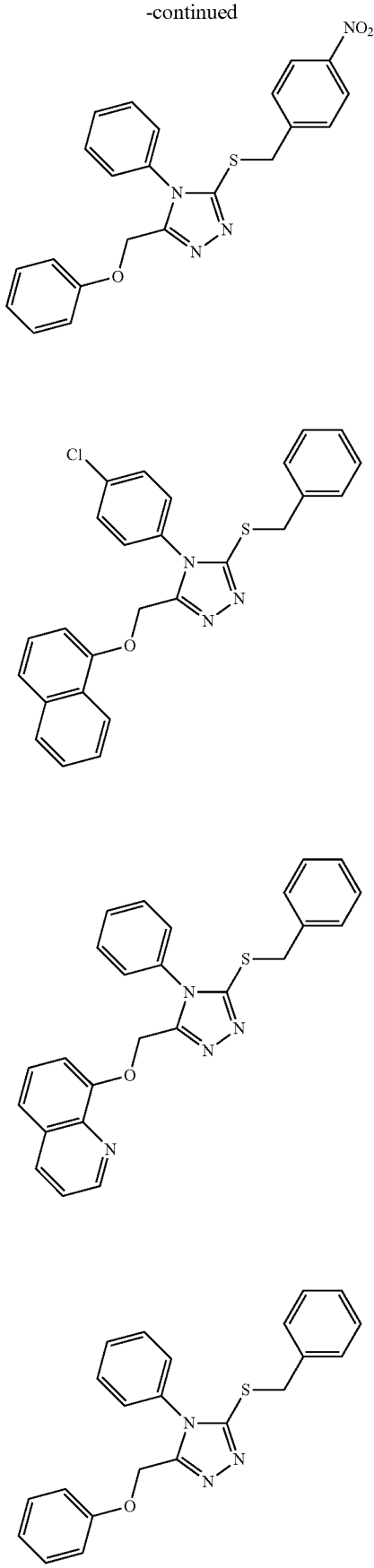

-continued

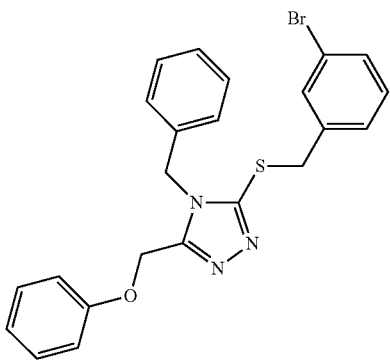

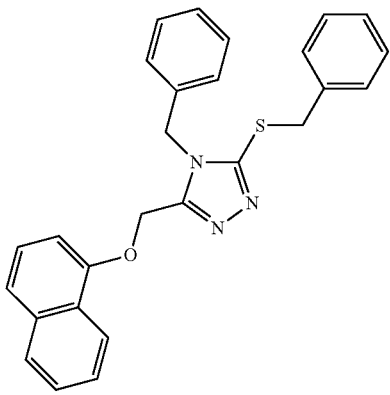

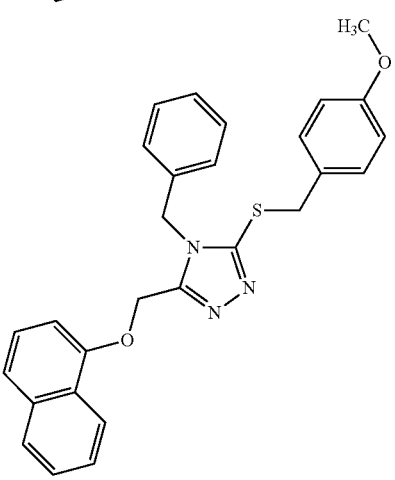

or a pharmaceutically acceptable salt thereof.

2. The method of claim 1, wherein the compound is:

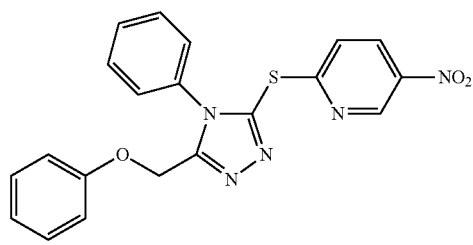 [SMILES: O=[N+]([O-])c1ccc(Sc2nnc(COc3ccccc3)n2-c2ccccc2)nc1]

or a pharmaceutically acceptable salt thereof.

3. The method of claim 1, wherein the compound is:

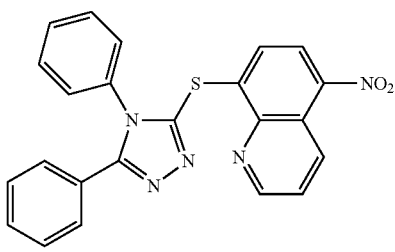 [SMILES: O=[N+]([O-])c1ccc(Sc2nnc(-c3ccccc3)n2-c2ccccc2)c2ncccc12]

or a pharmaceutically acceptable salt thereof.

4. The method of claim 1, wherein the compound is:

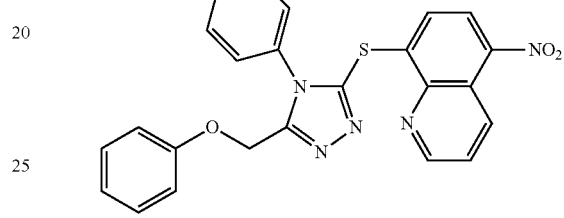

or a pharmaceutically acceptable salt thereof.

5. The method of claim 1, wherein the compound is:

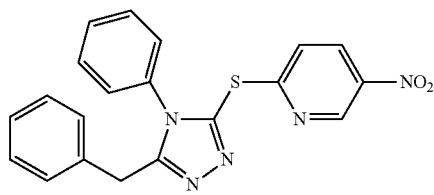 [SMILES: O=[N+]([O-])c1ccc(Sc2nnc(Cc3ccccc3)n2-c2ccccc2)nc1]

or a pharmaceutically acceptable salt thereof.

6. The method of claim 1, wherein the compound is:

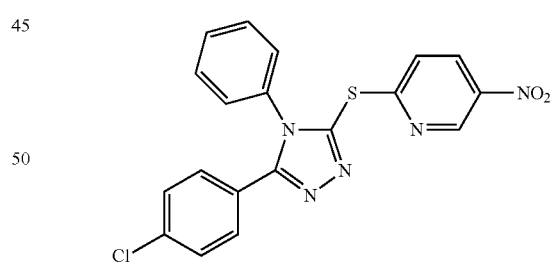

or a pharmaceutically acceptable salt thereof.

7. The method of claim 1, wherein the neurodegenerative disorder is Huntington's disease (HD).

8. The method of claim 1, wherein the neurodegenerative disorder is Parkinson's disease (PD).

9. The method of claim 1, wherein the neurodegenerative disorder is multiple sclerosis (MS).

10. The method of claim 1, wherein the neurodegenerative disorder is frontotemporal dementia.

11. The method of claim 1, wherein the neurodegenerative disorder is amyotrophic lateral sclerosis (ALS).

* * * * *